US012318411B2

(12) United States Patent
Simmons et al.

(10) Patent No.: US 12,318,411 B2
(45) Date of Patent: Jun. 3, 2025

(54) PROBIOTIC METHOD AND COMPOSITION FOR MAINTAINING A HEALTHY VAGINAL MICROBIOME

(71) Applicant: Seed Health, Inc., Venice, CA (US)

(72) Inventors: Sheri Simmons, Brookline, MA (US); Tye Jensen, Telluride, CO (US); Joseph E. Kovarik, Englewood, CO (US)

(73) Assignee: Seed Health, Inc., Venice (CA)

( * ) Notice: Subject to any disclaimer, the term of this patent is extended or adjusted under 35 U.S.C. 154(b) by 0 days.

(21) Appl. No.: 18/738,464

(22) Filed: Jun. 10, 2024

(65) Prior Publication Data

US 2024/0366687 A1    Nov. 7, 2024

Related U.S. Application Data

(63) Continuation of application No. 18/620,483, filed on Mar. 28, 2024, which is a continuation of application No. 18/615,672, filed on Mar. 25, 2024, which is a continuation of application No. 18/234,132, filed on Aug. 15, 2023, now Pat. No. 11,980,643, which is a continuation-in-part of application No. 18/232,980, filed on Aug. 11, 2023, now Pat. No. 11,969,445, which is a continuation-in-part of application No. 18/232,433, filed on Aug. 10, 2023, now Pat. No. 12,005,085, which is a continuation-in-part of application No. 18/143,399, filed on May 4, 2023, now Pat. No. 11,951,140, which is a continuation of application No. 17/893,384, filed on Aug. 23, 2022, now Pat. No. 11,951,139, which is a continuation-in-part of application No. 17/694,775, filed on Mar. 15, 2022, which is a continuation-in-part of application No. 17/023,736, filed on Sep. 17, 2020, now Pat. No. 11,419,903, which is a continuation-in-part of application No. 17/011,175, filed on Sep. 3, 2020, now Pat. No. 11,273,187, which is a continuation-in-part of application No. 16/722,117, filed on Dec. 20, 2019, now Pat. No. 10,842,834, which is a continuation-in-part of application No. 16/229,252, filed on Dec. 21, 2018, now Pat. No. 10,512,661, which is a continuation-in-part of application No. 15/392,173, filed on Dec. 28, 2016, now Pat. No. 10,245,288, application No. 18/738,464 is a continuation of application No. 18/535,722, filed on Dec. 11, 2023, which is a continuation-in-part of application No. 18/235,686, filed on Aug. 18, 2023, now Pat. No. 11,998,574, and a continuation-in-part of application No. 18/130,946, filed on Apr. 5, 2023, now Pat. No. 11,833,177, which is a continuation-in-part of application No. 18/178,847, filed on Mar. 28, 2023, now Pat. No. 11,839,632, (Continued)

(51) Int. Cl.
| | |
|---|---|
| A61K 35/74 | (2015.01) |
| A61K 31/58 | (2006.01) |
| A61K 31/715 | (2006.01) |
| A61K 35/00 | (2006.01) |
| A61K 35/741 | (2015.01) |
| A61K 35/745 | (2015.01) |
| A61K 35/747 | (2015.01) |
| A61K 38/17 | (2006.01) |
| C12N 1/20 | (2006.01) |

(52) U.S. Cl.
CPC .............. *A61K 35/74* (2013.01); *A61K 31/58* (2013.01); *A61K 31/715* (2013.01); *A61K 35/741* (2013.01); *A61K 35/745* (2013.01); *A61K 35/747* (2013.01); *A61K 38/1709* (2013.01); *A61K 38/1758* (2013.01); *C12N 1/20* (2013.01); *A61K 2035/11* (2013.01); *A61K 2035/115* (2013.01)

(58) Field of Classification Search
None
See application file for complete search history.

(56) References Cited

U.S. PATENT DOCUMENTS

| | | |
|---|---|---|
| 1,492,600 A | 5/1924 | Laskey |
| 3,178,341 A | 4/1965 | Hamill et al. |

(Continued)

FOREIGN PATENT DOCUMENTS

| | | |
|---|---|---|
| DE | 4412190 | 10/1995 |
| EP | 410696 | 1/1991 |

(Continued)

OTHER PUBLICATIONS

U.S. Appl. No. 17/854,389, filed Jun. 30, 2022, Kovarik.

(Continued)

*Primary Examiner* — Brian Gangle
(74) *Attorney, Agent, or Firm* — Sheridan Ross P.C.

(57) ABSTRACT

A method to reduce the likelihood of a dysbiosis of the vaginal microbiome in an individual employing a probiotic method and composition for maintaining a healthy vaginal microbiome, with particular embodiments including a bacterial formulation of three distinct species of *Lactobacillus crispatus* bacteria. In certain embodiments, the bacterial formulation is administered to an individual's vagina in an amount sufficient for the bacterial formulation to generate an amount of tryptophan metabolites sufficient to act as aryl hydrocarbon receptor (AHR) agonists, thereby reducing inflammation in the individual's vagina.

19 Claims, 11 Drawing Sheets

Related U.S. Application Data which is a continuation-in-part of application No. 18/087,545, filed on Dec. 22, 2022, now Pat. No. 11,826,388, which is a continuation-in-part of application No. 17/854,422, filed on Jun. 30, 2022, now Pat. No. 11,672,835, which is a continuation-in-part of application No. 17/848,759, filed on Jun. 24, 2022, now Pat. No. 11,642,382, which is a continuation-in-part of application No. 17/835,204, filed on Jun. 8, 2022, now Pat. No. 11,529,379, which is a continuation-in-part of application No. 17/567,295, filed on Jan. 3, 2022, which is a continuation-in-part of application No. 17/337,600, filed on Jun. 3, 2021, now Pat. No. 11,213,552, which is a continuation-in-part of application No. 17/027,953, filed on Sep. 22, 2020, now Pat. No. 11,026,982, which is a continuation-in-part of application No. 16/917,096, filed on Jun. 30, 2020, now Pat. No. 10,940,169, which is a continuation-in-part of application No. 16/782,364, filed on Feb. 5, 2020, now Pat. No. 10,835,560, which is a continuation-in-part of application No. 16/423,375, filed on May 28, 2019, now Pat. No. 10,555,976, which is a continuation of application No. 16/160,336, filed on Oct. 15, 2018, now Pat. No. 10,314,866, which is a continuation of application No. 15/403,823, filed on Jan. 11, 2017, now Pat. No. 10,111,913, application No. 18/738,464 is a continuation of application No. 18/234,544, filed on Aug. 16, 2023, now Pat. No. 11,998,479, said application No. 18/232,433 is a continuation-in-part of application No. 18/103,768, filed on Jan. 31, 2023, now Pat. No. 11,844,720, which is a continuation-in-part of application No. 17/738,771, filed on May 6, 2022, which is a continuation-in-part of application No. 16/904,056, filed on Jun. 17, 2020, now Pat. No. 11,523,934, which is a continuation-in-part of application No. 15/983,250, filed on May 18, 2018, now Pat. No. 10,687,975, which is a continuation-in-part of application No. 15/384,716, filed on Dec. 20, 2016, now Pat. No. 9,987,224, application No. 18/738,464 is a continuation of application No. 17/836,079, filed on Jun. 9, 2022, which is a continuation-in-part of application No. 16/884,772, filed on May 27, 2020, now Pat. No. 11,357,722, which is a continuation-in-part of application No. 16/136,950, filed on Sep. 20, 2018, now Pat. No. 10,668,014, which is a continuation of application No. 15/385,278, filed on Dec. 20, 2016, now Pat. No. 10,085,938, application No. 18/738,464 is a continuation of application No. 17/543,992, filed on Dec. 7, 2021, which is a continuation-in-part of application No. 16/804,361, filed on Feb. 28, 2020, now Pat. No. 11,191,665, which is a continuation-in-part of application No. 16/020,433, filed on Jun. 27, 2018, now Pat. No. 10,583,033, which is a continuation-in-part of application No. 15/342,642, filed on Nov. 3, 2016, now Pat. No. 10,010,568, application No. 18/738,464 is a continuation of application No. 16/776,861, filed on Jan. 30, 2020, now Pat. No. 10,864,109, which is a continuation of application No. 16/142,171, filed on Sep. 26, 2018, now Pat. No. 10,548,761, which is a continuation-in-part of application No. 15/395,419, filed on Dec. 30, 2016, now Pat. No. 10,086,018, application No. 18/738,464 is a continuation of application No. 16/426,346, filed on May 30, 2019, now Pat. No. 10,716,815, which is a continuation of application No. 15/639,767, filed on Jun. 30, 2017, now Pat. No. 10,314,865, which is a continuation-in-part of application No. 15/437,976, filed on Feb. 21, 2017, now Pat. No. 9,730,967, which is a continuation-in-part of application No. 15/228,454, filed on Aug. 4, 2016, now Pat. No. 9,585,920, application No. 18/738,464 is a continuation of application No. 15/270,034, filed on Sep. 20, 2016, now Pat. No. 9,750,802, which is a continuation-in-part of application No. 14/954,074, filed on Nov. 30, 2015, now Pat. No. 9,547,077, which is a continuation-in-part of application No. 14/574,517, filed on Dec. 18, 2014, now Pat. No. 9,408,880, application No. 18/738,464 is a continuation of application No. 16/037,053, filed on Jul. 17, 2018, now abandoned, and a continuation of application No. 14/752,192, filed on Jun. 26, 2015, now Pat. No. 9,549,842.

(60) Provisional application No. 63/649,793, filed on May 20, 2024, provisional application No. 62/275,341, filed on Jan. 6, 2016, provisional application No. 62/274,550, filed on Jan. 4, 2016, provisional application No. 62/387,404, filed on Dec. 24, 2015, provisional application No. 62/387,405, filed on Dec. 24, 2015, provisional application No. 62/260,906, filed on Nov. 30, 2015, provisional application No. 62/072,476, filed on Oct. 30, 2014, provisional application No. 62/053,926, filed on Sep. 23, 2014, provisional application No. 62/014,855, filed on Jun. 20, 2014, provisional application No. 61/919,297, filed on Dec. 20, 2013, provisional application No. 62/296,186, filed on Feb. 17, 2016.

(56) References Cited

U.S. PATENT DOCUMENTS

| | | |
|---|---|---|
| 3,640,741 A | 2/1972 | Etes |
| 3,832,460 A | 8/1974 | Kosti |
| 3,996,934 A | 12/1976 | Zaffaroni |
| 4,136,145 A | 1/1979 | Fuchs et al. |
| 4,136,162 A | 1/1979 | Fuchs et al. |
| 4,163,777 A | 8/1979 | Mitra |
| 4,226,848 A | 10/1980 | Nagai et al. |
| 4,250,163 A | 2/1981 | Nagai et al. |
| 4,285,934 A | 8/1981 | Tinnell |
| 4,286,592 A | 9/1981 | Chandrasekaran |
| 4,292,299 A | 9/1981 | Suzuki et al. |
| 4,381,296 A | 4/1983 | Tinnell |
| 4,517,173 A | 5/1985 | Kizawa et al. |
| 4,518,721 A | 5/1985 | Dhabhar et al. |
| 4,568,639 A | 2/1986 | Lew |
| 4,572,832 A | 2/1986 | Kigasawa et al. |
| 4,668,232 A | 5/1987 | Cordes et al. |
| 4,687,841 A | 8/1987 | Spilburg et al. |
| 4,713,243 A | 12/1987 | Schiraldi et al. |
| 4,715,369 A | 12/1987 | Susuki et al. |
| 4,720,486 A | 1/1988 | Spilburg et al. |
| 4,740,365 A | 4/1988 | Yukimatsu et al. |
| 4,765,983 A | 8/1988 | Takayanagi et al. |
| 4,830,008 A | 5/1989 | Meer |
| 4,849,246 A | 7/1989 | Schmidt |
| 4,867,970 A | 9/1989 | Newsham et al. |
| 4,889,720 A | 12/1989 | Konishi |
| 4,894,232 A | 1/1990 | Reul et al. |
| 4,900,554 A | 2/1990 | Yanagibashi et al. |
| 4,906,463 A | 3/1990 | Cleary et al. |
| 4,915,948 A | 4/1990 | Gallopo et al. |
| 4,937,078 A | 6/1990 | Mezei et al. |
| 4,995,555 A | 2/1991 | Woodruff |
| 5,002,970 A | 3/1991 | Eby, III |
| 5,059,189 A | 10/1991 | Cilento et al. |
| 5,064,654 A | 11/1991 | Berner et al. |

(56) References Cited

U.S. PATENT DOCUMENTS

| | | |
|---|---|---|
| 5,081,157 A | 1/1992 | Pomerantz |
| 5,081,158 A | 1/1992 | Pomerantz |
| 5,116,621 A | 5/1992 | Oji et al. |
| 5,137,729 A | 8/1992 | Kuroya et al. |
| 5,158,789 A | 10/1992 | DuRoss |
| 5,166,233 A | 11/1992 | Kuroya et al. |
| 5,190,053 A | 3/1993 | Meer |
| 5,192,802 A | 3/1993 | Rencher |
| 5,196,202 A | 3/1993 | Konishi |
| 5,277,877 A | 1/1994 | Jeffrey et al. |
| 5,284,161 A | 2/1994 | Karell |
| 5,298,258 A | 3/1994 | Akemi et al. |
| 5,314,915 A | 5/1994 | Rencher |
| 5,332,576 A | 7/1994 | Mantelle |
| 5,462,749 A | 10/1995 | Rencher |
| 5,465,734 A | 11/1995 | Alvarez et al. |
| 5,466,465 A | 11/1995 | Royds et al. |
| 5,505,956 A | 4/1996 | Kim et al. |
| 5,518,733 A | 5/1996 | Lamothe et al. |
| 5,578,315 A | 11/1996 | Chien et al. |
| 5,585,098 A | 12/1996 | Coleman |
| 5,614,501 A | 3/1997 | Richards |
| 5,629,003 A | 5/1997 | Horstmann et al. |
| 5,643,603 A | 7/1997 | Bottenberg et al. |
| 5,700,478 A | 12/1997 | Biegajski et al. |
| 5,713,852 A | 2/1998 | Anthony et al. |
| 5,718,702 A | 2/1998 | Edwards |
| 5,719,196 A | 2/1998 | Uhari et al. |
| 5,792,067 A | 8/1998 | Karell |
| 5,800,832 A | 9/1998 | Tapolsky et al. |
| 5,804,211 A | 9/1998 | Robertson et al. |
| 5,843,021 A | 12/1998 | Edwards et al. |
| 5,855,872 A | 1/1999 | Libin |
| 5,876,995 A | 3/1999 | Bryan |
| 5,895,804 A | 4/1999 | Lee et al. |
| 5,900,245 A | 5/1999 | Sawhney et al. |
| 5,948,430 A | 9/1999 | Zerbe et al. |
| 5,988,171 A | 11/1999 | Sohn et al. |
| 6,054,143 A | 4/2000 | Jones |
| 6,072,100 A | 6/2000 | Mooney et al. |
| 6,139,861 A | 10/2000 | Friedman |
| 6,161,541 A | 12/2000 | Woodson |
| 6,174,546 B1 | 1/2001 | Therriault et al. |
| 6,210,699 B1 | 4/2001 | Acharya et al. |
| 6,250,307 B1 | 6/2001 | Conrad et al. |
| 6,284,235 B1 | 9/2001 | Foreman et al. |
| 6,287,610 B1 | 9/2001 | Bowling et al. |
| 6,352,711 B1 | 3/2002 | Campbell |
| 6,375,963 B1 | 4/2002 | Repka et al. |
| 6,390,096 B1 | 5/2002 | Conrad et al. |
| 6,431,174 B1 | 8/2002 | Knudson et al. |
| 6,432,986 B2 | 8/2002 | Levin |
| 6,439,238 B1 | 8/2002 | Brenzel et al. |
| 6,453,905 B1 | 9/2002 | Conrad et al. |
| 6,458,380 B1 | 10/2002 | Leaderman |
| 6,458,777 B1 | 10/2002 | Sonis et al. |
| 6,467,485 B1 | 10/2002 | Schmidt |
| 6,502,574 B2 | 1/2003 | Stevens et al. |
| 6,509,028 B2 | 1/2003 | Williams et al. |
| 6,523,542 B2 | 2/2003 | Knudson et al. |
| 6,552,024 B1 | 4/2003 | Chen et al. |
| 6,555,125 B2 | 4/2003 | Campbell |
| 6,569,474 B2 | 5/2003 | Clayton et al. |
| 6,578,580 B2 | 6/2003 | Conrad et al. |
| 6,585,997 B2 | 7/2003 | Moro et al. |
| 6,599,883 B1 | 7/2003 | Romeo et al. |
| 6,620,846 B1 | 9/2003 | Jonn et al. |
| 6,713,463 B2 | 3/2004 | Sonis et al. |
| 6,722,577 B2 | 4/2004 | Dobyns, III |
| 6,726,920 B1 | 4/2004 | Theeuwes et al. |
| 6,734,157 B2 | 5/2004 | Radwanski et al. |
| 6,748,951 B1 | 6/2004 | Schmidt |
| 6,794,318 B2 | 9/2004 | Anderson et al. |
| 6,803,420 B2 | 10/2004 | Cleary et al. |
| 6,916,480 B2 | 7/2005 | Anderson et al. |
| 6,919,373 B1 | 7/2005 | Lam et al. |
| 6,923,981 B2 | 8/2005 | Leung et al. |
| 7,001,609 B1 | 2/2006 | Matson et al. |
| 7,067,116 B1 | 6/2006 | Bess et al. |
| 7,087,249 B2 | 8/2006 | Burrell et al. |
| 7,097,853 B1 | 8/2006 | Garbe et al. |
| 7,122,198 B1 | 10/2006 | Singh et al. |
| 7,138,135 B2 | 11/2006 | Chen et al. |
| 7,143,709 B2 | 12/2006 | Brennan et al. |
| 7,146,981 B2 | 12/2006 | Knudson et al. |
| 7,267,975 B2 | 9/2007 | Strobel et al. |
| 7,276,246 B2 | 10/2007 | Zhang |
| 7,287,646 B2 | 10/2007 | Gierskcky |
| 7,306,812 B2 | 12/2007 | Zhang |
| 7,332,230 B1 | 2/2008 | Krumme |
| 7,353,194 B1 | 4/2008 | Kerker et al. |
| 7,357,891 B2 | 4/2008 | Yang et al. |
| 7,425,292 B2 | 9/2008 | Yang et al. |
| 7,441,559 B2 | 10/2008 | Nelson et al. |
| 7,470,397 B2 | 12/2008 | Meathrel et al. |
| 7,500,484 B2 | 3/2009 | Nelson et al. |
| 7,540,432 B2 | 6/2009 | Majerowski et al. |
| 7,566,310 B2 | 7/2009 | Badr et al. |
| 7,575,739 B2 | 8/2009 | Tamarkin et al. |
| 7,579,019 B2 | 8/2009 | Tapolsky et al. |
| 7,579,078 B2 | 8/2009 | Hartmann et al. |
| 7,615,235 B2 | 11/2009 | Rademacher et al. |
| 7,632,525 B2 | 12/2009 | Dodds et al. |
| 7,645,803 B2 | 1/2010 | Tamarkin et al. |
| 7,648,712 B2 | 1/2010 | Bess et al. |
| 7,650,848 B2 | 1/2010 | Brennan et al. |
| 7,666,502 B2 | 2/2010 | Magill et al. |
| 7,669,603 B2 | 3/2010 | Knudson et al. |
| 7,686,021 B2 | 3/2010 | Knudson et al. |
| 7,704,518 B2 | 4/2010 | Tamarkin et al. |
| 7,727,466 B2 | 6/2010 | Meathrel et al. |
| 7,799,337 B2 | 9/2010 | Levin |
| 7,820,145 B2 | 10/2010 | Tamarkin et al. |
| 7,820,420 B2 | 10/2010 | Whitlock |
| 7,824,588 B2 | 11/2010 | Yang et al. |
| 7,824,704 B2 | 11/2010 | Anderson et al. |
| 7,845,356 B2 | 12/2010 | Paraschac et al. |
| 7,862,808 B2 | 1/2011 | Isolauri et al. |
| 7,901,925 B2 | 3/2011 | Bojrab |
| 7,906,140 B2 | 3/2011 | Bromley et al. |
| 7,937,159 B2 | 5/2011 | Lima et al. |
| 7,984,714 B2 | 7/2011 | Hausmann et al. |
| 7,992,566 B2 | 8/2011 | Pflueger et al. |
| 7,997,266 B2 | 8/2011 | Frazier et al. |
| 8,030,457 B2 | 10/2011 | Jackson et al. |
| 8,034,601 B2 | 10/2011 | Boileau et al. |
| 8,034,606 B2 | 10/2011 | Park et al. |
| 8,104,478 B2 | 1/2012 | Pflueger et al. |
| 8,110,215 B2 | 2/2012 | Koenig et al. |
| 8,197,872 B2 | 6/2012 | Mills et al. |
| 8,349,313 B2 | 1/2013 | Smith et al. |
| 8,357,368 B2 | 1/2013 | Dudek et al. |
| 8,362,206 B2 | 1/2013 | Wallach et al. |
| 8,383,201 B2 | 2/2013 | Berry et al. |
| 8,420,074 B2 | 4/2013 | Rehberger et al. |
| 8,454,729 B2 | 6/2013 | Mittelmark et al. |
| 8,481,299 B2 | 7/2013 | Gueniche et al. |
| 8,496,914 B2 | 7/2013 | Bonfiglio |
| 8,584,685 B2 | 11/2013 | Kovarik et al. |
| 8,585,588 B2 | 11/2013 | Kovarik et al. |
| 8,591,412 B2 | 11/2013 | Kovarik et al. |
| 8,657,879 B2 | 2/2014 | Shalon et al. |
| 8,685,389 B2 | 4/2014 | Baur et al. |
| 8,701,671 B2 | 4/2014 | Kovarik |
| 8,716,327 B2 | 5/2014 | Zhao et al. |
| 8,757,173 B2 | 6/2014 | Kovarik et al. |
| 8,758,764 B2 | 6/2014 | Masignani et al. |
| 8,815,538 B2 | 8/2014 | Lanzalaco et al. |
| 8,829,165 B2 | 9/2014 | Jackson et al. |
| 8,859,741 B2 | 10/2014 | Jackson et al. |
| 8,865,211 B2 | 10/2014 | Tzannis et al. |
| 8,936,030 B2 | 1/2015 | Kovarik et al. |
| 8,945,839 B2 | 2/2015 | Zhang et al. |
| 8,951,775 B2 | 2/2015 | Castiel et al. |

(56) References Cited

U.S. PATENT DOCUMENTS

| | | |
|---|---|---|
| 8,999,372 B2 | 4/2015 | Davidson et al. |
| 9,010,340 B2 | 4/2015 | Kovarik et al. |
| 9,011,834 B1 | 4/2015 | McKenzie et al. |
| 9,016,221 B2 | 4/2015 | Brennan et al. |
| 9,017,718 B2 | 4/2015 | Tan et al. |
| 9,028,841 B2 | 5/2015 | Henn et al. |
| 9,044,420 B2 | 6/2015 | Dubensky, Jr. |
| 9,045,547 B2 | 6/2015 | Jackson et al. |
| 9,056,912 B2 | 6/2015 | Grandi et al. |
| 9,095,704 B2 | 8/2015 | McGuire et al. |
| 9,131,884 B2 | 9/2015 | Holmes et al. |
| 9,149,429 B2 | 10/2015 | Kovacs et al. |
| 9,234,204 B2 | 1/2016 | Qvit-Raz et al. |
| 9,254,295 B2 | 2/2016 | Adams et al. |
| 9,288,981 B2 | 3/2016 | Gandhi et al. |
| 9,295,682 B2 | 3/2016 | Nunes et al. |
| 9,314,489 B2 | 4/2016 | Kelly et al. |
| 9,408,880 B2 | 8/2016 | Kovarik et al. |
| 9,445,936 B2 | 9/2016 | Kovarik |
| 9,457,077 B2 | 10/2016 | Kovarik et al. |
| 9,549,842 B2 | 1/2017 | Kovarik |
| 9,585,920 B2 | 3/2017 | Kovarik et al. |
| 9,730,967 B2 | 8/2017 | Kovarik et al. |
| 9,750,802 B2 | 9/2017 | Kovarik et al. |
| 9,795,641 B2 | 10/2017 | Nardelli et al. |
| 9,987,224 B2 | 6/2018 | Kovarik et al. |
| 10,085,938 B2 | 10/2018 | Kovarik et al. |
| 10,086,018 B2 | 10/2018 | Kovarik |
| 10,111,913 B2 | 10/2018 | Kovarik |
| 10,195,273 B2 | 2/2019 | Clube |
| 10,213,466 B2 | 2/2019 | Graf et al. |
| 10,245,288 B2 | 4/2019 | Kovarik |
| 10,314,865 B2 | 6/2019 | Kovarik |
| 10,314,866 B2 | 6/2019 | Kovarik |
| 10,512,661 B2 | 12/2019 | Kovarik |
| 10,548,761 B2 | 2/2020 | Kovarik |
| 10,555,976 B2 | 2/2020 | Kovarik |
| 10,668,014 B2 | 6/2020 | Kovarik et al. |
| 10,683,323 B2 | 6/2020 | Prakash et al. |
| 10,687,975 B2 | 6/2020 | Kovarik et al. |
| 10,716,815 B2 | 7/2020 | Kovarik et al. |
| 10,730,827 B2 | 8/2020 | Wortmann et al. |
| 10,760,075 B2 | 9/2020 | Sommer et al. |
| 10,835,560 B2 | 11/2020 | Kovarik |
| 10,842,834 B2 | 11/2020 | Kovarik |
| 10,864,109 B2 | 12/2020 | Kovarik |
| 10,940,169 B2 | 3/2021 | Kovarik et al. |
| 11,026,982 B2 | 6/2021 | Kovarik |
| 11,040,076 B2 | 6/2021 | Graf et al. |
| 11,083,760 B2 | 8/2021 | Han |
| 11,213,552 B2 | 1/2022 | Kovarik |
| 11,235,060 B2 | 2/2022 | Graf et al. |
| 11,273,187 B2 | 3/2022 | Kovarik |
| 11,357,722 B2 | 6/2022 | Kovarik et al. |
| 11,419,903 B2 | 8/2022 | Kovarik |
| 11,523,934 B2 | 12/2022 | Kovarik et al. |
| 11,529,379 B2 | 12/2022 | Kovarik |
| 11,642,382 B2 | 5/2023 | Kovarik |
| 11,672,835 B2 | 6/2023 | Kovarik |
| 11,826,388 B2 | 11/2023 | Kovarik |
| 11,833,177 B2 | 12/2023 | Simmons et al. |
| 11,839,632 B2 | 12/2023 | Tye et al. |
| 11,844,720 B2 | 12/2023 | Tye et al. |
| 11,951,139 B2 | 4/2024 | Kovarik |
| 11,951,140 B2 | 4/2024 | Kovarik |
| 11,969,445 B2 | 4/2024 | Kovarik |
| 11,980,643 B2 | 5/2024 | Simmons et al. |
| 11,998,479 B2 | 6/2024 | Simmons et al. |
| 11,998,574 B2 | 6/2024 | Simmons et al. |
| 12,005,085 B2 | 6/2024 | Simmons et al. |
| 2002/0009429 A1 | 1/2002 | Bostwick |
| 2002/0009520 A1 | 1/2002 | Clayton et al. |
| 2002/0022057 A1 | 2/2002 | Battey et al. |
| 2002/0037310 A1 | 3/2002 | Jonn et al. |
| 2002/0044988 A1 | 4/2002 | Fuchs et al. |
| 2003/0031737 A1 | 2/2003 | Rosenbloom |
| 2003/0062050 A1 | 4/2003 | Schmidt |
| 2003/0083287 A1 | 5/2003 | Burgess et al. |
| 2003/0104041 A1 | 6/2003 | Hsu et al. |
| 2003/0106243 A1 | 6/2003 | Tucker |
| 2003/0124178 A1 | 7/2003 | Haley |
| 2003/0140930 A1 | 7/2003 | Knudson et al. |
| 2003/0149387 A1 | 8/2003 | Barakat et al. |
| 2003/0149445 A1 | 8/2003 | Knudson et al. |
| 2003/0206995 A1 | 11/2003 | Bowling et al. |
| 2004/0053352 A1 | 3/2004 | Ouyang et al. |
| 2004/0057962 A1 | 3/2004 | Timmerman |
| 2004/0062757 A1 | 4/2004 | Finegold |
| 2004/0096569 A1 | 5/2004 | Barkalow et al. |
| 2004/0110111 A1 | 6/2004 | Wasylucha |
| 2004/0115223 A1 | 6/2004 | Follansbee |
| 2004/0120991 A1 | 6/2004 | Gardner et al. |
| 2004/0136923 A1 | 7/2004 | Davidson et al. |
| 2004/0142463 A1 | 7/2004 | Walker et al. |
| 2004/0166501 A1 | 8/2004 | Azimzai et al. |
| 2004/0170617 A1 | 9/2004 | Finegold |
| 2004/0180080 A1 | 9/2004 | Furasawa et al. |
| 2004/0224007 A1 | 11/2004 | Zhang |
| 2004/0228804 A1 | 11/2004 | Jones et al. |
| 2005/0004417 A1 | 1/2005 | Nelson et al. |
| 2005/0159637 A9 | 1/2005 | Nelson et al. |
| 2005/0118655 A1 | 6/2005 | Weinstock et al. |
| 2005/0137109 A1 | 6/2005 | Quan et al. |
| 2005/0196358 A1 | 9/2005 | Georgiades et al. |
| 2005/0197495 A1 | 9/2005 | Naidu |
| 2005/0260544 A1 | 11/2005 | Jones et al. |
| 2006/0018843 A1 | 1/2006 | Fine |
| 2006/0035008 A1 | 2/2006 | Virgallito et al. |
| 2006/0064903 A1 | 3/2006 | Tucker |
| 2006/0127330 A1 | 6/2006 | Tsuchida et al. |
| 2006/0188813 A1 | 8/2006 | Shimada |
| 2006/0204591 A1 | 9/2006 | Burrel et al. |
| 2006/0207721 A1 | 9/2006 | Slominski et al. |
| 2006/0252087 A1 | 11/2006 | Tang et al. |
| 2007/0054008 A1 | 3/2007 | Clayton et al. |
| 2007/0057086 A1 | 3/2007 | Van Kippersluis et al. |
| 2007/0059718 A1 | 3/2007 | Toner et al. |
| 2007/0059774 A1 | 3/2007 | Grisham et al. |
| 2007/0063026 A1 | 3/2007 | Mamaropolos et al. |
| 2007/0087020 A1 | 4/2007 | O'Connor |
| 2007/0093420 A1 | 4/2007 | Yeomans et al. |
| 2007/0098744 A1 | 5/2007 | Knorr et al. |
| 2007/0102010 A1 | 5/2007 | Lemperle et al. |
| 2007/0122455 A1 | 5/2007 | Myers et al. |
| 2007/0123448 A1 | 5/2007 | Kaplan et al. |
| 2007/0148136 A1 | 6/2007 | Whitlock |
| 2007/0202057 A1 | 8/2007 | Fankhauser et al. |
| 2007/0207955 A1 | 9/2007 | Tanihara et al. |
| 2007/0218114 A1 | 9/2007 | Duggan |
| 2007/0227545 A1 | 10/2007 | Conrad et al. |
| 2007/0231923 A1 | 10/2007 | Cumberland et al. |
| 2007/0246052 A1 | 10/2007 | Hegde et al. |
| 2007/0261701 A1 | 11/2007 | Sanders |
| 2007/0280964 A1 | 12/2007 | Knorr et al. |
| 2007/0293587 A1 | 12/2007 | Haley |
| 2007/0295340 A1 | 12/2007 | Buscemi |
| 2008/0032253 A1 | 2/2008 | Montgomery et al. |
| 2008/0075825 A1 | 3/2008 | Fuisz et al. |
| 2008/0112983 A1 | 5/2008 | Bufe et al. |
| 2008/0242543 A1 | 10/2008 | Banerjee et al. |
| 2008/0267933 A1 | 10/2008 | Ohlson et al. |
| 2008/0286210 A1 | 11/2008 | He et al. |
| 2008/0305089 A1 | 12/2008 | Bufe et al. |
| 2009/0004275 A1 | 1/2009 | Martyn et al. |
| 2009/0098192 A1 | 4/2009 | Fuisz |
| 2009/0130199 A1 | 5/2009 | Kovacs et al. |
| 2009/0148482 A1 | 6/2009 | Peters |
| 2009/0196907 A1 | 8/2009 | Bunick et al. |
| 2009/0196908 A1 | 8/2009 | Lee et al. |
| 2009/0205083 A1 | 8/2009 | Gupta et al. |
| 2010/0029832 A1 | 2/2010 | Pinnavala et al. |
| 2010/0040593 A1 | 2/2010 | Hedman et al. |
| 2010/0040712 A1 | 2/2010 | Fisher |
| 2010/0081681 A1 | 4/2010 | Blagosklonny |

(56) References Cited

U.S. PATENT DOCUMENTS

| | | |
|---|---|---|
| 2010/0092406 A1 | 4/2010 | Perez-Davidi et al. |
| 2010/0124560 A1 | 5/2010 | Hugerth et al. |
| 2010/0143447 A1 | 6/2010 | Hansen et al. |
| 2010/0229876 A1 | 9/2010 | Knudson et al. |
| 2010/0247644 A1 | 9/2010 | Domb et al. |
| 2010/0260720 A1 | 10/2010 | Sprenger |
| 2010/0285098 A1 | 11/2010 | Haley |
| 2011/0009834 A1 | 1/2011 | Asmussen et al. |
| 2011/0033542 A1 | 2/2011 | Myers et al. |
| 2011/0088701 A1 | 4/2011 | Thornton |
| 2011/0100378 A1 | 5/2011 | Rousseau |
| 2011/0142942 A1 | 6/2011 | Schobel et al. |
| 2011/0217368 A1 | 9/2011 | Prakash et al. |
| 2011/0230587 A1 | 9/2011 | MacInnis et al. |
| 2011/0230727 A1 | 9/2011 | Sanders et al. |
| 2011/0250626 A1 | 10/2011 | Williams et al. |
| 2011/0274795 A1 | 11/2011 | Bogue et al. |
| 2011/0290694 A1 | 12/2011 | Fuisz et al. |
| 2012/0027786 A1 | 2/2012 | Gupta et al. |
| 2012/0029832 A1 | 2/2012 | Dodgson |
| 2012/0039806 A1 | 2/2012 | Lahoud et al. |
| 2012/0058094 A1 | 3/2012 | Blaser et al. |
| 2012/0128597 A1 | 5/2012 | Peters et al. |
| 2012/0142548 A1 | 6/2012 | Corsi et al. |
| 2012/0148629 A1 | 6/2012 | Holvoet et al. |
| 2012/0276143 A1 | 11/2012 | O'Mahony et al. |
| 2012/0276149 A1 | 11/2012 | Littman et al. |
| 2012/0276525 A1 | 11/2012 | Kovarik et al. |
| 2012/0283269 A1 | 11/2012 | Blagosklonny et al. |
| 2012/0294822 A1 | 11/2012 | Russo et al. |
| 2012/0301452 A1 | 11/2012 | Gueniche et al. |
| 2013/0059815 A1 | 3/2013 | Fournell et al. |
| 2013/0087155 A1 | 4/2013 | Hedman et al. |
| 2013/0157876 A1 | 6/2013 | Lynch et al. |
| 2013/0225440 A1 | 8/2013 | Friedman et al. |
| 2013/0236488 A1 | 9/2013 | Dashper et al. |
| 2013/0252983 A1 | 9/2013 | Cerione et al. |
| 2013/0259834 A1 | 10/2013 | Klaenhammer et al. |
| 2013/0310416 A1 | 11/2013 | Blagosklonny |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0326645 A1 | 12/2013 | Cost et al. |
| 2013/0330215 A1 | 12/2013 | Li |
| 2014/0030332 A1 | 1/2014 | Baron et al. |
| 2014/0044677 A1 | 2/2014 | Qvit-Raz et al. |
| 2014/0045744 A1 | 2/2014 | Gordon et al. |
| 2014/0065209 A1 | 3/2014 | Putaala et al. |
| 2014/0065218 A1 | 3/2014 | Lang et al. |
| 2014/0066817 A1 | 3/2014 | Kovarik et al. |
| 2014/0068797 A1 | 3/2014 | Doudna et al. |
| 2014/0125550 A1 | 5/2014 | Kaneko et al. |
| 2014/0154290 A1 | 6/2014 | Peters et al. |
| 2014/0199266 A1 | 7/2014 | Park et al. |
| 2014/0255351 A1 | 9/2014 | Berstad et al. |
| 2014/0271867 A1 | 9/2014 | Myers et al. |
| 2014/0294915 A1 | 10/2014 | Barreca et al. |
| 2014/0296139 A1 | 10/2014 | Cohen et al. |
| 2014/0333003 A1 | 11/2014 | Allen et al. |
| 2014/0349405 A1 | 11/2014 | Sontheimer et al. |
| 2014/0356460 A1 | 12/2014 | Lutin |
| 2014/0363441 A1 | 12/2014 | Grandea, III et al. |
| 2014/0364460 A1 | 12/2014 | Freed-Pastor et al. |
| 2014/0377278 A1 | 12/2014 | Elinav et al. |
| 2015/0004130 A1 | 1/2015 | Faber et al. |
| 2015/0017143 A1 | 1/2015 | Holvoet et al. |
| 2015/0017227 A1 | 1/2015 | Kim et al. |
| 2015/0038594 A1 | 2/2015 | Borges et al. |
| 2015/0045546 A1 | 2/2015 | Siksnys et al. |
| 2015/0064138 A1 | 3/2015 | Lu et al. |
| 2015/0071957 A1 | 3/2015 | Kelly et al. |
| 2015/0086581 A1 | 3/2015 | Li et al. |
| 2015/0093473 A1 | 4/2015 | Barrangou et al. |
| 2015/0132263 A1 | 5/2015 | Liu et al. |
| 2015/0147371 A1 | 5/2015 | Kovarik et al. |
| 2015/0150792 A1 | 6/2015 | Klingman |
| 2015/0166641 A1 | 6/2015 | Goodman et al. |
| 2015/0190435 A1 | 7/2015 | Henn et al. |
| 2015/0190438 A1 * | 7/2015 | Nivoliez ............... A61K 9/0036 435/252.9 |
| 2015/0202136 A1 | 7/2015 | Lanzalaco et al. |
| 2015/0216917 A1 | 8/2015 | Jones et al. |
| 2015/0224072 A1 | 8/2015 | Pellikaan |
| 2015/0252358 A1 | 9/2015 | Maeder et al. |
| 2015/0259728 A1 | 9/2015 | Cutliffe et al. |
| 2015/0329555 A1 | 11/2015 | Liras et al. |
| 2015/0329875 A1 | 11/2015 | Gregory et al. |
| 2015/0352023 A1 | 12/2015 | Berg et al. |
| 2015/0353901 A1 | 12/2015 | Liu et al. |
| 2015/0361436 A1 | 12/2015 | Hitchcock et al. |
| 2015/0374607 A1 | 12/2015 | Lanzalaco et al. |
| 2016/0000754 A1 | 1/2016 | Stamets |
| 2016/0000841 A1 | 1/2016 | Yamamoto et al. |
| 2016/0008412 A1 | 1/2016 | Putaala et al. |
| 2016/0024510 A1 | 1/2016 | Bikard et al. |
| 2016/0040216 A1 | 2/2016 | Akins et al. |
| 2016/0069921 A1 | 3/2016 | Holmes et al. |
| 2016/0089315 A1 | 3/2016 | Kleinberg et al. |
| 2016/0089405 A1 | 3/2016 | Lue |
| 2016/0095316 A1 | 4/2016 | Goodman et al. |
| 2016/0120915 A1 | 5/2016 | Blaser et al. |
| 2016/0122806 A1 | 5/2016 | Amini et al. |
| 2016/0151427 A1 | 6/2016 | Whitlock et al. |
| 2016/0151428 A1 | 6/2016 | Bryan |
| 2016/0158294 A1 | 6/2016 | Von Maltzahn et al. |
| 2016/0168594 A1 | 6/2016 | Zhang et al. |
| 2016/0175327 A1 | 6/2016 | Adams et al. |
| 2016/0199424 A1 | 7/2016 | Berry et al. |
| 2016/0206564 A1 | 7/2016 | Trachtman |
| 2016/0206666 A1 | 7/2016 | Falb et al. |
| 2016/0206668 A1 | 7/2016 | Kort et al. |
| 2016/0213702 A1 | 7/2016 | Von Maltzahn et al. |
| 2016/0243132 A1 | 8/2016 | Adams et al. |
| 2016/0271106 A1 | 9/2016 | Shi et al. |
| 2016/0271189 A1 | 9/2016 | Cutcliffe et al. |
| 2016/0311913 A1 | 10/2016 | Sun et al. |
| 2016/0314281 A1 | 10/2016 | Apte et al. |
| 2016/0354416 A1 | 12/2016 | Gajewski et al. |
| 2016/0374941 A1 | 12/2016 | Barreca et al. |
| 2017/0014341 A1 | 1/2017 | Armer et al. |
| 2017/0020932 A1 | 1/2017 | Cutcliffe et al. |
| 2017/0027914 A1 | 2/2017 | Qi |
| 2017/0042860 A1 | 2/2017 | Kashyap et al. |
| 2017/0042924 A1 | 2/2017 | Otsuka et al. |
| 2017/0071986 A1 | 3/2017 | Kovarik et al. |
| 2017/0079947 A1 | 3/2017 | Richards |
| 2017/0100328 A1 | 4/2017 | Kovarik et al. |
| 2017/0232043 A1 | 8/2017 | Falb et al. |
| 2017/0240625 A1 | 8/2017 | Zeller et al. |
| 2017/0246269 A1 | 8/2017 | Hajishengallis et al. |
| 2017/0298115 A1 | 10/2017 | Loomis et al. |
| 2017/0312232 A1 | 11/2017 | Vitetta et al. |
| 2017/0342141 A1 | 11/2017 | Russo et al. |
| 2017/0348303 A1 | 12/2017 | Bosse et al. |
| 2018/0000878 A1 | 1/2018 | Goodman et al. |
| 2018/0015131 A1 | 1/2018 | Gajewski et al. |
| 2018/0016647 A1 | 1/2018 | Van Sinderen et al. |
| 2018/0092899 A1 | 4/2018 | Liu et al. |
| 2018/0100169 A1 | 4/2018 | Soucaille et al. |
| 2018/0110795 A1 | 4/2018 | Frias-Lopez |
| 2018/0111984 A1 | 5/2018 | Bigal et al. |
| 2018/0127490 A1 | 5/2018 | Bigal et al. |
| 2018/0134772 A1 | 5/2018 | Sharma et al. |
| 2018/0140698 A1 | 5/2018 | Clube et al. |
| 2018/0207165 A1 | 7/2018 | Harmsen et al. |
| 2018/0235987 A1 | 8/2018 | Von Maltzahn et al. |
| 2018/0258100 A1 | 9/2018 | Gregory et al. |
| 2018/0296582 A1 | 10/2018 | von Maltzahn et al. |
| 2018/0303658 A1 | 10/2018 | Kovarik et al. |
| 2018/0312851 A1 | 11/2018 | Falb et al. |
| 2018/0326008 A1 | 11/2018 | Schreiber et al. |
| 2018/0371405 A1 | 12/2018 | Barrangou et al. |
| 2019/0000815 A1 | 1/2019 | Melin |
| 2019/0018012 A1 | 1/2019 | Kovarik |

(56) References Cited

U.S. PATENT DOCUMENTS

| | | |
|---|---|---|
| 2019/0059314 A1 | 2/2019 | Aharoni et al. |
| 2019/0290605 A1 | 6/2019 | Rasochova et al. |
| 2019/0120960 A1 | 7/2019 | Konradi et al. |
| 2019/0262298 A1 | 8/2019 | Kanthasamy et al. |
| 2019/0315642 A1 | 10/2019 | Parsley et al. |
| 2019/0388471 A1 | 12/2019 | June et al. |
| 2019/0390284 A1 | 12/2019 | Kim |
| 2020/0009185 A1 | 1/2020 | Shin et al. |
| 2020/0009268 A1 | 1/2020 | Scholz |
| 2020/0032224 A1 | 1/2020 | Schaefer et al. |
| 2020/0148642 A1 | 5/2020 | Konradi et al. |
| 2020/0155447 A1 | 5/2020 | Edwards |
| 2020/0188454 A1 | 6/2020 | Slykerman |
| 2020/0190494 A1 | 6/2020 | Hou et al. |
| 2020/0197215 A1 | 6/2020 | Kovarik et al. |
| 2020/0199555 A1 | 6/2020 | Zhang |
| 2021/0169954 A1 | 6/2021 | Balani et al. |
| 2021/0198665 A1 | 7/2021 | Sommer et al. |
| 2021/0308028 A1 | 10/2021 | Yang et al. |
| 2021/0321756 A1 | 10/2021 | McLaughlin et al. |
| 2021/0361560 A1 | 11/2021 | Krueger et al. |
| 2021/0386659 A1 | 12/2021 | Kim |
| 2022/0000760 A1 | 1/2022 | Rasochova |
| 2022/0023259 A1 | 1/2022 | Davidson et al. |
| 2022/0031590 A1 | 2/2022 | Pesaro et al. |
| 2022/0031767 A1 | 2/2022 | Duportet et al. |
| 2022/0071877 A1 | 3/2022 | Zenobia et al. |
| 2022/0088001 A1 | 3/2022 | Kovarik et al. |
| 2022/0088090 A1 | 3/2022 | Lobacki et al. |
| 2022/0118031 A1 | 4/2022 | Kovarik |
| 2022/0135987 A1 | 5/2022 | Leveau et al. |
| 2022/0193150 A1 | 6/2022 | Kovarik |
| 2022/0193157 A1 | 6/2022 | Zimmerman et al. |
| 2022/0257410 A1 | 8/2022 | Kovarik |
| 2022/0296500 A1 | 9/2022 | Kovarik |
| 2022/0331374 A1 | 10/2022 | Richter et al. |
| 2022/0339208 A1 | 10/2022 | Abel et al. |
| 2022/0387402 A1 | 12/2022 | Aspnes et al. |
| 2023/0106721 A1 | 4/2023 | Catania et al. |
| 2024/0156878 A1 | 5/2024 | Jensen et al. |
| 2024/0277780 A1 | 8/2024 | Jensen et al. |
| 2024/0285697 A1 | 8/2024 | Simmons et al. |

FOREIGN PATENT DOCUMENTS

| | | |
|---|---|---|
| JP | S56-100714 | 8/1981 |
| WO | WO 98/22097 | 5/1998 |
| WO | WO 2006/007922 | 1/2006 |
| WO | WO 2006/015445 | 2/2006 |
| WO | WO 2006/133879 | 12/2006 |
| WO | WO 2008/088426 | 7/2008 |
| WO | WO 2008/097890 | 8/2008 |
| WO | WO 2009/052421 | 4/2009 |
| WO | WO 2010/041143 | 4/2010 |
| WO | WO 2011/020780 | 2/2011 |
| WO | WO 2011/029701 | 3/2011 |
| WO | WO 2013/026000 | 2/2013 |
| WO | WO 2013/107750 | 7/2013 |
| WO | WO 2013/182038 | 12/2013 |
| WO | WO 2014/103488 | 7/2014 |
| WO | WO 2014/152338 | 9/2014 |
| WO | WO 2014/182632 | 11/2014 |
| WO | WO 2014/196913 | 12/2014 |
| WO | WO 2015/069682 | 5/2015 |
| WO | WO 2016/066763 | 5/2016 |
| WO | WO 2016/070151 | 5/2016 |
| WO | WO 2017/211753 | 12/2017 |
| WO | WO 2019/018348 | 1/2019 |
| WO | WO 2019/067621 | 4/2019 |
| WO | WO 2022/185121 | 9/2022 |
| WO | WO 2022/187274 | 9/2022 |

OTHER PUBLICATIONS

"Oral Cavity," University of Michigan Medical School, Date Unknown, retrieved Nov. 20, 2019 from https://histology.medicine.umich.edu/resources/oral-cavity, 5 pages.

"Poster Session I—IV Abstracts," American Society for Microbiology Conference on Biofilms, Nov. 13-17, 2022, Charlotte, NC, 226 pages.

"The structure behind the simplicity of CRISPR/Cas9," The Scinder at Medium.com, Dec. 23, 2015, retrieved from https://medium.com/the-scinder/the-structure-behind-the-simplicity-of-crispr-cas9-6f8cb60695c4, 8 pages.

Abruzzo et al., "Influence of Lactobacillus Biosurfactants on Skin Permeation of Hydrocortisone," Pharmaceutics, vol. 13, No. 6, May 2021, 14 pages.

Agrawal et al., "Technique to Control pH in Vicinity of Biodegrading PLA-PGA Implants," Journal of Biomedical Materials Research, vol. 38, No. 2, 1997, pp. 105-114.

Aguilar-Toala et al., "Potential role of natural bioactive peptides for development of cosmeceutical skin products," Peptides, vol. 122, No. 170170, Dec. 2019, 8 pages. Abstract only.

Athanasiou et al., "In Vitro Degradation and Release Characteristics of Biodegradable Implants Containing Trypsin Inhibitor," Clinical Orthopaedics and Related Research, vol. 315, Jun. 1995, pp. 272-281. Abstract only.

Auerbach et al., "Angiogenesis assays: Problems and pitfalls," Cancer and Metastasis Reviews, vol. 19, 2000, pp. 167-172.

Basseri et al., "Antibiotics for the Treatment of Irritable Bowel Syndrome," Gastroenterology & Hepatology, vol. 7, No. 7, Jul. 2011, pp. 455-493.

Baud et al., "Microbial diversity in the vaginal microbiota and its link to pregnancy outcomes," Scientific Reports, vol. 13, No. 9061, 2023, 12 pages.

Blumen et al., "Radiofrequency Ablation for the Treatment of Mild to Moderate Obstructive Sleep Apnea," The Laryngoscope, vol. 112, No. 11, Nov. 2002, pp. 2086-2092.

Bocheva et al., "Protective Role of Melatonin and Its Metabolites in Skin Aging," International Journal of Molecular Sciences, vol. 23, No. 1238, Jan. 2022, 23 pages.

Brietzke et al., "Injection Snoreplasty: Extended Follow-Up and New Objective Data," Otolaryngology—Head and Neck Surgery, vol. 128, No. 5, May 2003, pp. 605-615. Abstract only.

Brietzke et al., "Injection Snoreplasty: How to Treat Snoring without All the Pain and Expense," Otolaryngology—Head and Neck Surgery, vol. 124, No. 5, May 2001, pp. 503-510. Abstract only.

Brietzke et al., "Injection Snoreplasty: Investigation of Alternative Sclerotherapy Agents," Otolaryngology—Head and Neck Surgery, vol. 130, No. 1, Jan. 2004, pp. 47-57. Abstract only.

Brown et al., "Improving the Diagnosis of Vulvovaginitis: Perspectives to Align Practice, Guidelines, and Awareness," Population Health Management, vol. 23, Suppl. 1, 2020, pp. S3-S12.

Catalano et al., "Additional palatal implants for refractory snoring," Otolaryngology—Head and Neck Surgery, vol. 137, No. 1, Jul. 2007, pp. 105-109. Abstract only.

Charulatha et al., "Influence of different crosslinking treatments on the physical properties of collagen membranes," Biomaterials, vol. 24, No. 5, 2003, pp. 759-767.

Chen et al., "Targeting Aldehyde Dehydrogenase 2: New Therapeutic Opportunities," Physiological Reviews, vol. 94, No. 1, 2014, 65 pages.

Choi et al., "Therapeutic Effects of Cold-Pressed Perilla Oil Mainly Consisting of Linolenic acid, Oleic Acid and Linoleic Acid on UV-Induced Photoaging in NHDF Cells and SKH-1 Hairless Mice," Molecules, vol. 25, Feb. 2020, 19 pages.

Chuang et al., "Effects of exogenous crosslinking on in vitro tensile and compressive moduli of lumbar intervertebral discs," Clinical Biomechanics, vol. 22, No. 1, Jan. 2007, pp. 14-20. Abstract only.

Courage, "Fiber-Famished Gut Microbes Linked to Poor Health," Scientific American, Mar. 23, 2015, retrieved from https://www.scientificamerican.com/article/fiber-famished-gut-microbes-linked-to-poor-health, 10 pages.

(56) References Cited

OTHER PUBLICATIONS

De Seta et al., "The Vaginal Community State Types Microbiome-Immune Network as Key Factor for Bacterial Vaginosis and Aerobic Vaginitis," Frontiers in Microbiology, vol. 10, No. 2451, Oct. 30, 2019, 8 pages.
Ding et al., "Resveratrol accelerates wound healing by inducing M2 macrophage polarisation in diabetic mice," Pharmaceutical Biology, vol. 60, No. 1, 2022, pp. 2328-2337.
Douam et al., "Genetic Dissection of the Host Tropism of Human-Tropic Pathogens," Annual Review of Genetics, vol. 49, 2015, pp. 21-45.
Dunkley et al., "A role for CD4+ T cells from orally immunized rats in enhanced clearance of Pseudomonas aeruginosa from the lung," Immunology, vol. 83, 1994, pp. 362-369.
Earlia et al., "GC/MS Analysis of Fatty Acids on Pliek U Oil and Its Pharmacological Study by Molecular Docking to Filaggrin as a Drug Candidate in Atopic Dermatitis Treatment," Scientific World Journal, Nov. 2019, 7 pages.
Enomoto et al., "Koji amazake Maintains Water Content in the Left Cheek Skin of Healthy Adults: A Randomized, Double-Blind, Placebo-Controlled, Parallel-Group, Comparative Trial," Clinical, Cosmetic and Investigational Dermatology, vol. 15, Jul. 2022, pp. 1283-1291.
Farhadihosseinabadi et al., "The in vivo effect of Lacto-N-neotetraose (LNnT) on the expression of type 2 immune response involved genes in the wound healing process," Scientific Reports, vol. 10, No. 997, Jan. 2020, 11 pages.
Fischer et al., "[Radiofrequency ablation of the soft palate (somnoplasty). A new method in the treatment of habitual and obstructive snoring].," HNO, vol. 48, No. 1, Jan. 2000, pp. 33-40. Abstract only.
Frey, "Why to avoid toothpastes with sodium lauryl sulfate," Hatcher & Frey Orthodontics, Nov. 6, 2012, retrieved from https://smile-365.com/why-to-avoid-toothpastes-with-sodium-lauryl-sulfate/, 5 pages.
Friedman et al., "Patient Selection and Efficacy of Pillar Implant Technique for Treatment of Snoring and Obstructive Sleep Apnea/Hypopnea Syndrome," Otolaryngology—Head and Neck Surgery, vol. 134, No. 2, Feb. 2006, pp. 187-196. Abstract only.
Gajer et al., "Temporal Dynamics of the Human Vaginal Microbiota," Science Translational Medicine, vol. 4, No. 132, May 2, 2012, 21 pages.
Gratzer et al., "Control of pH Alters the Type of Cross-linking Produced by 1-Ethyl-3-(3-Dimethylaminopropyl)-Carbodiimide (EDC) Treatment of Acellular Matrix Vascular Grafts," Journal of Biomedical Materials Research, vol. 58, No. 2, 2001, pp. 172-179.
Guilleminault et al., "Snoring (I). Daytime sleepiness in regular heavy snorers," Chest, vol. 99, 1991, pp. 40-48.
Guilleminault et al., "The sleep apnea syndromes," Annual Review of Medicine, vol. 27, Feb. 1976, pp. 465-484. First Page Only.
Gura, "Systems for Identifying New Drugs Are Often Faulty," Science, vol. 278, No. 5340, Nov. 7, 1997, pp. 1041-1042.
Han et al., "Proanthocyanidin: A natural crosslinking reagent for stabilizing collagen matrices," Journal of Biomedical Materials Research, vol. 65A, No. 1, Apr. 2003, pp. 118-124. Abstract only.
Hedman et al., "Exogenous Cross-Linking Increases the Stability of Spinal Motion Segments," Spine, vol. 31, No. 15, Jul. 2006, pp. E480-E485. Abstract only.
Hennessy et al., "Statins as next generation anti-microbials: Is there potential for repurposing?," Antimicrob. Agents Chemother., Jun. 20, 2016, 46 pages.
Hildebrand et al., "Vaginitis," NCBI Bookshelf, Updated Nov. 14, 2022, 12 pages.
Hoffmann et al., "Glutaraldehyde and oxidised dextran as crosslinker reagents for chitosan-based scaffolds for cartilage tissue engineering," Journal of Materials Science: Materials in Medicine, vol. 20, Mar. 2009, pp. 1495-1503.
Hunter et al., "Meniscal material properties are minimally affected by matrix stabilization using glutaraldehyde and glycation with ribose," Journal of Orthopaedic Research, vol. 23, 2005, pp. 555-561.
Jain, "Barriers to Drug Delivery in Solid Tumors," Scientific American, Jul. 1994, pp. 58-65.
Kilkkinen et al., "Use of antimicrobials and risk of type 1 diabetes in a population-based mother-child cohort," Diabetologia, vol. 49, 2006, pp. 66-70.
Kim et al., "Kaempferol tetrasaccharides restore skin atrophy via PDK1 inhibition in human skin cells and tissues: Bench and clinical studies," Biomedicine & Pharmacotherapy, vol. 156, No. 113864, Dec. 2022, 13 pages.
Kim et al., "Spermidine-induced recovery of human dermal structure and barrier function by skin microbiome," Communications Biology, vol. 4, No. 231, 2021, 11 pages.
Kim et al., "β-Glucogallin isolated from Fusidium coccineum and its enhancement of skin barrier effects," Applied Biological Chemistry, vol. 63, No. 77, Nov. 2020, 7 pages.
Kimoto et al., "New Lactococcus Strain with Immunnomodulatory Activity: Enhancement of Th1-Type Immune Response," Microbiol. Immunol., vol. 48, No. 2, 2004, pp. 75-82.
Klapperich et al., "A novel biocompatible adhesive incorporating plant-derived monomers," Journal of Biomedical Materials Research Part A, vol. 91, No. 2, pp. 378-374.
Klingspor et al., "Research Article: Enterococcus faecium NCIMB 10415 Modulates Epithelial Integrity, Heat Shock Protein, and Proinflammatory Cytokine Response in Intestinal Cells," Mediators of Inflammation, vol. 2015, No. 304149, 2015, 12 pages.
Ko, "Effects of Glycogen on Ceramide Production in Cultured Human Keratinocytes via Acid Sphingomyelinase Activation," Master's Thesis Submitted to the Graduate School of Public Health (Korea), 2018, 53 pages.
Komuro et al., "Sphingomyelin maintains the cutaneous barrier via regulation of the STAT3 pathway," The FASEB Journal, vol. 36, No. 4, Apr. 2022, 17 pages.
Kurek-Gorecka et al., "Bee Products in Dermatology and Skin Care," Molecules, vol. 25, No. 3, Jan. 2020, 17 pages.
Kyriakopoulos et al., "Taurine and N-Bromotaurine in Topical Treatment of Psoriasis," Advances in Experimental Medicine and Biology, vol. 1370, 2022, pp. 99-111. Abstract only.
Laneri et al., "Plant cell culture extract of Cirsium eriophorum with skin pore refiner activity by modulating sebum production and inflammatory response," Phytotherapy Research, vol. 35, No. 1, Jan. 2021, pp. 530-540.
Lebeer et al., "Selective targeting of skin pathobionts and inflammation with topically applied lactobacilli," Cell Reports Medicine, vol. 3, No. 2, Feb. 2022, 22 pages.
Lenger et al., "D-mannose vs other agents for recurrent urinary tract infection prevention in adult women: a systematic review and meta-analysis," American Journal of Obstetrics and Gynecology, vol. 223, No. 2, Aug. 2020, pp. 265.e1-265.e13.
Lew et al., "Bioactives from probiotics for dermal health: functions and benefits," Journal of Applied Microbiology, vol. 114, No. 5, May 2013, pp. 1241-1253.
Lewis et al., "Vaginal Microbiome and Its Relationship to Behavior, Sexual Health, and Sexually Transmitted Diseases," Obstetrics & Gynecology, vol. 129, No. 4, Apr. 2017, pp. 643-654.
Liu et al., "Activation of aryl hydrocarbon receptor in Langerhans cells by a microbial metabolite of tryptophan negatively regulates skin inflammation," Journal of Dermatological Science, vol. 100, No. 3, Dec. 2020, pp. 192-200. Abstract only.
Liu et al., "The potential of Streptococcus thermophiles (TC1633) in the anti-aging," Journal of Cosmetic Dermatology, vol. 21, No. 6, Jun. 2022, pp. 2635-2647.
Ma et al., "The vaginal microbiome: rethinking health and diseases," Annual Review of Microbiology, vol. 66, 2012, pp. 371-389.
Mach et al., "Endurance exercise and gut microbiota: A review," Journal of Sport and Health Science, vol. 6, No. 2, Jun. 2017, pp. 179-197.
Mahdiani et al., "Protective effect of luteolin against chemical and natural toxicants by targeting NF-κB pathway," Biofactors, vol. 48, No. 4, Jul. 2022, pp. 744-762. Abstract only.
Malaguarnera et al., "Bifidobacterium longum with Fructo-Oligosaccharides in Patients with Non Alcoholic Steatohepatitis," Digestive Diseases and Sciences, vol. 57, 2012, pp. 545-553.

(56) References Cited

OTHER PUBLICATIONS

Matsui et al., "Biological Rhythms in the Skin," International Journal of Molecular Sciences, vol. 17, No. 801, May 2016, 15 pages.

Mayrovitz et al., "Assessing Potential Circadian, Diurnal, and Ultradian Variations in Skin Biophysical Properties," Cureus, vol. 13, No. 9, Sep. 2021, 18 pages.

McFadzean, "Exercise can help modulate human gut microbiota," Honors Thesis Submitted to the University of Colorado Department of Evolutionary Biology, Apr. 7, 2014, 34 pages.

Nakai et al., "Effects of Topical N-Acetylcysteine on Skin Hydration/Transepidermal Water Loss in Healthy Volunteers and Atopic Dermatitis Patients," Annals of Dermatology, vol. 27, No. 4, Aug. 2015, pp. 450-451.

Neves et al., "Efficacy of a topical serum containing L-ascorbic acid, neohesperidin, pycnogenol, tocopherol, and hyaluronic acid in relation to skin aging signs," Journal of Cosmetic Dermatology, vol. 21, No. 10, Oct. 2022, pp. 4462-4469. Abstract only.

Nisbet et al., "Clinical and in vitro evaluation of new anti-redness cosmetic products in subjects with winter xerosis and sensitive skin," International Journal of Cosmetic Science, vol. 41, No. 6, Dec. 2019, pp. 534-547.

Norton et al., "The immune response to Lactococcus lactis: Implications for its use as a vaccine delivery vehicle," FEMS Microbiology Letters, vol. 120, No. 3, Jul. 15, 1994, pp. 249-256. Abstract only.

O'Hanlon et al., "In vaginal fluid, bacteria associated with bacterial vaginosis can be suppressed with lactic acid but not hydrogen peroxide," BMC Infectious Diseases, vol. 11, No. 200, 2011, 8 pages.

Paladine et al., "Vaginitis: Diagnosis and Treatment," American Family Physician, vol. 97, No. 5, Mar. 1, 2018, pp. 321-329.

Park et al., "Fermented black rice and blueberry with Lactobacillus plantarum MG4221 improve UVB-induced skin injury," Food and Agricultural Immunology, vol. 32, No. 1, 2021, pp. 499-515.

Pinto et al., "Plantaricin A synthesized by Lactobacillus plantarum induces in vitro proliferation and migration of human keratinocytes and increases the expression of TGF-β1, FGF7, VEGF-A and IL-8 genes," Peptides, vol. 32, No. 9, Sep. 2011, pp. 1815-1824. Abstract only.

Ragusa et al., "Spirulina for Skin Care: A Bright Blue Future," Cosmetics, vol. 8, No. 1, Jan. 2021, 19 pages.

Ravel et al., "Vaginal microbiome of reproductive-age women," PNAS, vol. 108, Suppl. 1, Mar. 15, 2011, pp. 4680-4687.

Repa et al., "Mucosal co-application of lactic acid bacteria and allergen induces counter-regulatory immune responses in a murine model of birch pollen allergy," Vaccine, vol. 22, No. 1 2003, pp. 87-95. Abstract only.

Scaglione et al., "Considerations on D-mannose Mechanism of Action and Consequent Classification of Marketed Healthcare Products," Frontiers In Pharmacology, vol. 12, No. 636377, Mar. 2, 2021, 7 pages.

Schaeffer et al., "Effect of Carbohydrates on Adherence of *Escherichia coli* to Human Urinary Tract Epithelial Cells," Infection and Immunity, vol. 30, No. 2, Nov. 1980, pp. 531-537.

Sevilla et al., "Revisiting the role of melatonin in human melanocyte physiology: A skin context perspective," Journal of Pineal Research, vol. 72, No. 3, Apr. 2022, 23 pages.

Sheikh, "Is Crispr the Next Antibiotic?," The New York Times, Oct. 29, 2019, retrieved from https://www.nytimes.com/2019/28/health/crispr-genetics-antibiotic-resistance.html, 2 pages.

Shen et al., "Propionibacterium acnes related anti-inflammation and skin hydration activities of madecassoside, a pentacyclic triterpene saponin from Centella asiatica," Bioscience, Biotechnology, and Biochemistry, vol. 83, No. 3, 2019, pp. 561-568.

Sheweita et al., "Preclinical studies on melanogenesis proteins using a resveratrol-nanoformula as a skin whitener," International Journal of Biological Macromolecules, vol. 223, Part A, Dec. 2022, pp. 870-881. Abstract only.

Simmering et al., "The Increase in Hospitalizations for Urinary Tract Infections and the Associated Costs in the United States, 1998-2011," Open Forum Infectious Diseases, vol. 4, No. 1, Feb. 24, 2017, 7 pages.

Sivieri et al., "Lactobacillus acidophilus CRL 1014 improved "gut health" in the SHIME reactor," BMC Gastroenterology, vol. 13, No. 100, 2013, 9 pages.

Spinler et al., "Human-derived probiotic Lactobacillus reuteri demonstrate antimicrobial activities targeting diverse enteric bacterial pathogens," Anaerobe, vol. 14, Feb. 29, 2008, pp. 166-171.

Sporn et al., "Chemoprevention of cancer," Carcinogenesis, vol. 21, No. 3, 2000, pp. 525-530.

Thongaram et al., "Human milk oligosaccharide consumption by probiotic and human-associated bifidobacteria and lactobacilli," Journal of Dairy Science, vol. 100, No. 10, Oct. 2017, pp. 7825-7833.

Traisaeng et al., "A Derivative of Butyric Acid, the Fermentation Metabolite of *Staphylococcus epidermidis*, Inhibits the Growth of a *Staphylococcus aureus* Strain Isolated from Atopic Dermatitis Patients," Toxins, vol. 11, No. 6, May 2019, 12 pages.

Van Der Veer et al., "Comparative genomics of human Lactobacillus crispatus isolates reveals genes for glycosylation and glycogen degradation: implications for in vivo dominance of the vaginal microbiota," Microbiome, vol. 7, No. 49, 2019, 14 pages.

Van Hemert et al., "Migraine associated with gastrointestinal disorders: review of the literature and clinical implications," Frontiers in Neurology, vol. 5, No. 241, Nov. 2014, 4 pages.

Wan et al., "Luteolin-7-glucoside Promotes Human Epidermal Stem Cell Proliferation by Upregulating β-Catenin, c-Myc, and Cyclin Expression," Stem Cells International, vol. 2019, No. 1575480, Jun. 2019, 10 pages.

Wilbie et al., "Delivery Aspects of CRISPR/Cas for in Vivo Genome Editing," Accounts of Chemical Research, vol. 52, 2019, pp. 1555-1564.

Yamamura et al., "Oral mucosal adhesive Film containing local anesthetics: in vitro and clinical evaluation." Journal of Biomedical Materials Research, Fall 1998, vol. 43, No. 3, pp. 313-317. Abstract only.

Yatsuhashi et al., "Effects of Glycogen on Ceramide Production in Cultured Human Keratinocytes via Acid Sphingomyelinase Activation," Journal of Applied Glycoscience, vol. 68, 2021, pp. 41-46.

Yosipovitch et al., "Time-Dependent Variations of the Skin Barrier Function in Humans: Transepidermal Water Loss, Stratum Corneum Hydration, Skin Surface pH, and Skin Temperature," Journal of INvestigative Dermatology, vol. 110, No. 1, Jan. 1998, pp. 20-23.

Zahedi et al., "Development of plasma functionalized polypropylene wound dressing for betaine hydrochloride controlled drug delivery on diabetic wounds," Scientific Reports, vol. 11, No. 9641, 2021, 18 pages.

Zhao et al., "Microbiome-generated amyloid and potential impact on amyloidogenesis in Alzheimer's disease (AD)," Journal of Nature and Science, vol. 1, No. 7, 2015, pp. 1-5.

Zhou et al., "Nicotinamide Mononucleotide Combined With Lactobacillus fermentum TKSN041 Reduces the Photoaging Damage in Murine Skin by Activating AMPK Signaling Pathway," Frontiers in Pharmacology, vol. 12, No. 643089, Mar. 2021, 17 pages.

Official Action for U.S. Appl. No. 14/574,517 dated Jan. 6, 2016, 13 pages.

Notice of Allowance for U.S. Appl. No. 14/574,517, dated Apr. 15, 2016, 8 pages.

Corrected Notice of Allowance for U.S. Appl. No. 14/574,517, dated Jul. 7, 2016, 2 pages.

Official Action for U.S. Appl. No. 14/954,074, dated Jun. 30, 2016, 4 pages.

Notice of Allowance for U.S. Appl. No. 14/954,074, dated Jul. 20, 2016, 7 pages.

Official Action for U.S. Appl. No. 15/270,034, dated Apr. 6, 2017, 5 pages.

Notice of Allowance for U.S. Appl. No. 15/270,034, dated May 5, 2017, 7 pages.

Official Action for U.S. Appl. No. 15/392,173, dated Jan. 22, 2018, 8 pages.

(56) References Cited

OTHER PUBLICATIONS

Official Action for U.S. Appl. No. 15/392,173, dated Jul. 6, 2018, 13 pages.
Notice of Allowance for U.S. Appl. No. 15/392,173, dated Dec. 5, 2018, 8 pages.
Official Action for U.S. Appl. No. 16/229,252, dated Feb. 28, 2019, 5 pages.
Notice of Allowance for U.S. Appl. No. 16/229,252, dated Aug. 21, 2019, 7 pages.
Official Action for U.S. Appl. No. 16/722,117, dated Feb. 20, 2020, 6 pages.
Notice of Allowance for U.S. Appl. No. 16/722,117, dated Jul. 30, 2020, 8 pages.
Official Action for U.S. Appl. No. 17/011,175, dated Jun. 17, 2021, 9 pages.
Notice of Allowance for U.S. Appl. No. 17/011,175, dated Nov. 5, 2021, 8 pages.
Official Action for U.S. Appl. No. 17/023,736, dated Nov. 10, 2021, 7 pages.
Notice of Allowance for U.S. Appl. No. 17/023,736, dated Apr. 14, 2022, 8 pages.
Official Action for U.S. Appl. No. 17/893,384, dated May 9, 2023, 8 pages.
Notice of Allowance for U.S. Appl. No. 17/893,384, dated Aug. 23, 2023, 7 pages.
Official Action for U.S. Appl. No. 18/143,399, dated Sep. 7, 2023, 8 pages.
Notice of Allowance for U.S. Appl. No. 18/143,399, dated Dec. 7, 2023, 7 pages.
Official Action for U.S. Appl. No. 18/232,433, dated Dec. 7, 2023, 20 pages.
Notice of Allowance for U.S. Appl. No. 18/232,433, dated Feb. 2, 2024, 8 pages.
Official Action for U.S. Appl. No. 17/694,775, dated Aug. 14, 2024, 8 pages.
Official Action for U.S. Appl. No. 18/232,980, dated Nov. 6, 2023, 14 pages.
Notice of Allowance for U.S. Appl. No. 18/232,980, dated Dec. 28, 2023, 7 pages.
Official Action for U.S. Appl. No. 18/234,132, dated Dec. 7, 2023, 8 pages.
Notice of Allowance for U.S. Appl. No. 18/234,132, dated Jan. 19, 2024, 7 pages.
Official Action for U.S. Appl. No. 15/403,823, dated Oct. 30, 2017, 7 pages.
Official Action for U.S. Appl. No. 15/403,823, dated May 25, 2018, 9 pages.
Notice of Allowance for U.S. Appl. No. 15/403,823, dated Jun. 28, 2018, 9 pages.
Official Action for U.S. Appl. No. 16/160,336, dated Nov. 27, 2018, 6 pages.
Notice of Allowance for U.S. Appl. No. 16/160,336, dated Feb. 15, 2019, 7 pages.
Official Action for U.S. Appl. No. 16/423,375, dated Jul. 3, 2019, 6 pages.
Notice of Allowance for U.S. Appl. No. 16/423,375, dated Oct. 16, 2019, 8 pages.
Official Action for U.S. Appl. No. 16/782,364, dated Apr. 9, 2020, 5 pages.
Notice of Allowance for U.S. Appl. No. 16/782,364, dated Jul. 27, 2020, 7 pages.
Official Action for U.S. Appl. No. 16/917,096, dated Jul. 31, 2020, 5 pages.
Official Action for U.S. Appl. No. 16/617,096, dated Oct. 19, 2020, 8 pages.
Official Action for U.S. Appl. No. 17/027,953, dated Jan. 29, 2021, 5 pages.
Notice of Allowance for U.S. Appl. No. 17/027,953, dated Apr. 19, 2021, 8 pages.
Official Action for U.S. Appl. No. 17/337,600, dated Jul. 6, 2021, 5 pages.
Notice of Allowance for U.S. Appl. No. 17/337,600, dated Sep. 9, 2021, 7 pages.
Official Action for U.S. Appl. No. 17/835,204, dated Jul. 28, 2022, 6 pages.
Notice of Allowance for U.S. Appl. No. 17/835,204, dated Aug. 24, 2022, 7 pages.
Official Action for U.S. Appl. No. 17/848,759, dated Sep. 14, 2022, 6 pages.
Notice of Allowance for U.S. Appl. No. 17/848,759, dated Dec. 29, 2022, 7 pages.
Corrected Notice of Allowance for U.S. Appl. No. 17/848,759, dated Jan. 12, 2023, 4 pages.
Official Action for U.S. Appl. No. 17/854,422, dated Sep. 28, 2022, 7 pages.
Official Action for U.S. Appl. No. 17/854,422, dated Jan. 10, 2023, 6 pages.
Notice of Allowance for U.S. Appl. No. 17/854,422, dated Feb. 17, 2023, 7 pages.
Official Action for U.S. Appl. No. 18/087,545, dated May 24, 2023, 5 pages.
Notice of Allowance for U.S. Appl. No. 18/087,545, dated Jul. 26, 2023, 7 pages.
Official Action for U.S. Appl. No. 18/178,847, dated Jul. 13, 2023, 8 pages.
Notice of Allowance for U.S. Appl. No. 18/178,847, dated Aug. 8, 2023, 8 pages.
Official Action for U.S. Appl. No. 18/535,722, dated Apr. 10, 2024, 6 pages.
Official Action for U.S. Appl. No. 18/130,946, dated Jun. 30, 2023, 6 pages.
Notice of Allowance for U.S. Appl. No. 18/130,946, dated Aug. 1, 2023, 8 pages.
Official Action for U.S. Appl. No. 18/235,686, dated Nov. 16, 2023, 7 pages.
Notice of Allowance for U.S. Appl. No. 18/235,686, dated Jan. 26, 2024, 8 pages.
Official Action for U.S. Appl. No. 15/228,454, dated Sep. 23, 2016, 11 pages.
Notice of Allowance for U.S. Appl. No. 15/228,454, dated Jan. 23, 2017, 7 pages.
Official Action for U.S. Appl. No. 15/437,976, dated Mar. 29, 2017, 8 pages.
Notice of Allowance for U.S. Appl. No. 15/437,976, dated Jul. 12, 2017, 7 pages.
Official Action for U.S. Appl. No. 15/639,767, dated Aug. 14, 2017, 11 pages.
Official Action for U.S. Appl. No. 15/639,767, dated Sep. 27, 2018, 13 pages.
Notice of Allowance for U.S. Appl. No. 15/369,767, dated Feb. 15, 2019, 8 pages.
Official Action for U.S. Appl. No. 16/426,346, dated Aug. 2, 2019, 10 pages.
Official Action for U.S. Appl. No. 16/426,346, dated Jan. 13, 2020, 7 pages.
Notice of Allowance for U.S. Appl. No. 16/426,346, dated Mar. 25, 2020, 7 pages.
Official Action for U.S. Appl. No. 13/367,052, dated Jan. 16, 2014, 8 pages.
Notice of Allowance for U.S. Appl. No. 13/367,052, dated Feb. 24, 2014, 5 pages.
Official Action for U.S. Appl. No. 14/225,503, dated May 4, 2016, 6 pages.
Notice of Allowance for U.S. Appl. No. 14/225,503, dated Jul. 20, 2016, 5 pages.
Official Action for U.S. Appl. No. 14/752,192, dated Jul. 8, 2016, 8 pages.
Notice of Allowance for U.S. Appl. No. 14/752,192, dated Sep. 16, 2016, 5 pages.
Official Action for U.S. Appl. No. 15/378,425, dated May 15, 2019, 82 pages.

(56) References Cited

OTHER PUBLICATIONS

Official Action for U.S. Appl. No. 15/378,425, dated Oct. 2, 2019, 41 pages.
Official Action for U.S. Appl. No. 15/378,425, dated Jul. 15, 2020, 21 pages.
Official Action for U.S. Appl. No. 15/378,425, dated Nov. 10, 2020, 29 pages.
Official Action for U.S. Appl. No. 15/385,278, dated Oct. 30, 2017, 23 pages.
Official Action for U.S. Appl. No. 15/385,278, dated Apr. 13, 2018, 18 pages.
Notice of Allowance for U.S. Appl. No. 15/385,278, dated May 31, 2018, 10 pages.
Official Action for U.S. Appl. No. 16/136,950, dated Nov. 25, 2019, 11 pages.
Official Action for U.S. Appl. No. 16/136,950, dated Jan. 31, 2020, 8 pages.
Official Action for U.S. Appl. No. 16/884,772, dated Sep. 30, 2021, 8 pages.
Notice of Allowance for U.S. Appl. No. 16/884,772, dated Feb. 22, 2022, 7 pages.
Official Action for U.S. Appl. No. 17/836,079, dated Jul. 29, 2024, 22 pages.
Official Action for U.S. Appl. No. 15/384,716, dated Nov. 1, 2017, 31 pages.
Notice of Allowance for U.S. Appl. No. 15/384,716, dated Apr. 2, 2018, 9 pages.
Official Action for U.S. Appl. No. 15/983,250, dated Mar. 5, 2019, 23 pages.
Official Action for U.S. Appl. No. 15/983,250, dated May 24, 2019, 21 pages.
Official Action for U.S. Appl. No. 15/983,250, dated Jan. 14, 2020, 8 pages.
Notice of Allowance for U.S. Appl. No. 15/983,250, dated Feb. 14, 2020, 8 pages.
Official Action for U.S. Appl. No. 16/904,056, dated Dec. 6, 2021, 12 pages.
Official Action for U.S. Appl. No. 16/904,056, dated May 17, 2022, 11 pages.
Notice of Allowance for U.S. Appl. No. 16/904,056, dated Aug. 11, 2022, 8 pages.
Corrected Notice of Allowance for U.S. Appl. No. 16/904,056, dated Aug. 24, 2022, 6 pages.
Official Action for U.S. Appl. No. 17/738,771, dated Aug. 9, 2024, 9 pages. Restriction Requirement.
Official Action for U.S. Appl. No. 18/103,768, dated Apr. 25, 2023, 5 pages.
Notice of Allowance for U.S. Appl. No. 18/103,768, dated Aug. 1, 2023, 7 pages.
Official Action for U.S. Appl. No. 18/234,544, dated Dec. 26, 2023, 8 pages.
Notice of Allowance for U.S. Appl. No. 18/234,544, dated Jan. 31, 2024, 7 pages.
Supplemental Notice of Allowance for U.S. Appl. No. 18/234,544, dated Feb. 22, 2024, 2 pages.
Fila et al., "Blue light treatment of Pseudomonas aeruginosa: Strong bacterial activity, synergism with antibiotics and inactivation of virulence factors," Virulence, vol. 8, No. 6, 2017, pp. 938-958.
Official Action for U.S. Appl. No. 18/615,672, dated Oct. 1, 2024, 11 pages.
Official Action for U.S. Appl. No. 17/567,295, dated Sep. 13, 2024, 6 pages.
Official Action for U.S. Appl. No. 17/738,771, dated Sep. 5, 2024, 19 pages.

* cited by examiner

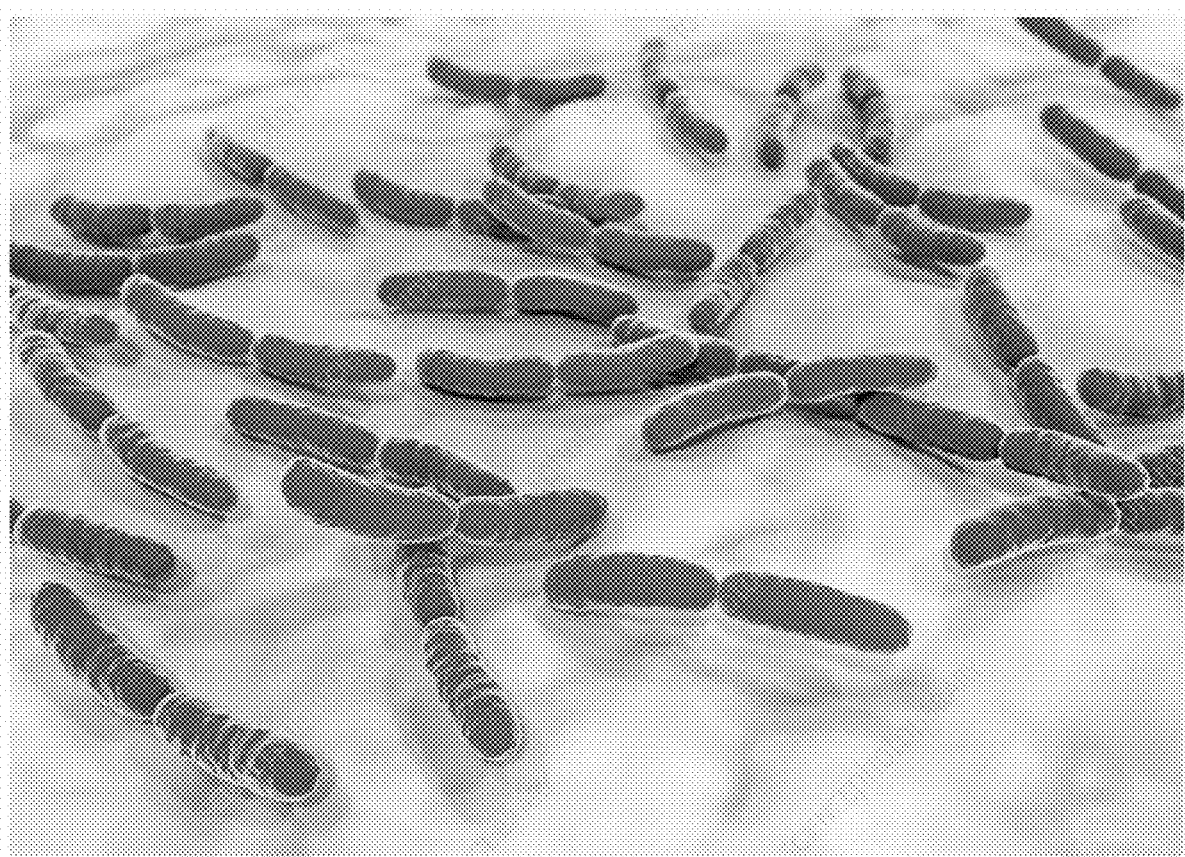
Fig. 1 – *L. crispatus*

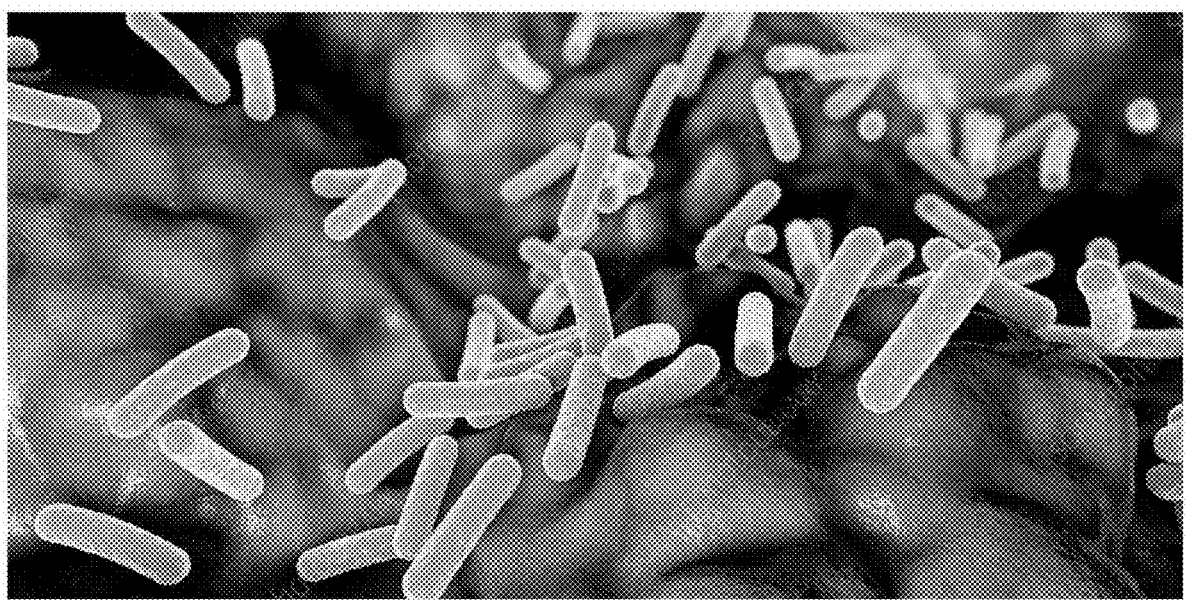
Fig. 2 - *Faecalibacterium prausnitzii*

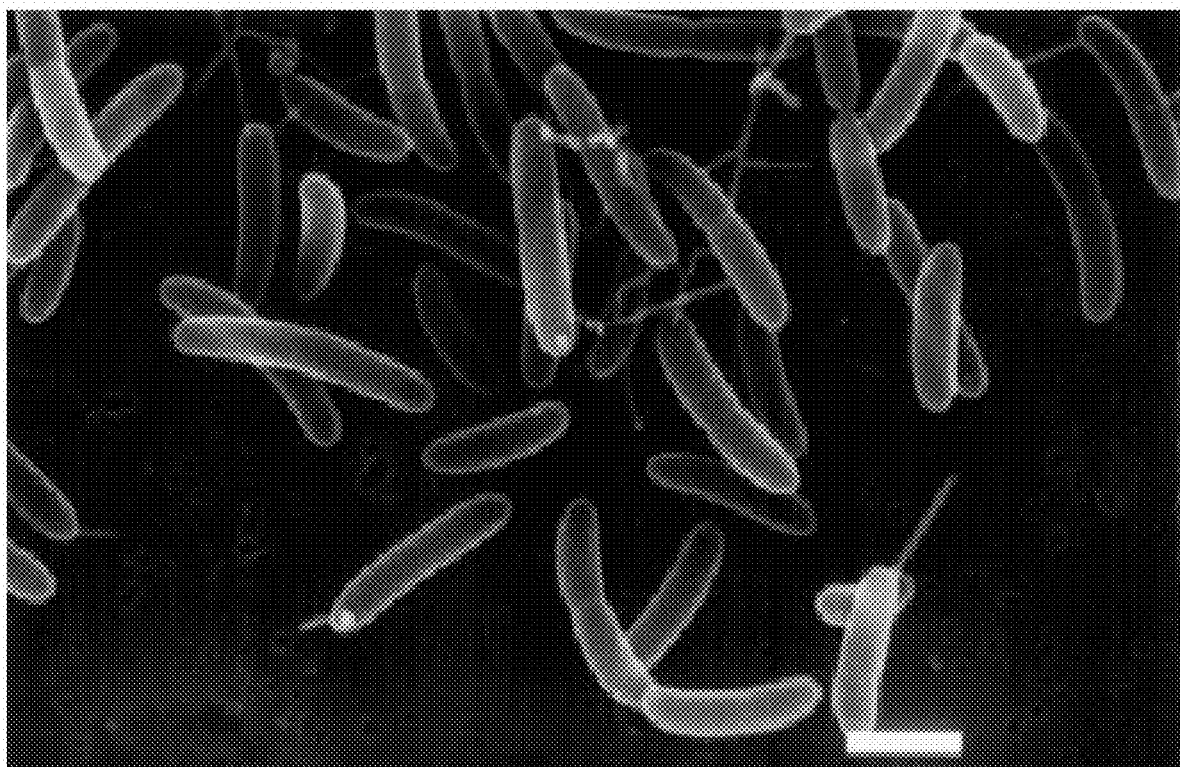
Fig. 3 - Roseburia

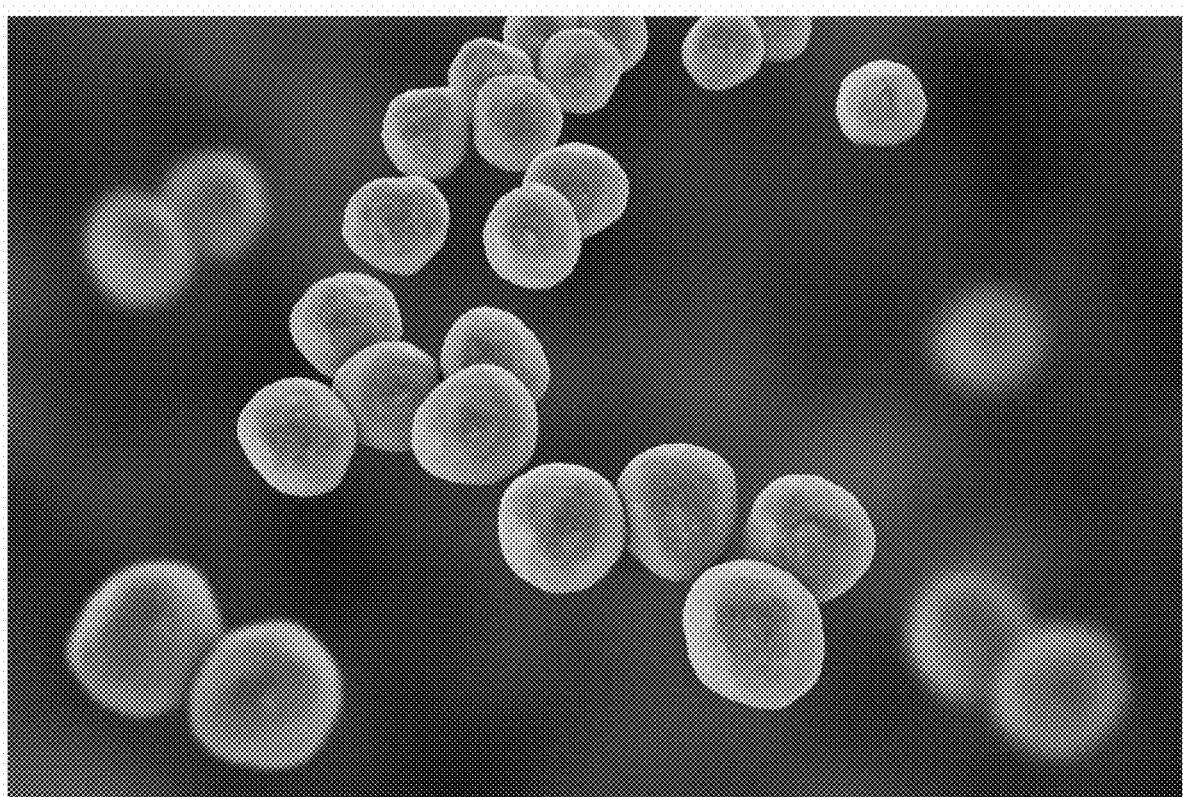
Fig. 4 - *Veillonella*

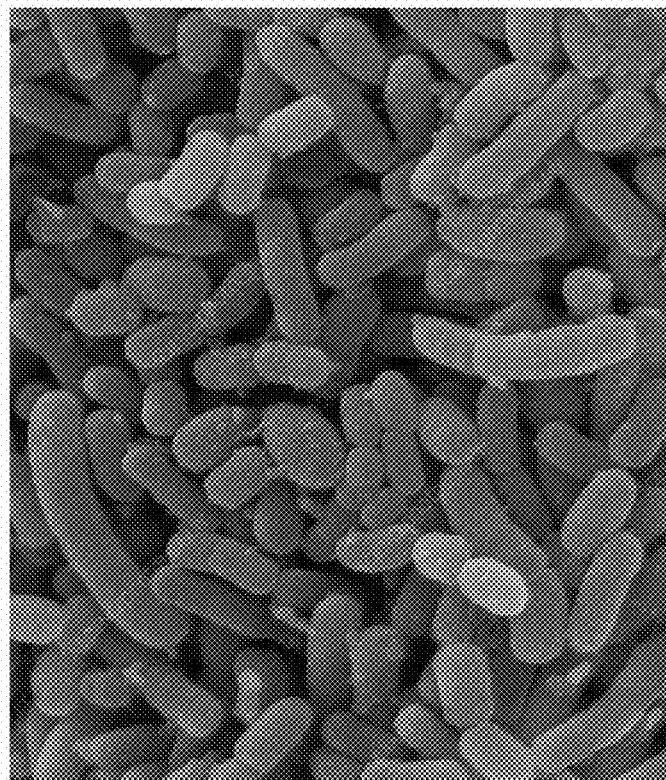
FIG. 5 - *Prevotella*

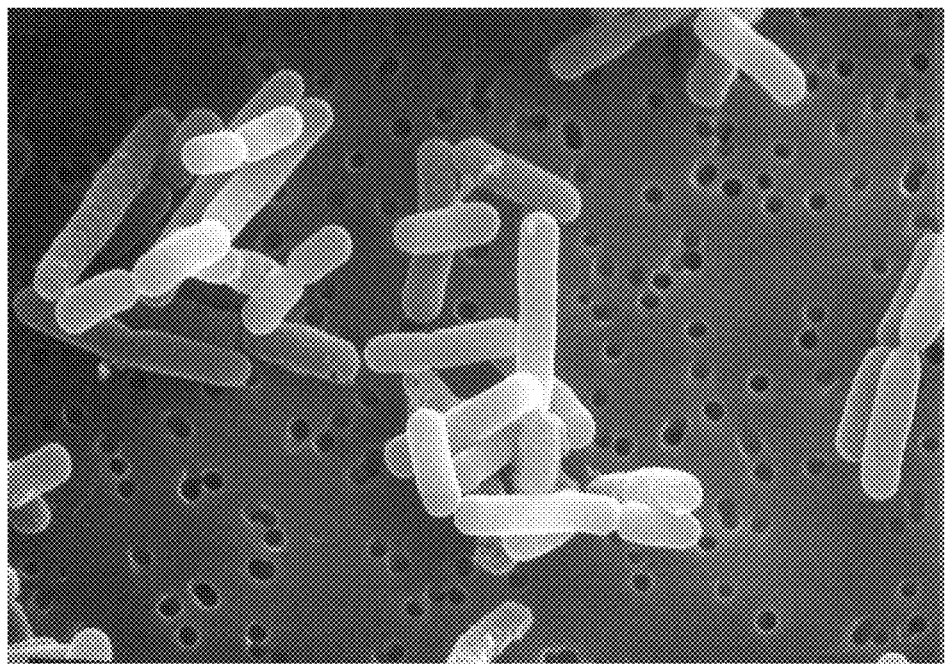
Fig. 6 – *Lactobacillus reteri*
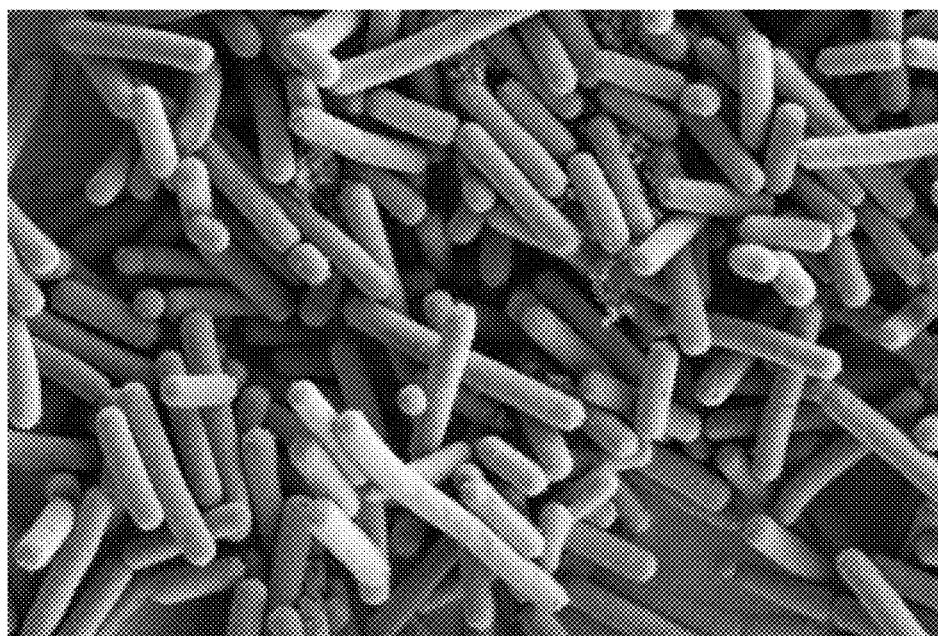
Fig. 7 - *Lactobacillus johnsonii*

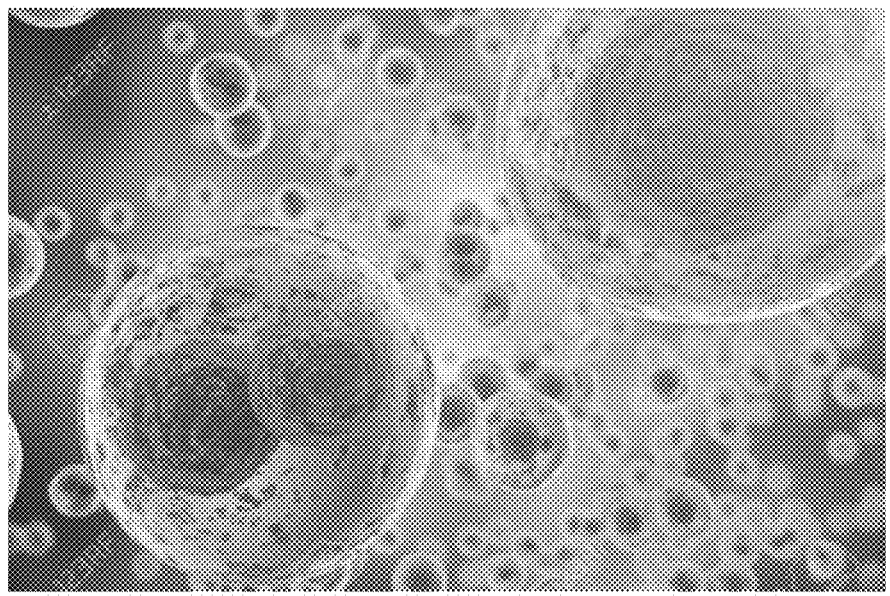
Fig. 8 - *Nitrosomonas eutropha*

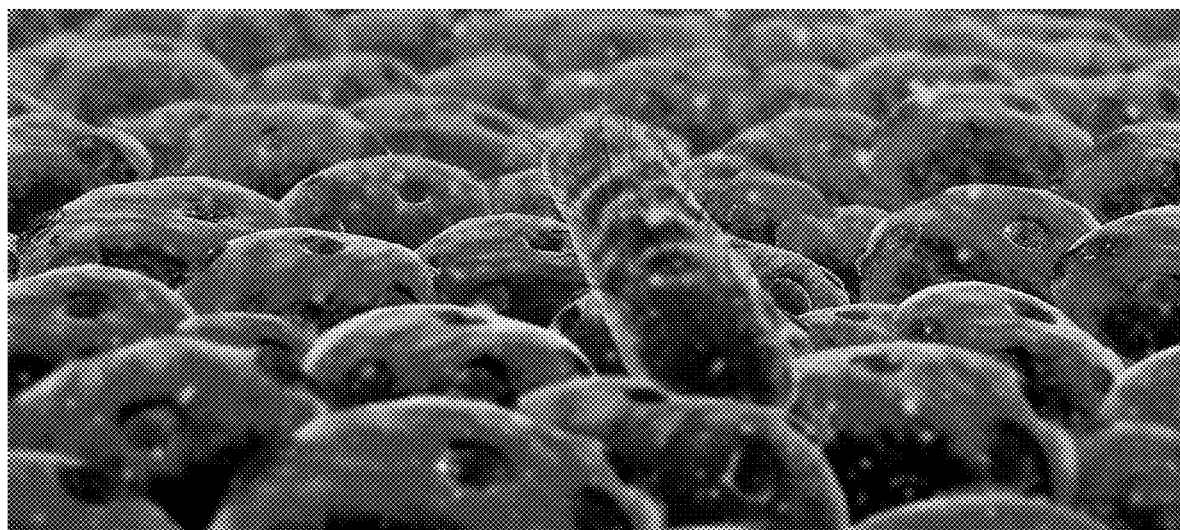
FIG 9 - ODORIBACTER

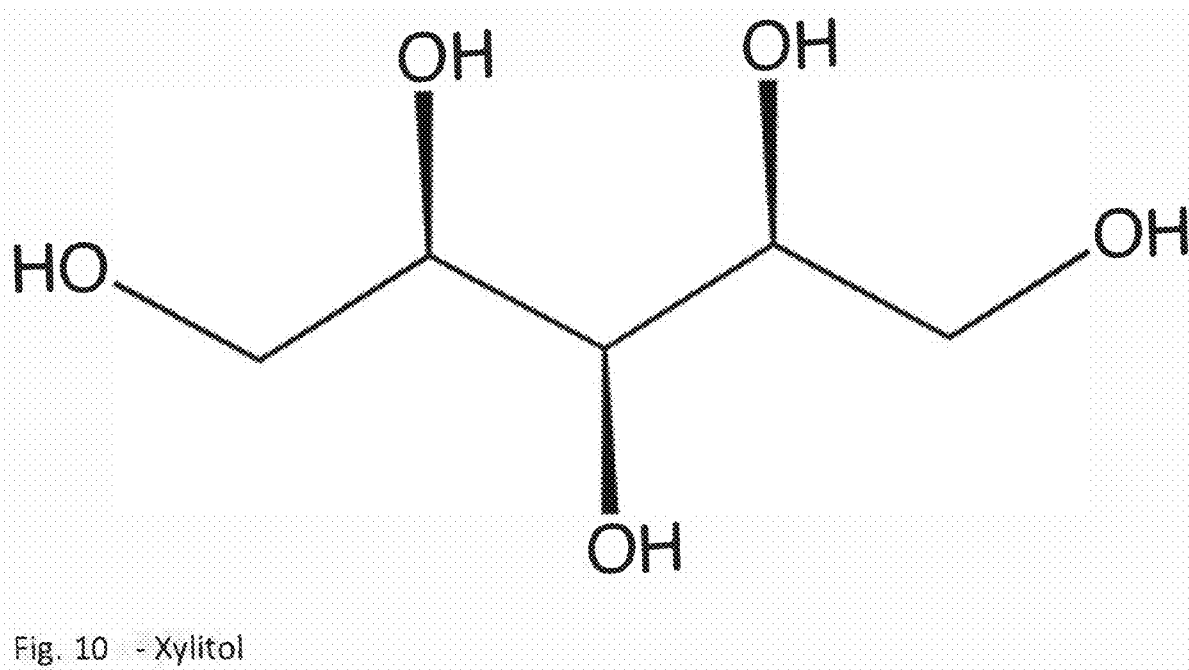
Fig. 10 - Xylitol

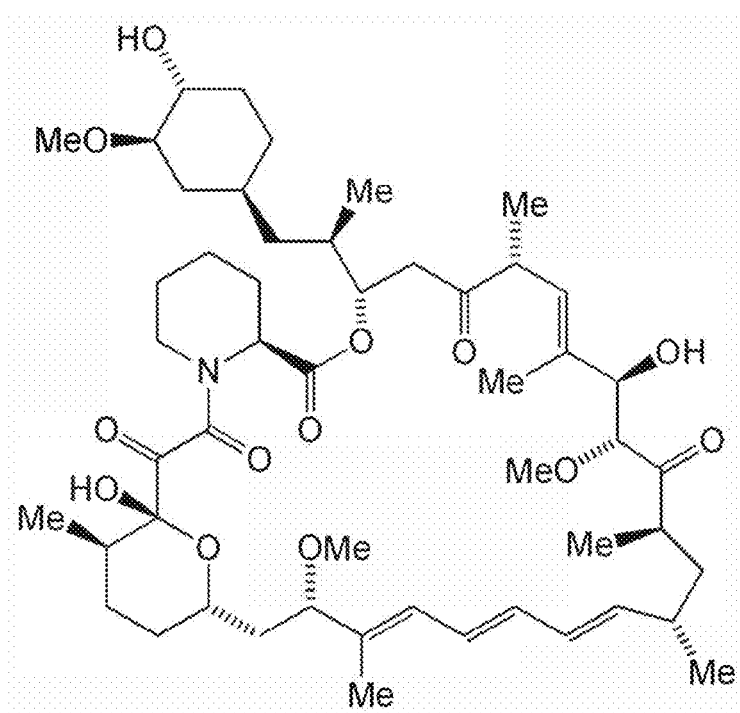
Fig 11 - Rapamycin

PROBIOTIC METHOD AND COMPOSITION FOR MAINTAINING A HEALTHY VAGINAL MICROBIOME

RELATED APPLICATIONS

This application is a continuation of U.S. patent application Ser. No. 18/620,483, filed Mar. 28, 2024, which is a continuation of U.S. patent application Ser. No. 18/615,672, filed Mar. 25, 2024, which is a continuation of U.S. patent application Ser. No. 18/234,132, filed Aug. 15, 2023 (now U.S. Pat. No. 11,980,643, issued May 14, 2024), which is a continuation-in-part of application Ser. No. 18/232,980, filed Aug. 11, 2023 (now U.S. Pat. No. 11,969,445, issued Apr. 30, 2024), which is a continuation-in-part of U.S. patent application Ser. No. 18/232,433, filed Aug. 10, 2023 (now U.S. Pat. No. 12,005,085, issued Jun. 11, 2024), which is a continuation-in-part of U.S. patent application Ser. No. 18/143,399, filed May 4, 2023 (now U.S. Pat. No. 11,951,140, issued Apr. 9, 2024), which is a continuation of U.S. patent application Ser. No. 17/893,384, filed Aug. 23, 2022 (now U.S. Pat. No. 11,951,139, issued Apr. 9, 2024), which is a continuation-in-part application of U.S. patent application Ser. No. 17/694,775, filed Mar. 15, 2022, which is a continuation-in-part of U.S. patent application Ser. No. 17/023,736, filed Sep. 17, 2020 (now U.S. Pat. No. 11,419,903, issued Aug. 23, 2022, which is a continuation-in-part of U.S. patent application Ser. No. 17/011,175, filed Sep. 3, 2020 (now U.S. Pat. No. 11,273,187, issued Mar. 15, 2022), which is a continuation-in-part of U.S. patent application Ser. No. 16/722,117, filed Dec. 20, 2019 (now U.S. Pat. No. 10,842,834, issued Nov. 24, 2020), which is a continuation-in-part of U.S. patent application Ser. No. 16/229,252, filed Dec. 21, 2018 (now U.S. Pat. No. 10,512,661, issued Dec. 24, 2019), which is a continuation-in-part of U.S. patent application Ser. No. 15/392,173, filed Dec. 28, 2016 (now U.S. Pat. No. 10,245,288, issued Apr. 2, 2019), which is a non-provisional of U.S. Provisional Patent Application Ser. No. 62/275,341, filed on Jan. 6, 2016.

This application is a continuation of U.S. patent application Ser. No. 18/535,722, filed Dec. 11, 2023, which is a continuation-in-part of U.S. patent application Ser. No. 18/235,686, filed Aug. 18, 2023 (now U.S. Pat. No. 11,998,574, issued Jun. 4, 2024), which is a continuation-in-part of U.S. patent application Ser. No. 18/130,946, filed Apr. 5, 2023 (now U.S. Pat. No. 11,833,177, issued Dec. 5, 2023, which is continuation-in-part of U.S. patent application Ser. No. 18/178,847, filed Mar. 28, 2023 (now U.S. Pat. No. 11,839,632, issued Dec. 12, 2023), which is a continuation-in-part of U.S. patent application Ser. No. 18/087,545, filed Dec. 22, 2022 (now U.S. Pat. No. 11,826,388, issued Nov. 28, 2023), which is a continuation-in-part of U.S. patent application Ser. No. 17/854,422, filed Jun. 30, 2022 (now U.S. Pat. No. 11,672,835, issued Jun. 13, 2023), which is a continuation-in-part of U.S. patent application Ser. No. 17/848,759, filed Jun. 24, 2022 (now U.S. Pat. No. 11,642,382, issued May 9, 2023), which is a continuation-in-part of U.S. patent application Ser. No. 17/835,204 filed Jun. 8, 2022 (now U.S. Pat. No. 11,529,379, issued Dec. 20, 2022), which is a continuation-in-part of U.S. patent application Ser. No. 17/567,295 filed Jan. 3, 2022, which is a continuation-in-part of U.S. patent application Ser. No. 17/337,600, filed Jun. 3, 2021 (now U.S. Pat. No. 11,213,552, issued Jan. 4, 2022), which is a continuation-in-part of Ser. No. 17/027,953, filed on Sep. 22, 2020 (now U.S. Pat. No. 11,026,982, issued Jun. 8, 2021), which is a continuation-in-part of U.S. patent application Ser. No. 16/917,096, filed Jun. 30, 2020 (now U.S. Pat. No. 10,940,169, issued Mar. 9, 2021), which is a continuation-in-part of U.S. patent application Ser. No. 16/782,364, filed Feb. 5, 2020 (now U.S. Pat. No. 10,835,560, issued Nov. 17, 2020), which is a continuation-in-part of U.S. patent application Ser. No. 16/423,375, filed May 28, 2019 (now U.S. Pat. No. 10,555,976, issued Feb. 11, 2020), which is a continuation of U.S. patent application Ser. No. 16/160,336, filed Oct. 15, 2018 (now U.S. Pat. No. 10,314,866, issued Jun. 11, 2019), which is a continuation of U.S. patent application Ser. No. 15/403,823, filed Jan. 11, 2017 (now U.S. Pat. No. 10,111,913, issued Oct. 30, 2018), which is a non-provisional of U.S. Provisional Patent Application Ser. No. 62/296,186, filed on Feb. 17, 2016.

This application is a continuation of U.S. Provisional Patent Application Ser. No. 63/649,793, filed on May 20, 2024.

This application is a continuation of U.S. patent application Ser. No. 18/234,544, filed Aug. 16, 2023 (now U.S. Pat. No. 11,998,479, issued Jun. 4, 2024), which is a continuation-in part of U.S. patent application Ser. No. 18/103,768, filed Jan. 31, 2023 (now U.S. Pat. No. 11,844,720, issued Dec. 19, 2023), which is a continuation-in-part of U.S. patent application Ser. No. 17/738,771, filed May 6, 2022, which is a continuation-in-part of U.S. patent application Ser. No. 16/904,056, filed Jun. 17, 2020 (now U.S. Pat. No. 11,523,934, issued Dec. 13, 2022), which is a continuation-in-part of U.S. patent application Ser. No. 15/983,250 filed on May 18, 2018 (now U.S. Pat. No. 10,687,975, issued Jun. 23, 2020), which is a continuation-in-part of U.S. patent application Ser. No. 15/384,716 filed on Dec. 20, 2016 (now issued U.S. Pat. No. 9,987,224, issued Jun. 5, 2018), which claims priority of U.S. Provisional Patent Application Ser. No. 62/387,405, filed on Dec. 24, 2015.

This application is also a continuation of U.S. patent application Ser. No. 17/836,079, filed Jun. 9, 2022, which is a continuation-in-part of U.S. patent application Ser. No. 16/884,772 filed on May 27, 2020 (now U.S. Pat. No. 11,357,722, issued Jun. 14, 2022, which is a continuation-in-part of U.S. patent application Ser. No. 16/136,950, filed Sep. 20, 2018 (now U.S. Pat. No. 10,668,014, issued Jun. 2, 2020), which is a continuation of U.S. patent application Ser. No. 15/385,278, filed Dec. 20, 2016 (now U.S. Pat. No. 10,085,938, issued Oct. 2, 2018), which claims the benefit of U.S. Provisional Application Ser. No. 62/387,404, filed Dec. 24, 2015.

The present application is a continuation of U.S. patent application Ser. No. 17/543,992, filed Dec. 7, 2021, which is a continuation-in-part of U.S. patent application Ser. No. 16/804,361, filed Feb. 28, 2020 (now U.S. Pat. No. 11,191,665, issued Dec. 7, 2021), which is a continuation-in-part of U.S. patent application Ser. No. 16/020,433, filed Jun. 27, 2018 (now U.S. Pat. No. 10,583,033, issued Mar. 10, 2020), which is a continuation-in-part application of U.S. Ser. No. 15/342,642, filed Nov. 3, 2016 (now U.S. Pat. No. 10,010,568, issued Jul. 3, 2018), which seeks priority from U.S. Provisional Patent Application Ser. No. 62/260,906, filed Nov. 30, 2015.

This application is a continuation application of U.S. patent application Ser. No. 16/776,861, filed Jan. 30, 2020 (now U.S. Pat. No. 10,864,109, issued Dec. 15, 2020), which is a continuation of U.S. patent application Ser. No. 16/142,171, filed Sep. 26, 2018 (now U.S. Pat. No. 10,548,761, issued Feb. 4, 2020), which is a continuation-in-part of U.S. patent application Ser. No. 15/395,419, filed Dec. 30, 2016 (now U.S. Pat. No. 10,086,018, issued Oct. 2, 2018), which is a non-provisional of U.S. Provisional Patent Application Ser. No. 62/274,550, filed on Jan. 4, 2016.

This application is a continuation-in-part of U.S. patent application Ser. No. 16/426,346, filed May 30, 2019 (now U.S. Pat. No. 10,716,815, issued Jul. 21, 2020), which is a continuation of U.S. patent application Ser. No. 15/639,767, filed Jun. 30, 2017 (now issued U.S. Pat. No. 10,314,865, issuing Jun. 11, 2019), which is a continuation-in-part of U.S. patent application Ser. No. 15/437,976, filed Feb. 21, 2017 (now U.S. Pat. No. 9,730,967, issued Aug. 15, 2017), which is a continuation-in-part application of U.S. patent application Ser. No. 15/228,454, filed Aug. 4, 2016 (now U.S. Pat. No. 9,585,920, issued Mar. 7, 2017).

The present application is a continuation-in-part of U.S. patent application Ser. No. 15/270,034, filed Sep. 20, 2016 (now U.S. Pat. No. 9,750,802, issued Sep. 5, 2017), which is a continuation-in-part of U.S. patent application Ser. No. 14/954,074, filed Nov. 30, 2015 (now U.S. Pat. No. 9,457,077, issued Oct. 4, 2016), which is a continuation-in-part of U.S. patent application Ser. No. 14/574,517, filed Dec. 18, 2014 (now U.S. Pat. No. 9,408,880, issued Aug. 9, 2016), which claims the benefit of U.S. Provisional Patent Application No. 62/072,476, filed Oct. 30, 2014, U.S. Provisional Patent Application No. 62/053,926, filed Sep. 23, 2014, U.S. Provisional Patent Application No. 62/014,855, filed Jun. 20, 2014 and U.S. Provisional Patent Application No. 61/919,297, filed Dec. 20, 2013.

This application is a continuation-in-part application of U.S. patent application Ser. No. 16/037,053, filed Jul. 17, 2018 (abandoned).

This application is also a continuation-in-part of U.S. patent application Ser. No. 14/752,192 filed on Jun. 26, 2015 (now U.S. Pat. No. 9,549,842, issued Jan. 24, 2017).

The entire disclosure of the prior applications are considered to be part of the disclosure of the accompanying application and are hereby incorporated by reference.

FIELD OF THE INVENTION

The present invention is directed to a probiotic method and composition for maintaining a healthy vaginal microbiome.

BACKGROUND OF THE INVENTION

The vaginal microbiome is a dynamic, sensitive microenvironment that changes in response to pregnancy, the menstrual cycle, contraceptive use, and diet. A normal, healthy vaginal microbiota is dominated by a variety of *Lactobacillus* spp., including *L. crispatus, L. gasseri, L. iners* and *L. jensenii*. Vaginal dysbiosis predisposes women to a variety of adverse vaginal health conditions. The practice of vaginal douching, once believed to offer benefits, has recently been shown to cause vaginal dysbiosis that detracts, rather than improves upon, a woman's vaginal health.

Feminine hygiene products such as douches, wipes, sprays, washes, and powders are part of a fast-growing industry worth USD 2 billion in the US. Most of these products are marketed to women with the idea that women's bodies are problematic, unclean, and require cosmetic products to maintain a healthy state. Research now suggests that the use of feminine hygiene products may result in the development of more significant or additional symptoms resulting from increased washing and the associated disturbance of the normal vaginal microbiome. A *Lactobacillus*-depleted microbiome has been linked to a variety of adverse vaginal health outcomes, including preterm birth, bacterial vaginosis, and increased risk of sexually transmitted infections.

There is a long felt but unsolved need for a probiotic method and composition for maintaining a healthy vaginal microbiome. The vaginal microbiome is an intricate and dynamic microecosystem that constantly undergoes fluctuations throughout a woman's entire life. As further described herein, both methods and compositions are set forth to achieve the objective of maintaining a healthy vaginal microbiome at these various stages of a woman's life.

SUMMARY OF THE INVENTION

As set forth herein, various embodiments of the present invention are directed to ways to modulate the microbiome of women at various stages of their lives in order to enhance the health of their vaginas, as well as their overall health.

The vaginal microbiome is an intricate and dynamic micro-ecosystem that is a critical component of women's sexual, reproductive, and holistic health. However, in the United States, symptomatic vaginal complaints are responsible for more than 10 million office visits annually. Microbial dysbiosis and fungal infections are a primary cause of vaginitis, defined as inflammation or infection of the vagina. These conditions can cause significant discomfort and reduced quality of life, while also increasing the risk of sexually transmitted infections and adverse pregnancy outcomes. The current standard of care for the three main causes of vaginitis, bacterial vaginosis (BV), *Candida* infections, and trichomoniasis, is treatment with antibiotic or antifungal medications, which often result in high recurrence rates as they do not address the root cause: a disrupted vaginal microbiome.

Urinary tract infections (UTIs) are the most common bacterial infection in the general population, impacting over half of women in their lifetime and resulting in healthcare costs upwards of $2.8 billion annually. After an initial UTI, approximately 20%-30% of women will have a second UTI within 6 months. Recurrent UTIs (rUTIs; defined as 2 infections in 6 months or ≥3 infections in 1 year) significantly impact both a patient's health and the healthcare system and are often treated with long-term repetitive courses of antibiotics. A more effective approach to these recurrent UTIs is needed.

The age and hormone levels of women has a significant impact on the composition of the vaginal microbiome. Until puberty, estrogen levels remain low, which causes the vagina to be dominated with anaerobic micro-organisms. From puberty on, estrogen levels rise, leading to production of cervicovaginal secretions and colonization by high numbers of lactobacilli, with increasing concentrations of lactate as a result. Throughout the menstrual cycle estrogen and glycogen levels vary, ranging from low levels during menses to the highest levels before ovulation, effecting microbiome composition. Upon pregnancy, the vagina remains dominated by lactobacilli but is characterized by lower richness and diversity than in non-pregnant women. In menopause, estrogen and glycogen levels decrease, causing the prior *Lactobacillus* dominance to decrease and eventually cease.

A properly balanced vaginal microbiota prevents urogenital disorders like bacterial vaginosis (BV), urinary tract infections (UTIs), and yeast infections. Described herein are various probiotic compositions for maintaining a healthy vaginal microbiome that employ combinations of bacteria selected to reduce the number of pathogenic bacteria in the vagina and to achieve a healthy balance of beneficial bacteria, often involving the maintenance of a desired pH range to accomplish such an objective. Aspects of the present invention are directed to the provision of suitable prebiotics, probiotics and post biotics in the distinct microbiomes of an individual is employed to arrive at a more comprehensive and holistic way to address dysbiosis of one or more of such microbiomes. Moreover, the dynamic environment of the vaginal microbiome is taken into consideration due to the dramatic events that occasion a woman's life, from the earliest stages of an infant, through childhood, puberty, adulthood, motherhood and finally as a woman enters late age. Each stage of life presents unique challenges with respect to maintaining healthful conditions for a woman, as well as for her infants that she birthed.

Thus, beginning with the profound impacts of the vaginal microbiome on the future health of an infant, certain aspects of the present invention are focused on compositions and methods directed to interventions for a pregnant mother to take with respect to an alteration of one of: her gut microbiome; and vaginal microbiome to positively affect the immunity for her child, with the objective to protect the child against future allergies. It is believed that the infant gut microbiota and immune system are primed shortly after birth with a direct connection to the maternal transfer of humoral immunity to the infant. Enhancing the bacterial population to which an infant is exposed with certain bacteria, for example certain isolated and/or combinations of strains of *Escherichia, Staphylococcus, Bifidobacterium* and/or *Lactobacillus* bacteria, is believed to protect an infant against later life allergies. Various embodiments of the present invention are directed to facilitating an infant's contact with select strains of bacteria, some for the infant's skin microbiome and others for the infant's gut microbiome, where in some embodiments, such bacterial strains are first provided on a mother's vagina so as to make such infant contact occur at the time of the infant's birth. As described herein, other forms of administration can also be employed, e.g. wipes provided with specific bacterial compositions, prebiotics, post-biotics, etc. such that an infant's skin is wiped with the same to confer colonization with beneficial bacteria.

There are different theories with respect to how an infant's microbiome is initially colonized, however, it appears that initial colonization largely occurs during vaginal or C-section birth, while acknowledging the importance of breastmilk, skin and feces bacteria transferred by a mother to her infant. In various embodiments of the present invention, infants are provided with bacteria to initiate or enhance the infant's colonization with *Escherichia, Staphylococcus, Bifidobacterium* and/or *Lactobacillus*, which preferably leads to a transition of the infant's gut microbiome to being dominated by *Bifidobacterium* microbiota due to milk consumption, and which shifts toward an adult-like microbiota when solid food is then introduced.

A decrease in *Veillonella* and/or *Lachnospira* bacteria is believed to reduce the risk of developing infantile asthma, wheezing and allergies. As such, certain embodiments of the present invention are directed to reducing these bacteria in a woman's vagina during the last stages of pregnancy so as to limit contact by such bacteria with a newborn infant. As described herein, there are various methods that may be employed to achieve such bacterial reduction without adversely affecting the survival of beneficial bacteria in a woman's vagina.

Certain other embodiments of the present invention are directed to the benefits to be derived from an increase in small chain fatty acid (SCFA) production by bacteria in a female's gut microbiome, while decreasing SCFA production in the individual's vaginal microbiome. While not bound by theory, the benefits provided by the bacterial production of various SCFAs, and in particular butyrate, such as via maintaining a population of *F. prausniitzi* in an individual's gut, are widely acknowledged as significant. Thus, many would mistakenly believe that in view of such health advantages, it would similarly be desirable to increase the production of SCFAs in other microbiomes, such as the vaginal microbiome. Aspects of the present invention, however, involve the modification of an individual woman's gut and vaginal microbiomes to increase SCFA production in the former and reduce it in the later.

The average healthy pH of the vagina is around 4±0.5. The low pH of the human vagina is quite unique as compared to other mammals, in which the vaginal pH ranges from 5.4 to 7.8. The main reason for this high acidity in humans is likely the dominance of lactobacilli. More than 70% of the bacteria in the human vagina are lactobacilli, while in other mammals this only accounts for 1%. In humans, the vaginal pH inversely correlates with the amount of lactate present. It is thus of importance in various embodiments of the present invention to adjust and maintain the pH of the vagina to be sufficiently acidic to allow lactic acid to exist and exert its protective qualities. During periods of bacterial vaginosis, the pH of the vagina typically increases, as well as the levels of some SCFAs.

The immunomodulatory roles of microbiota-generated SCFAs are different in the gut and vagina. SCFAs produced in the gut promote health, e.g. a rise in *Lactobacillus* and low pH, homeostasis, etc. In contrast, an increase SCFAs in the female reproductive system leads to a decrease in the Lactobacilli population and lactic acid concentration, which increases vaginal pH. Overall, an increase of SCFAs in the female reproductive system leads to mixed anaerobic populations and induces inflammation. These mixed anaerobic populations include *Streptococcus, Bacteroides, Gardnerella Prevotella, Mycoplasma, Ureaplasma, Finegoldia*, Mobiluncus, Leptotrichia, Eggerthella, *Veillonella*, Dialister, Atopobium, Megasphaera, Sneathia, Clostridiales BVAB 1-3, etc., that are seen in female genital tract diseases, such as BV and vulvovaginal candidiasis.

Anaerobes associated with BV can produce SCFAs in the women reproductive system through the fermentation of carbohydrates and amino acid catabolism. SCFAs in the female genital tract include propionate, acetate, isovalerate, isobutyrate, and n-butyrate. Collectively, SCFAs can lead to proinflammatory and dysbiotic effects in the female reproductive system.

Aspects of various embodiments of the present invention involve the purposeful generation of SCFAs in an individual's gut by the provision of certain butyrate producing bacteria, while at the same time, reducing the generation of SCFAs in the individual's vaginal microbiome. Thus, in certain embodiments of the present invention, with respect to a woman's vaginal microbiome, the population of specific bacteria is enhanced, such bacteria selected from the group consisting of *L. crispatus, L. jensenii*, and *L. vaginalis*, while the number of specific bacteria in the vaginal microbiome, including *C. albicans* and *Gardnerella vaginalis*, which are often encountered in vaginal infections, are reduced. The reduction of the latter bacteria may be achieved in various ways, e.g. via the employment of bacteriophages, antibiotics and/or the preferred use of CRISPR systems as elsewhere described herein, thereby selectively reducing the numbers of such undesired bacteria without killing the beneficial bacterial residing in the vagina.

In various embodiments of the present invention, and in recognition that a woman's body has various microbiomes that possess different characteristics, but which collectively define many health issues for each individual, aspects of the present invention include addressing more than one of a person's microbiome at the same time. For example, a woman may benefit from the modulation of her gut microbiome, as well as her oral microbiome, skin microbiome and vaginal microbiome. Instead of merely focusing on a single microbiome of an individual, various embodiments of the present invention are directed to addressing concerns that exist with at least two, and preferably at least three of the above-mentioned microbiomes of an individual—at approximately the same time. Perhaps surprisingly, certain beneficial attributes of one microbiome are not the same, and in some situations, are contrary to, the beneficial attributes of another microbiome from the same individual. For example, while it is increasingly viewed as a positive attribute for an individual's gut microbiome to possess bacteria that generate SCFAs, and in particular butyrate, this is not the case with respect to the vaginal microbiome of a woman, where an increase in production of SCFAs leads to an undesired acidity of the vagina, often leading to the growth of pathogenic bacteria, undesired biofilms, etc. Thus, certain embodiments of the present invention are directed to the modulation of two microbiome's of an individual at appropriately the same time, but whereby the modulation of one microbiome is to increase the quantity of SCFAs in a particular microbiome (e.g. one's gut microbiome), while at the same time, reduce the amount of SCFAs in another of the individual's microbiome (e.g. a woman's vaginal microbiome).

In the vaginal microbiota, microbial communities with a higher proportion of facultative and obligate anaerobes and low *Lactobacillus* species are associated with elevated inflammatory cytokine levels. Thus, certain embodiments of the present invention are directed to modulating the vaginal microbiome so as to increase the quantity of certain *Lactobacillus* species while decreasing the population of other bacteria that adversely affect the vaginal microbiome. For example, contrary to an individual's gut microbiome, which is benefited by the increased production of SCFAs, in various embodiments of the present invention, the amount of SCFAs is limited via the reduction of certain bacteria that produce SCFAs, and in particular lowering the amount of *F. prausnitzii* in a woman's vaginal microbiome.

Still other embodiments of the present invention are directed to modulation of various molecular factors that influence the resolution of inflammation, including but not limited to a prominent feature of the mucosal inflammatory microenvironment-hypoxia. Mucosal hypoxia promotes the active resolution of inflammation through a variety of mechanisms, including extracellular acidification, purine biosynthesis/salvage, the generation of specialized pro-resolving lipid mediators (i.e. resolvins) and altered chemokine/cytokine expression. Each of neutrophils, eosinophils, and macrophages play an important role in molding tissue microenvironments to program an active resolution response and dysregulation of such an inflammatory microenvironment results in the loss of tissue homeostasis. Rather than having a preferred *lactobacillus*-dominated vaginal microbiome, some women have a vaginal microbiome harboring a diverse community of anaerobic bacteria. In various embodiments of the present invention, probiotics and methods are used to reduce hypoxic conditions of a woman's vagina to thwart the populations of undesired anaerobic bacteria.

As described generally in related earlier applications, e.g. U.S. Pat. Nos. 9,408,88; and 9,457,007, one of skill in the art will appreciate that several embodiments of the present invention are directed to a suitable topical composition comprising a population of bacteria as described herein included in the form of a cream, lotion, emulsion, gel, ointment, liquid or spray. In one embodiment, the topical composition is formulated to provide at least about 10.sup.2 bacteria per cm.sup.2. In another aspect, a method of treatment is provided, wherein a composition as described herein is topically applied to the skin (e.g. vagina) of an expectant mother at around the time of birth, and also preferably during the first year of the baby's life. In certain embodiments, topically applying includes topically applying to a mucosal surface of the vagina of the expectant mother and/or directly to the new born baby or to the skin/nipple of the mother prior to breastfeeding the infant. In one preferred embodiment, a topical vaginal lotion comprises a mixture of *Lactobacillus johnsonii*, and *Bifidobacterium lognum* bacteria and is applied just prior to birth to provide an opportunity for the newborn to be first exposed to such bacteria, thus enhancing the chances that the baby's immune system will properly form in a manner that avoid allergies.

In certain embodiments, an initial step in the modulation of a woman's vaginal microbiome is to reduce if not eliminate the bacterium *Gardnerella vaginalis*, as its biofilm is recalcitrant and is believed to be central to the development of dysbiosis and is responsible for still further undesired pathobiont biofilms being formed in the vagina. Reduction of this bacterium by use of antibiotics, CRISPR systems, bacteriophages, etc. form one of several methods for reducing the number of *G. vaginalis* prior to the purposeful administration to and modulation of a woman's vagina with desired bacteria as referenced herein. Bacterial vaginosis (BV) is characterized by a depletion of *Lactobacillus* and an overgrowth of anaerobic and facultative bacteria, leading to increased mucosal inflammation, epithelial disruption, and poor reproductive health outcomes. Thus, the focus on reducing *Gardnerella vaginalis* and the administration of beneficial bacteria to a woman's vagina is one way to achieve a desired bacterial balance necessary for a healthy vaginal microbiome.

In accordance with another aspect of the present invention, certain embodiments are directed to a method that includes introducing ammonia oxidizing microorganisms (AOM) to a woman's vagina, and preferably live AOM. The ammonia oxidizing bacterium *Nitrosomonas eutropha* is employed in various embodiments of the present invention to enhance the health aspects of a woman's vagina. While *N. eutropha* bacteria is preferred in various embodiments, one of skill in the art will appreciate that other bacteria can be employed that have similar ammonia generation attributes, which may be provided to a given bacteria via the modification thereof, such as via use of a CRISPR system to include such functional characteristic.

In still other embodiments of the present invention, a baby's first bath is prepared such that it contains a concoction of a rich variety of *lactobacillus* and other immune enhancing agents to prevent the life-threatening diseases as discussed herein. In addition to a variety of various beneficial bacteria described herein, helminthes extracts, as also set forth or referenced herein, may be provided in a suitable lotion/ointment, that includes sugars that the various *lactobacillus* microorganisms may assimilate to survive and thrive. These sugars and bacteria supporting compounds are known to those in the art and as otherwise referenced in various incorporated writings. As certain spermicides and contraceptive creams can kill *Lactobacillus* species, it is one aspect of particular embodiments of the present invention to avoid the use of such formulations during pregnancy and during the first year of a newborn's life, as the prevalence of a rich variety of *lactobacillus*, as noted herein, is a desired objective to achieve in the overall environment of the expectant mother and the newborn for the first year of life. In this vein, preferably there is an avoidance of any type of aerosol sprays that could also kill bacteria in the environment of the expectant mother and the newborn.

A preferred bacteria that proliferates on the cocktail of compounds in mother's milk is *Bifidobacterium longum* biovar *infantis* (*B. longum* bv. *Infantis*). This bacterium is believed to enter the infant's intestinal tract in one of several ways, including when the fetus swallows amniotic fluid, when the fetus passes through the vaginal tract in a vaginal birth, and when the infant is provided with mother's milk. While there are hundreds of human milk oligosaccharides (HMOs) the *B. longum* bv. *Infantis* preferentially feast on the same to develop a colony of bacteria in the infant gut, thus leading to further enhancement of the developing immune system of the infant. The HMOs also directly ward off harmful bacteria, such as *Salmonella, Listeria* and *Campylobacter*. HMOs also mimic carbohydrate structures on the infant's gut and thus are believed to swamp the infant's system so that these dangerous bacteria bind to the HMOs rather than to the infant's developing gut, e.g. in a type of competitive defensive mechanism that is known in other natural systems. It is important to have a developed infant immune system that has a sufficient and significant number of *B. longum* bv. *Infantis*, which is correlated with the amount of mother's milk provided—but only if there is a resident and sufficient population of *B. longum* bv. *Infantis* in the first place. This bacterium makes up about 90% of the population of the gut of an infant, which is striking in that only about 3% of the adult gut is inhabited by this bacteria.

As one of skill in the art may appreciate, because the present inventors contend that there exist complexities with respect to the beneficial bacteria residing in a woman's vagina, as contrasted with the beneficial bacteria in an individual's gut, (for example, with respect to the amount of SCFAs produced by such respective bacteria and the benefits (or conversely the detriment) that are associated with such bacteria), this factor must be properly considered when formulating treatment plans for the modulation of each individual's particular microbiome. This is especially the case when one considers the vaginal seeding with bacteria that will presumably colonize the gut and skin microbiomes of infants. Thus, in certain embodiments of the present invention, a factor that has hereto been underappreciated, namely the importance of varying the bacterial type, amount and metabolites associated with a healthy vagina microbiome, while also taking into account the preferred bacteria that best benefits an infant's gut microbiome, one of skill in the art will recognize that subtle, but important, modulations of both the mother's vaginal microbiome and the infant's gut microbiome should be assessed, rather than simply believing that whatever microbiome the infant is exposed to by the mother is beneficial, let alone preferred. Stated differently, a desirable bacterial composition for a "normal" vaginal microbiome may not be the preferred bacterial composition to first colonize an infant's gut microbiome. For example, with C-section deliveries, attention should be paid to purposeful inoculation of an infant's microbiomes-including not just the infant's gut microbiome, but also its skin microbiome. Aspects of the present invention involve the administration to a newly born infant with a variety of pre-determined bacterial formulations for each of the infant's gut and skin microbiome, which in many cases, are not identical to the vaginal microbiome of the mother of the infant at the time of birth.

In preferred embodiments, certain microbes from the genus *Lactobacillus*, and more particularly, the species *Lactobacillus johnsonii*, are employed. *L. johnsonii* is a known human gut colonizer and becomes a dominant member of the maternal vaginal microbiome just before birth. In order to suppress allergic symptoms, it is believed effective to lean the immune balance towards "Th1-type" dominant, and generally, lactic acid bacteria are said to have an activity to lean the immune balance towards "Th1-type" dominant. In one embodiment, *Lactobacillus crispatus* KT-11 strain (FERM BP-11332) is used to lead the immune balance towards "Th1-type dominant", with such strain used in combination with other lactic acid bacteria belonging to the genus *Lactobacillus*, genus *Bifidobacterium*, genus *Leuconostoc*, genus *Enterococcus*, and genus *Pediococcus*.

While *L. johnsonii* is a preferred bacteria in many embodiments, other bacteria are employed in various embodiments, such bacteria selected from the group consisting essentially of *Lactobacillus acidophilus, Lactobacillus brevis, Lactobacillus buchneri, Lactobacillus casei, Lactobacillus delbrueckii, Lactobacillus fermentum, Lactobacillus helveticus, Lactobacillus kefir, Lactobacillus paracasei, Lactobacillus plantarum, Lactobacillus rhamnosus, Lactobacillus salivarius, Streptococcus thermophilus, Lactococcus lactis, Lactococcus plantarum, Lactococcus raffinolactis, Leuconostoc lactis, Leuconostoc mesenteroides, Enterococcus faecalis,* and *Enterococcus faecium*; an anti-allergic agent comprising as an active ingredient human-derived bifidobacteria selected from *Bifidobacterium infantis, Bifidobacterium breve, Bifidobacterium longum*, and *Bifidobacterium bifidum; Enterococcus faecalis* and *Lactobacillus reuteri*, and *Lactobacillus paracasei*.

In certain embodiments, a method for enhancing immunity of a newborn infant includes the use of a mixed culture of bacterial cells of three to eight species of lactic acid bacteria. In particular mixed cultures, the following may be included: *Saccharomyces cerevisiae, Lactobacillus delbrueckii, Lactobacillus acidophilus, Lactobacillus plantarum, Lactobacillus fermentum, Lactobacillus casei, Lactobacillus rhamnosus, Lactococcus lactis* and *Streptococcus thermophilus; Enterococcus faecium; Bacillus coagulans; Leuconostoc, Pediococcus, Lactobacillus casei, Lactobacillus plantarum, Lactococcus lactis* subspecies *lactis, Lactococcus lactis* subspecies *cremoris; Lactobacillus plantarum; Pediococcus pentosaceus; Streptococcus thermophilus; Lactobacillus paracasei; Lactobacillus plantarum, Lactobacillus gasseri* and *Lactobacillus salivarius; Lactobacillus acidophilus* PM-A0002, *Lactobacillus gasseri, Lactobacillus salivarius, Lactobacillus acidophilus* PM-A0013; *Leuconostoc mesenteroides; Lactobacillus bulgaricus, Lactobacillus rhamnosus, Lactobacillus acidophilus, Lactobacillus paracasei; Bifidobacterium bifidum; Lactobacillus brevis; Enterococcus durans, Leuconostoc mesenteroides; Lactobacillus crispatus*. Still other embodiments of the invention may comprise extracts obtained from one or more of the following species: *Lactobacillus fermentum, Lactobacillus rhamnosus, Lactobacillus plantarum, Lactobacillus johnsonii, Lactobacillus helveticus, Lactobacillus casei defensis, Lactobacillus casei* ssp. *casei, Lactobacillus paracasei, Lactobacillus bulgaricus, Lactobacillus paracasei, Lactobacillus acidophilus, Lactobacillus reuteri, Lactobacillus salivarius*, and *Lactobacillus lactis*. In some embodiments, at least one strain from each of the above species of bacteria is used, while in other embodiments, one or more specific strains from the list above may be removed or substituted with one or more different strains. In particular, some embodiments of the present invention comprise an extract obtained from one or more of the following bacterial strains: *Lactobacillus fermentum* I-3929, *Lactobacillus rhamnosus* 71.38, *Lactobacillus plantarum* 71.39, *Lactobacillus johnsonii* 103782, and *Lactobacillus helveticus* 103146. The strains above are deposited according to the Budapest Treaty. *Lactobacillus fermentum* I-3929, *Lactobacillus rhamnosus* 71.38, *Lactobacillus plantarum* 71.39, *Lactobacillus johnsonii* 103782, and *Lactobacillus helveticus* 103146 are each deposited at the Collection Nationale de Culture des Microorganismes at the Institut Pasteur, 25 rue du Dr. Roux, 75724 Paris, France. *Lactobacillus fermentum* I-3929 was deposited on Feb. 27, 2008. The other strains are among the depository's collections and may be obtained by contacting the depository. The following bacteria species may also be employed: *Lactobacillus acidophilus* PM-A0002 deposit number M 207038, *Lactobacillus* gasseri PM-A0005 deposit number M 207039, *Lactobacillus salivarius* PM-A0006 deposit number M 207040, *Lactobacillus johnsonii* PM-A0009 deposit number M 207041 and *Lactobacillus acidophilus* PM-A0013 deposit number M207042. Certain embodiments of the present invention involve the use of bacteria obtained from Amish manure-containing soils.

In preferred embodiments, the environment whereby the expectant mother is exposed is devoid of significant levels of lead. It is speculated that the metal lead is a common environmental pollutant in inner cities and in older houses, released from factories and during mining operations. It is believed that lead disrupts normal immune system development, leading to increased frequency of the development of allergies and asthma. Lead exposure during critical, prenatal periods of development can impact immune system function well after birth. It is speculated that in the presence of lead exposure, the fetal immune system is changed so it overreacts to common particles in the environment. Thus, one aspect of the present invention is to avoid exposure of an expectant mother to lead, while at the same time, exposing such mother to significant levels of microbes and fungi obtained and derived from farms having manure containing soil collected from certain Amish farms, especially those that do not employ significant amounts of antibiotics in treating their cows, sheep, pigs, goats or poultry. Similarly, it is one aspect of the present invention for the expectant mother to desist from the use of anti-bacterial soap, as such use is believed to inhibit the immunity conferring benefits to be derived from the present invention. It is further believed that bacteria and other microbes from soil containing manure from bovines raised by the Amish (as well as other farm animals) and where neither the animals nor the manure is treated with an anti-biotic, is more effective as a source of desired microbes and allergens responsible for conferring the protective immunologic attributes that pass from an expectant mother to her unborn child. In a preferred embodiment of the invention, the child, after he or she is born, is further exposed to the manure containing soil that the expectant mother was exposed to during the pregnancy. In such a manner, it is believed that the early exposure to allergens is reinforced and permits the immune system to fully protect the child from such allergens. In other words, the child's immune system is permitted to more fully mature under the influence of continued exposure to the same type of microbes and fungi as was the mother during pregnancy.

Incomplete resolution of inflammation negatively impacts a woman's reproductive health. In contrast to other mucosal sites, the structure and function of the female vagina is tightly regulated by ovarian sex hormones progesterone and estradiol as their levels fluctuate throughout the menstrual cycle. Such fluctuating sex hormone levels influence immune cell function.

In the vaginal microbiota, microbial communities with a higher proportion of facultative and obligate anaerobes and low *Lactobacillus* species are associated with elevated inflammatory cytokine levels. Thus, certain embodiments of the present invention are directed to modulating the vaginal microbiome so as to increase the quantity of certain *Lactobacillus* species while decreasing the population of other bacteria that adversely affect the vaginal microbiome. For example, contrary to an individual's gut microbiome, which is benefited by the increased production of SCFAs, in various embodiments of the present invention, the amount of SCFAs is limited via the reduction in the vagina of certain bacteria that produce SCFAs, and in particular lowering the amount of bacteria that produce SCFAs, especially butyrate, in a woman's vaginal microbiome. SCFAs are the predominant metabolites in dysbiosis of the vaginal tract. Thus, lactic acid and SCFA metabolites represent biomarkers of disease in the vagina, while in the human gut, SCFAs have an anti-inflammatory role by inhibiting proinflammatory cytokines.

Lactobacilli including *L. crispatus, L. gasseri, L. iners, L. jensenii*, etc, are desirable because of protective properties, which include the production of lactate to lower vaginal pH and the production of bacteriocin and hydrogen peroxide, which provide an antimicrobial environment for pathogenic microorganisms and limit their growth. Lactobacilli break maltose into lactic acid in the glycolysis pathway in anaerobic conditions which regulate the vaginal pH lower than 4.5 and are responsible for vaginal acidity in healthy women. Lactic acid and hydrogen peroxide ($H_2O_2$) production by Lactobacilli and low pH are anti-microbial factors that protect against the colonization of pathogens. In various embodiments of the present invention, preferred concentrations of lactic acid are as high as 120 mM in the lower genital tract, with a concentration of acetic acid of 0-4 mM. In certain embodiments of the present invention, a topical application of *Lactobacillus crispatus* to an individual's vagina is done to reduce inflammation through production of tryptophan metabolites.

In dysbiotic vaginal conditions, certain undesired bacteria, such as *Prevotella, Gardnerella, Bacteroides*, Mobiluncus, Atopobium, *Mycoplasma, Ureaplasma, Sneathia, Streptococcus*, Eggerthella, Dialister, Leptotrichia, *Finegoldia, Megasphaera, Veillonella*, and Clostridiales are often dominant and these anaerobes species do not produce much lactic acid, instead they break glycogens into glucose and SCFAs metabolites, such as butyrate, propionate, succinate, and especially acetate. BV-associated anaerobes species are responsible for the fishy odor of vaginal discharge and can generate virulence factors that can stimulate immune responses. When vaginal pH elevates more than 4.5, epithelial barrier integrity is compromised, mucin degrades, and therefore BV and other female genital tract disorders increase.

SCFAs influence the immune system's operation by boosting T and B cell differentiation to control antigen-specific adaptive immunity and inhibiting dendritic cell migration and activation to reduce allergies. SCFAs have a positive effect on the gut mucosa by enhancing epithelial integrity, differentiation, and proliferation as well as decreasing the release of pro-inflammatory chemicals from mucosal epithelial and immune cells. But they are not deemed in a positive light with respect to their function in the female genital tract mucosa. Vaginal and cervical epithelial cells secrete pro-inflammatory molecules in response to high amounts of SCFAs and thus exacerbate, rather than alleviate, mucosal barrier functions and BV problems.

Mucus is one of the essential elements of the barrier function at the mucosa of the female reproductive system. *L. crispatus*-dominated vaginal microbiota capture microorganisms more effectively compared to mucus associated with vaginal microbiota dominated by Gardenella and *L. iners*. But mucus can become impaired if BV-associated bacteria degrade it. For example, a beneficial component of the mucus in the female reproductive system, sialic acid, is aggressively degraded by *Prevotella, Gardnerella*, and *Bacteroides*. Thus, in certain embodiments of the present invention, one step includes the reduction in the populations of one or more of *Prevotella, Gardnerella*, and *Bacteroides* in the vaginal microbiome to preserve the mucus in the vagina.

High concentrations of SCFAs cause vaginal epithelial cells to produce pro-inflammatory mediators. Higher concentrations of SCFAs in the human vaginal along with a decrease in lactate in BV leads to microbiota dysbiosis, which results in pathogen growth and can cause infection, leading to adverse reproductive outcomes such as miscarriage and preterm birth.

In contrast to the vaginal microbiome, Firmicutes and Bacteroidetes make up more than 90% of all the gut microbiota. The most abundant bacterial species in the gut of healthy adults is *Faecalibacterium prausnitzii* of the Firmicutes phylum. In the gut microbiome, Firmicutes species are the main butyrate producers, while Bacteroidetes species are the main acetate and propionate producers in the gut. In contrast to the gut, the predominant organic acid in a healthy vagina is lactic acid. The transfer of microbes between gut and vagina is possible, and so one would think the microbial composition of both would be similar. However, due to differing characteristics of these two microbiomes, different species thrive and become dominant in each, such that while the metabolites lactate, acetate, butyrate, succinate and propionate are present in both microbiomes, they exist in completely different concentrations and reflect contrary health conditions.

In still other embodiments of the present invention, a woman's vagina is administered a therapeutically effective amount of tomatidine to achieve benefits that are related to the intrinsic properties of tomatidine, such as its involvement in causing cell growth, and in its defense against pathogenic bacteria, viruses and fungi. Especially when administered in conjunction with bacterial species as identified herein, for example, AOM bacteria, the combination of tomatidine and such bacteria is believed to enhance the health of a woman's vaginal microbiome:

SCFA and lactate are also implicated in the onset of infection and virulence of fungal pathogens, such as *Candida*. Thus, one aspect of various embodiments of the present invention involves the reduction in the amount of SCFA production by vaginal bacteria to reduce the population of *Candida*.

Preferably, in various embodiments of the present invention, women are administered vaginal microbes of the aerotolerant anaerobic *Lactobacillus* bacteria, specifically *L. crispatus, L. gasseri, L. iners*, and *L. jensenii*. In contrast to other microbiomes, with respect to the vaginal microbiome, non-diverse *Lactobacillus* dominated microbiomes are considered healthy. As lactobacilli make up the vast majority of the vaginal microbiome, a large amount of metabolites present in the vaginal niche, mainly lactate, are produced by these species. *L. crispatus* dominated microbiomes have a high lactate content. While lactate is the main fermentation end product of lactobacilli, *L. jensenii* also produces high amounts of acetate and succinate.

BV-associated species are responsible for producing SCFAs and during BV, lactate levels are lowered, while the concentration of SCFA increases. BV-associated species that produce organic acids are: Peptococcus (butyrate and acetate production), Dialister (propionate production), *Gardnerella vaginalis* (acetate and succinate production), Bacteroides (succinate production), gram-positive cocci, and *Clostridium* (caproate production). Thus, certain embodiments of the present invention are directed to the selective reduction in the number and population of these BV related bacteria.

In particular embodiments of the present invention, tomatidine is administered to a woman to enhance the health of her vaginal microbiome. Such administration may be either oral or vaginal- or both. It is believed that tomatidine has an anti-atrophic (anabolic) effect in skeletal muscle and possesses anti-hyperlipidemic and anti-atherosclerotic effects without evidence of toxicity. Tomatidine is associated with anti-apoptotic, anti-inflammatory, anti-bacterial, and anti-cancer properties and appears to suppress inflammation by inhibiting the NF-κB and JNK signaling pathways.

In other embodiments of the present invention, in addition to the described bacterial formulations set forth, rapamycin is included to enhance the health of a woman's vaginal microbiome. Rapamycin targets is a kinase called mTOR which plays a role in a variety of biological pathways. Rapamycin is an inhibitor of mTOR complex (mammalian target of rapamycin) which is a serine threonine kinase and a master regulator of protein synthesis, cell growth, and cell metabolism. Excessive mTORC1 activity has been implicated in multiple disease conditions, as well as various cancers, inflammatory bowel disease, inflammatory skin diseases and neurodegenerative diseases. In various embodiments of the present invention, rapamycin is employed, especially in combination with other agents, e.g. tomatidine and xylitol, to treat, prevent and to reduce the likelihood of an individual suffering from vaginal disorders and diseases.

In various embodiments as described herein, administration of therapeutically effective amounts of rapamycin, e.g. by vaginal administration, is employed to combat disorders associated with age.

In certain embodiments, DNA encoding pre-cursors for the biosynthesis of tomatidine, xylitol and/or rapamycin is inserted into the genome of one or more bacterial species by employing CRISPR-Cas or CPf1 systems, such that an individual can orally take a pill containing such modified bacteria and in such a manner, effectively administer tomatidine, xylitol and/or rapamycin to the individual in a manner that does not require injections or the taking of traditional pharmaceutical formulations. Administration of rapamycin may be performed to affect about 0.001 mg to 30 mg total per day as an effective dose, preferably at least about 0.1 mg per day, with a preferred blood level of rapamycin in the subject being about 0.5 ng per mL whole blood after administration of the composition after a 24 hour period.

One embodiment of the present invention is directed to a bioadhesive strip adapted to bind to a mucosal membrane for at least 1 hour while inside a woman's vagina where the strip includes tomatidine and xylitol in therapeutically effective amounts, E.g. at least 10 micro-mole of tomatidine and at least 200 mg of xylitol or at least 0.2% xylitol by weight. In preferred embodiments, the strip includes at least one polymer selected from the group consisting of pullulan, hydroxypropylmethyl cellulose, hydroxyethyl cellulose, sodium alginate, polyethylene glycol, tragacanth gum, guar gum, acacia gum, arabic gum, carboxyvinyl polymer, amylose, high amylose starch, hydroxypropylated high amylose starch, dextrin, chitin, chitosan, levan, elsinan, collagen, zein, gluten, soy protein isolate, whey protein isolate, casein and mixtures thereof. In other embodiments, such strips may also include the beneficial vaginal bacteria described herein, as well as pre- and post biotic materials to maintain populations of such bacteria in the vagina.

Certain embodiments of the present invention are directed to treating vaginal dysbiosis so as to forestall women from experiencing serious infections. The various *Lactobacillus* probiotics as described herein are employed to reverse vaginal microbiota dysbiosis by facilitating the colonization of certain *Lactobacillus* species in a woman's vagina. For example, in certain embodiments, a combination of *Lactobacillus acidophilus, Lactobacillus rhamnosus*, and *Lactobacillus reuteri* are employed, in combination with a composition containing carbohydrates that feed such bacteria and promote their growth in a woman's vagina, all the while monitoring that the pH of the vagina does not exceed 4.5. While such compositions may be vaginally administered, they may also be administered orally, to improve vaginal health.

The gut, vaginal, and urinary microbiomes are mutually influential, and dysbiosis of one of these microbiota may result in several health problems. Menopause alters the gut, vaginal, and urinary microbiota due to drastic hormone changes. The gut microbiome of women influences bone metabolism and has a profound effect on bone quantity, quality. and overall strength. The gastrointestinal tract contains the highest concentration of immune cells that communicate with the microbial community, which triggers a release of metabolites that affect the immune system directly. The intestinal epithelial barrier plays a crucial role in separating the internal structures, with intestinal epithelial cells being sealed by light junction proteins, such as ZO-1, claudin-1, and occludin. One aspect of various embodiments of the present invention is directed to altering the expression of tight junction proteins to alter the permeability of the intestinal barrier. If the intestinal barrier is breached, it allows microorganisms to enter the subepithelial structures from the intestinal metastatic lumen, and triggers an inflammatory response, often resulting in the development of osteoporosis, especially in postmenopausal women. Various embodiments of the present invention are directed to increasing probiotic function to increase the strength of the intestinal epithelium by upregulating tight junction proteins, reducing antigen presentation and activation of intestinal immune cells.

One aspect of many embodiments of the present invention is directed to modulation of the changes in a woman's microbiome, and in particular the vaginal microbiome, due to postmenopausal changes to alleviate and control postmenopausal health. Menopause-induced hormonal changes significantly alter the gut microbiome and hormone therapy can restore the microbiome to some degree. In various embodiments of the present invention, bacteria are administered to women to reduce the pH of their vaginas where the reduction of estrogen production has resulted in an increase of vaginal pH. This is accomplished by the administration of bacteria that affect the vaginal pH, notably the administration of *Lactobacillus* so as to positively influence the changes that are otherwise observed in vaginal structure and function in view of the onset of genitourinary syndrome of menopause. Menopause alters the gut microbiota, which has several effects on a woman's health. Moreover, the urinary microbiome plays an important role in urinary tract disease in the ovulatory cycle and certain hormones have substantial effects on the composition of such microbiome. Estrogen and progesterone cause thickening of the stratified squamous epithelium of the vagina and the deposition of glycogen. Alterations in the microbiota due to postmenopausal hormone changes are similar to vaginal dysbiosis observed in inflammatory pelvic disease, human immunodeficiency virus and human papillomavirus (HPV) infections, and pregnancy. Urinary pathogens are believed to originate in the gastrointestinal tract, with an intermediary step of vaginal colonization. Therefore, changes in the gut and vaginal microbiome as a result of dramatic hormonal changes during menopause impact the urinary microbiome. As disclosed herein, the modulation of both a woman's gut and vaginal microbiomes, with the understanding that the levels of SCFAs are distinct in each, forms one aspect of various embodiments of the present invention.

Postmenopausal women have a higher Firmicutes/Bacteroidetes ratio and a higher relative abundance of *Lachnospira* and *Roseburia* compared to premenopausal women, while premenopausal women have a lower relative abundance of the *Prevotella*, Parabacteroides, and Bilophila genera. Increased Bilophila in menopausal women leads to increased hydrogen sulfide production, inducing local inflammation and mucosal damage, increased serum endotoxin concentrations, and inflammatory reactions in several types of tissues. Thus, various embodiments of the present invention are directed to modulation of an individual's microbiome to address such changes by effective administrations of particular bacteria to distinct microbiomes.

Various embodiments are directed to balancing a woman's microbiome by increasing populations of gut microbiome bacteria to address an imbalance due to a deficiency of *Aggregatibacter segnis, Bifidobacterium animalis*, and *Acinetobacter guillouiae*. Moreover, other embodiments are directed to increasing populations of *Romboutsia, Mollicutes*, and *Weissella* spp. and in reducing populations of *Fusicatenibacter, Lachnoclostridium*, and *Megamonas* spp.

Certain aspects of the present invention are directed to methods for determining particular bacterial species, specifically those of *Bifidobacterium*, using computational biology to associate consortia with health span and longevity, thus permitting the treatment of age-related diseases. For example, certain methods employ a temporal microbiome characterization of healthy individuals-such as during the first and last stages in life—to elucidate *Bifidobacterium* that are most likely to confer health benefits.

Certain aspects of the present invention are directed to the mitigation of the decline of *Bifidobacterium* in the underlying mechanisms of aging. Bifidobacteria are gram-positive, anaerobic, non-motile, non-spore-forming, polymorphic rods that belong to the family Bifidobacteriaceae, order Bifidobacteriales and phylum Actinobacteria. The genus *Bifidobacterium* encompasses approximately 80 species, including four species *Bifidobacterium animalis, B. longum, B. pseudolongum* and *B. thermacidophilum*. In addition to the presence in the human gut, bifidobacterial species are present in the human vagina. Certain aspects of the present invention are directed to modulation of an individual's microbiome by increasing the population of bifidobacterial species in a woman's vagina.

Still other embodiments of the present invention are directed to increasing the populations of bacteria in one or more of the genera *Lactobacillus, Brevundimonas*, and *Odoribacter* while decreasing the quantity/populations of bacteria in the genus *Streptococcus*, thus treating women suffering from premature ovarian insufficiency.

In various embodiments, retention of the normal bacteria flora in terms of species of bacteria is preferred, but while maintaining such diversity of bacteria, the particular strains of such species are modified so as to reduce levels of undesired compounds normally generated by such bacteria, while at the same time maintaining, if not increasing, the level of desired products.

Various embodiments of the present invention are directed to increasing/enhancing the population in a woman's vagina of *Lactobacillus*, and more preferably at least two, and preferably at least three of the following: *Lactobacillus crispatus, Lactobacillus iners, Lactobacillus jensenii*, and *Lactobacillus* gasseri.

The antimicrobial effect of lactic acid is strongly pH dependent as only the protonated form of the acid has antimicrobial properties. At slightly higher pH, lactate does not exhibit similar antiviral nor antibacterial activity.

Lactobacilli are the dominant microbiota in the vagina and the administering of prebiotics can stimulate the growth of lactobacilli so as to maintain the preferred flora of the vaginal ecosystem. For example, in certain embodiments, prebiotic oligosaccharides are employed to support the probiotic properties of *L. crispatis, L. jensenii* and *L. vaginalis*.

The functional contributions of bifidobacteria to health and well-being of adults is largely unexplored, and thus, aspects of the present invention are directed to microbiota enrichment with rationally selected strains of *Bifidobacterium* more adapted to the adult host, and especially the roles played by *Bifidobacterium* in the gut ecosystem across various host ages, and specifically with respect to *Bifidobacterium animalis* subsp. *Lactis*, and *Bifidobacterium adolescentis*, with modulation of an individual's gut microbiome to reflect that such bacteria are present in at least 20% of relative abundance in an individual's gut microbiota. Thus, various embodiments are directed to the purposeful enrichment of the adult gut microbiota with *Bifidobacterium* to support short- and long-term human health.

In still further embodiments, in addition to increasing levels of butyrate provided to an individual's gut microbiome so as to achieve the various benefits as described herein, some embodiments include the provision of tributyrin, preferably via a fermented form of tributyrin. Tributyrin is an organic compound having the chemical formula $C_{15}H_{26}O_6$. Butyrate is the conjugate base of butyric acid while tributyrin is a prodrug of butyric acid, with a preferred IUPAC name Propane-1,2,3-triyl tributanoate. In such a manner, it is possible to provide individuals with a direct delivery of butyrate to the large and small intestine via cleaving by a lipase. Thus, while several embodiments of the present invention involve providing bacteria to an individual so as to produce/generate SCFAs in their gut microbiome, namely butyrate, other embodiments include an exogenous method of increasing butyrate in the gut of an individual that is independent of butyrate-producing bacteria, fiber requirements, etc. In certain preferred embodiments, at least about 300 mg of tributyrin is provided to an individual of the fermented form of tributyrin, more preferably at a level of at least about 500 mg, and even more preferably by providing doses in the 500-1000 mg range. In a similar manner, other embodiments involve the provision to an individual of both tributyrin and tracetatin (e.g. acetates bound to glycerol) in combination. While not bound by theory, it is believed that a combination of acetate and butyrate, as well as other SCFAs, provide health benefits to an individual. In preferred embodiments, methods of the present invention involve the provision of around a 1:3 ratio of triacetin and tributyrin, e.g. (250 mg triacetin+750 mg tributyrin) which is preferably orally delivered/administered to promote bone health and to maintain optimal levels of SCFA levels during aging. In addition to butyrate, one of skill in the art will appreciate that in other variants of the present invention, one may use sodium butyrate (having a chemical formula $Na(C_3H_7COO)$) to achieve various objectives, as it is the sodium salt of butyric acid. Such objectives include the inhibition of proliferation, induction of differentiation, and/or induction of the repression of gene expression. Similarly, calcium magnesium butyrate can be employed in other embodiments of the present invention as it is more stable than sodium butyrate and is less hygroscopic.

Certain embodiments of the present invention are directed to establishing in an individual a mutually symbiotic flora of microorganisms, in particular of the genus *Lactobacillus*, able to colonize a healthy vagina, thereby protecting its host from vaginal infections. The acidity of a healthy vagina of a woman is due to the degradation of secreted glycogen/glucose to lactic acid and acetate by lactobacilli, providing for conditions that are unfavorable for the growth of many pathogenic microorganisms. An imbalance in the vaginal microbiota may result in overgrowth of pathogenic microorganisms, resulting in dysbiosis, inflammation and/or infections, leading to vaginitis, bacterial vaginosis, vaginal candidiasis and trichomoniasis. Thus, certain embodiments are directed to achieving and maintaining a balanced environment in a woman's vagina to reduce or deter the growth of pathogenic microorganisms and to foster the growth of beneficial bacteria. In certain embodiments, this is accomplished by employing novel compositions and methods that include live biotherapeutics to treat individuals based on differences between a gene-specific characterization of an individual's microbiome and a reference gene catalog of a human microbiome. Still other methods involve the purposeful colonization of a woman's vagina with beneficial bacteria just prior to a baby's birth so that the newborn baby is primarily exposed to such bacteria to foster the robust development of an immune system, believed to avoid the prospect of allergies, asthma, multiple sclerosis, type-1 diabetes, and other autoimmune diseases from developing by the infant.

Menopause alters the gut, vaginal, and urinary microbiota due to drastic hormone changes. To address such issues, several embodiments of the present invention are directed to administering bacteria to women during menopause to reduce the pH of their vaginas, thus effecting a reduction of estrogen production that is a result of an increase of vaginal pH. Other aspects of various embodiments involve reducing the prospects of osteoporosis by combatting the disruption of bone metabolism due to the increased expression of pro-inflammatory factors, including methods that employ administration to an individual of particular beneficial bacteria, tomatidine, etc. Such bacterial formulations reduce the likelihood of degenerative joint disease, chronic pain and disability involving articular cartilage breakdown, synovial inflammation, and bone hypertrophy.

Antibiotic exposure of a mother can affect the maternal vaginal microbiome composition and thus, has an effect on neonatal stool microbiomes. While there is some debate about the value of "vaginal seeding" to affect, restore and/or maintain an infant's microbiome, the present inventors believe that the presence of antibiotic exposure severely warps the ability to properly analyze the situation. Thus, while some believe that vaginal seeding appears to be transient and only evident immediately after birth prior to the impact of breastfeeding and other environmental exposures, the present inventors contend that such infant exposure to beneficial microbes has as yet unappreciated benefits to the infant. Together with beneficial bacteria being administered, e.g. via other maternal microbiomes, such as those of the breast milk and maternal gut, vaginal seeding with compositions of the present invention are believed to be valuable and worthwhile, particularly with respect to the vertical transfer of maternal strains to the early intant gut. While not bound by theory, it is believed that the purposeful modulation of the vaginal microbiome prior to a baby's birth, can trigger life-long immune responses, thus affecting the infant's ability to naturally develop its immune system in a manner that precludes the later suffering of asthma, allergies, etc. Identical strains from the genera Ruminococcus, *Bifidobacterium, Bacteroides* and members of the Clostridiales order have been identified in mother-infant pairs by multiple independent groups in the early days and weeks of life. Certain embodiments of the present invention are directed to providing at least two of these bacteria and contacting a woman's vagina therewith prior to the birth of her baby so as to ensure contact between the baby and the seeded vagina during the birthing process.

Certain aspects of the present invention relate to the appreciation that a healthy vaginal microbiome can be dominated by *Bifidobacterium* sp., a group of Gram-positive, anaerobes that are known to colonize the human vagina, oral cavity, and the gastrointestinal tract where they play an important role in the protection from pathogens through the production of bacteriocins. *Bifidobacterium* are capable of producing lactic acid and tolerate a low pH, important in maintaining a healthy vaginal fluid. Thus, certain embodiments of the present invention include compositions of both *Bifidobacterium* spp. and *Lactobacillus* spp. to achieve the desired result of preventing vaginal colonization by pathogenic organisms.

In certain embodiments, a particular microbial composition is employed comprising three distinct *Lactobacillus crispatus* strains, LUCA009, LUCA011, and LUCA103, (preferably all isolated from the human vaginal tract of healthy women, referred to herein as VM-02 as a functionally defined microbial composition). Preferred embodiments provide formulations that are rationally designed vaginal synbiotic formulations such that data may be generated demonstrating the coexistence and exertion of biological activity in the human urogenital system. The underlying concept to create a proactive approach rather than reactive care for vaginal health needs is unique from empiric approaches employed in the global probiotics category. In preferred embodiments, a live consortium is delivered as a suppository with additional ingredients which provide a supportive vaginal environment and serve as growth substrates for the bacterial strains.

Bacterial formulations of various embodiments are formulated based on (i) intra-species genetic diversity/pan-genomic coverage within the consortium, which confers temporal stability of the healthy microbiota (ii) resilience of the vaginal microbial community against fluctuations, such as menses and pathogen introduction, (iii) genetic synergy, following ecological principles that enable the strains' persistence and co-functionality; and (iv) strains which play a key role in the healthy vaginal ecosystem via acidification and production of antimicrobial compounds.

In contrast to prior art technologies that utilize a single strain of *Lactobacillus*, in preferred embodiments at least three strains are employed based on the genomic and metabolomic driven reconstitution of a vaginal microbial ecosystem consisting of multiple strains with minimal non-redundant genes. In one preferred embodiment, VM-02 is employed to achieve a desired balanced vaginal microbiome so as to promote and foster improved vaginal health. In various embodiments, an objective is to target an underlying microbial dysbiosis with an interventional probiotic to change the microbial composition, resulting in achieving an optimal vaginal health status through a conversion to a protective vaginal microbiome community state. Thus, in various embodiments an objective is to provide a multi-strain symbiotic intervention that is safe, well-tolerated, and an efficacious means to improve vaginal health. The result of employing such technology is the achievement of a conversion to a more protective vaginal microbiome community state, even in healthy, using an interventional probiotic, and with the delivery vehicle and mode of administration being a key component for successful strain persistence.

The vagina is the most likely source of bacteria that infects the urinary tract. A healthy vaginal microbial environment, however, is believed to decrease the risk of rUTI. A unique set of *Lactobacillus* species play key protective roles against pathogens in the vagina by lowering the environmental pH through lactic acid production, producing various bacteriostatic and bactericidal compounds, and by competitive exclusion. *Lactobacillus crispatus* species is generally considered to be associated with health, as it does not induce a vaginal mucosal inflammation, and it is also associated with protection from pathogens.

In a preferred embodiment, vaginal suppository is employed to modulate the vaginal microbiome to a state non-permissive to reinfection. The vaginal suppository is preferably supported by an oral monosaccharide, D-mannose, that acts locally, once excreted into the urinary tract to prevent binding of a causative pathogen to uroepithelial cells.

One will appreciate that this Summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, figures, etc. will provide a basis for the scope of the present invention as it may be claimed now and in future applications. While embodiments of the invention have been illustrated and described, it is not intended that these embodiments illustrate and describe all possible forms of the invention. Rather, the words used in this specification are words of description rather than limitation, and it is understood that various changes may be made without departing from the spirit and scope of the invention.

BRIEF DESCRIPTION OF THE FIGURES

FIG. 1 is an illustration of *L. crispatus*.

FIG. 2 is an illustration of *Faecalibacterium prausnitzii*.

FIG. 3 is an illustration of *Roseburia*.

FIG. 4 is an illustration of *Veillonela*.

FIG. 5 is an illustration of *Prevotella*.

FIG. 6 is an illustration of *L. reuerti*.

FIG. 7 is an illustration of *I. johnsonii*.

FIG. 8 is an illustration of *N. eutropha*.

FIG. 9 is an illustration of *Odoribacter*.

FIG. 10 is the chemical formula for xylitol.

FIG. 11 is the chemical formula for rapamycin.

DETAILED DESCRIPTION OF EMBODIMENTS OF THE PRESENT INVENTION

Figure 12:
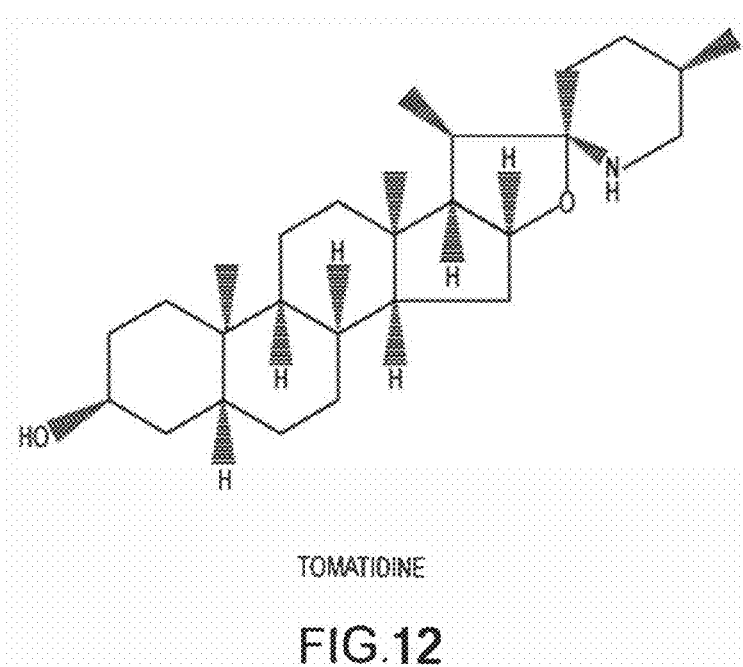
FIG. 12 is the chemical formula for tomatidine.

As used herein, the terms "effective amount" and "amount effective" refer to an amount that is sufficient to achieve the desired result or to influence an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products, such as xylitol, rapamycin and tomatidine. In further various aspects, a preparation can be administered in a "prophylactically effective amount"; that is, an amount effective for prevention of a disease or condition. In various embodiments, an effective amount of rapamycin may be 50 to 250 micrograms; or between 0.1% to 20% of rapamycin based on total weight of the formulation; or at least 0.1 mg of rapamycin; or a dose of rapamycin in the range of 1 mg/day to 5 mg/day, and in other embodiments, in the range from about 0.01 .mu.g/day to about 50 .mu.g/day. In certain embodiments, the effective amount of tomatidine is at least 10 micro-mole of tomatidine; and at least 200 mg of xylitol or at least 0.2% xylitol by weight.

In certain embodiments of the present invention, a topical application of *Lactobacillus crispatus* to an individual's vagina is done to reduce inflammation through production of tryptophan metabolites. It is believed that such tryptophan metabolites act as AHR agonists. One of skill in the art will appreciate that embodiments may incorporate live bacteria, metabolites of these bacteria, postbiotics from these bacteria, and/or heat killed bacteria. In one particular embodiment, live bacterial cells of *Lactobacillus crispatus* are administered to an individual's vagina at a dosage of at least 10.sup.8 CFU, preferably in a moisturizing topical formulation, so as to reduce inflammation through the localized production of tryptophan metabolites. While not bound theory, it is believed that the localized production of tryptophan metabolites by *L. crispatus* acts as AHR agonists in keratinocytes. Preferably the *L. crispatus* bacteria formulation is further combined with a source to maintain the bacteria for a pre-determined time. In certain embodiments, such a formulation includes glycogen. In still other embodiments, a prebiotic for *L. crispatus* is provided, such prebiotic which may also include glycogen, and even more preferably it further includes a stimulant for the production of ceramide by keratinocytes. One or more skin moisturizing agents may be included, including, for example, skin barrier integrity-enhancing ingredients, such as PEA/MEA bioactive lipids, N-acetyl cysteine, nicotinamide, luteolin, and/or madecassoside. Again, while not bound by theory, bacterial formulations of the present invention include at least one bacteria that generates metabolites that act as AHR agonists. Preferred metabolites comprise tryptophan metabolites, such as indole-3-aldehyde or indole-3-acetic acid, as well as those that may reduce inflammation and/or those that inhibit thymic stromal lymphopoietin (TSLP) in keratinocytes in an AHR dependent manner. It is believed that AhR activation may suppress upregulation of TSLP expression. In preferred embodiments, *L. crispatus* is employed under conditions such that specific metabolites are generated that act as AHR agonists, thereby resulting in the reduction of vaginal inflammation. In preferred embodiments the metabolites generated via the use of *L. crispatus* comprise tryptophan metabolites, including at least one of the following: indole-3-acetic acid, Indole-3-ethanol, Indole-3-pyruvate, indole-3-aldehyde. Thus, aspects of various embodiments of the present invention include the use of a live bacterial topical probiotic product that modulates AhR expression through the localized production of tryptophan-derived bacterial metabolites. Preferred topical formulations include a combination of live *L. crispatus*, prebiotic glycogen, and at least one barrier-enhancing/moisturizing compound.

In various embodiments, *L. crispatus* can be employed in various bacterial formulations to enhance the health of an individual's vagina. Preferably, *L. crispatus* is included with amounts of other ingredients, including at least one of probiotics, prebiotics, and other beneficial ingredients. In certain embodiments, at least one, but often at least two of *L. reuteri* and/or *L. johnsonii* and *L. crispatus* are used in a beneficial bacterial composition for topical administration, with the objective being to generate desired amounts of metabolites sufficient to reduce inflammation, especially through the production of tryptophan metabolites, believed to act as AHR agonists. In one embodiment, live bacterial cells of *Lactobacillus crispatus* are administered to the surface of an individual's vagina at a dosage of at least 10.sup.8 CFU to reduce inflammation through the localized production of tryptophan metabolites. Preferably the formulation also includes glycogen and a stimulant for the production of ceramide. The metabolites produced by the *L. crispatus* applied to the kin include indole-3-acetic acid, IAid, Indole-3-Ethanol, Indole-3-pyruvate, and indole-3-aldehyde. Thus, the localized production of tryptophan-derived bacterial metabolites reduces the amount of inflammation the individual would otherwise experience. Preferred formulations include a combination of live *L. crispatus*, prebiotic glycogen, and at least one barrier-enhancing/moisturizing compound. In certain embodiments *L. crispatus* is combined with Human milk human milk glycans to facilitate the generation of beneficial tryptophan metabolites.

A particular method for reducing the likelihood of vaginal inflammation in an individual human being is directed to the administration of a therapeutically effective amount of a bacterial formulation comprising at least one, and preferably at least two, of a live bacteria selected from the group consisting of *L. reuteri*, *L. johnsonii* and *L. crispatus*, and *Nitrosomonas eutropha*, wherein at least some bacteria in the bacterial formulation have been modified by using a using a clustered regularly interspaced short palindromic repeats (CRISPR) CRISPR associated protein (Cas) system or a CRISPR from *Prevotella* and *Francisella* 1 (Cpf1) system to enhance the generation of a tryptophan metabolite.

In certain embodiments, tomatidine is administered to improve the vaginal health of an individual. Tomatidine is present in high amounts in the unripe green tomato and in much lower amounts in the ripe red tomato. This is consistent with a role for tomatidine in protecting the unripe tomato against consumption, with the reduction in tomatidine levels in the ripe fruit then enabling consumption of the fruit and dispersal of the seeds by the consumer. Moderate amounts of tomatidine can activate adaptive cellular stress responses in muscle cells and thus, counteract age-related dysfunction and degeneration.

While not bound by theory, it is believed that such administration of tomatidine extends the lifespan and healthspan of humans and other mammals by inducing mitochondrial hormesis via the induction of ROS production. This further entails the activation of certain cellular and antioxidant pathways, including the SKN-1/Nrf2 pathway, which results in increased mitophagy. The selective removal of damaged or dysfunctional mitochondria by mitochondrial autophagy, termed mitophagy, is believed to be a feature of a treatment to extend an individual's lifespan in a safe and effective manner. Mitophagy modulates bioenergetics and survival in various diseases by reducing redox and damage. Impaired mitophagy occurs in physiological aging, as well as in certain diseases, such as sarcopenia and also believed to be present in cachexia. In certain embodiments, the administration or delivery of certain noxious chemicals are believed to counteract aging and age-related disease by inducing adaptive hormetic stress responses in cells. In other embodiments, the inclusion of rapamycin administration is employed to improve the healthspan of humans as it is further related to mitophagy. The methods and systems as set forth herein are directed to the extension of human life span in a fashion that promotes healthy aging and counteracts disease processes related to age-related disease, including but not limited to osteoporosis.

Tomatidine administration as described in the present specification is believed to contribute to a delay in the physiological aspects of aging, and thus, is able to prevent, treat and reduce age-related diseases and conditions, including but not limited to those suffered primarily by women, e.g. osteoporosis. For example, it is believed that tomatidine increases mitochondria DNA content and muscle fitness and lowers adiposity, as well as decreases skeletal muscle atrophy. While not bound by theory, it is believed that the administration of tomatidine maintains homeostasis by modulating mitochondrial biogenesis and induces mild oxidative stress, which activates the above referenced pathways to induce mitophagy. The amount of tomatidine administered is believed to be important to achieve its desired age fighting effects, with at least about 10 micro-mole, and more beneficially with between about 25 micro-mole and 50 micro-mole being preferred. Moreover, administration of tomatidine is believed to increase the production in an individual of amounts of certain amino acids, such as free amino acids of leucine, threonine, tryptophan, arginine, histidine, valine, isoleucine, and methionine. Such administration is also believed to affect ROS regulation and metabolism. As aging is known to negatively affect mitochondrial quality and biogenesis, the use of tomatidine to enhance mitophagy can be employed to reduce the amount of neurodegeneration and cellular dysfunction of cell metabolism, especially by inducing an increase in Nrf2/ARE reporter activity. Upon activation by ROS, Nrf2 translocates from the cytoplasm of a cell to the nucleus, where it binds to the ARE region to transcriptionally activate genes encoding antioxidant proteins. Thus, tomatidine administration activates the Nrf2-ARE pathway by inducing cells to increase levels of ROS, resulting in the contribution to mitophagy induction. While not bound by theory, it is also believed that administration of tomatidine as described herein acts via multiple stress response pathways, such as, in addition to the Nrf2 pathway referenced above, through the activation of the mitochondrial unfolded protein response (UPR mt). Compromised mitochondrial quality and function is related to pathological aging and disease and the accumulation of damaged mitochondria within cells triggers apoptosis, inflammation and cell senescence. Sarcopenia is observed in aging individuals, with almost 25% of those over 60 years old experiencing the same, rising to over 50% by the age of 80. Tomatidine is believed to preserve muscle function during aging and therefore extends lifespan by improving mitochondrial quality by reducing muscle atrophy. Sarcopenia is therefore common in aging and is associated with the deterioration of muscle fiber cells and with infiltration of adipocytes and inflammatory immune cells, impairing the generation of new myocytes. In various embodiments of the present invention, the employment of tomatidine is not resultant from effects on muscle stem cells or immune cells, but rather, is directed to the effect that tomatidine has in influencing the muscle cells themselves as it is believed that the mechanism of action is directed to processes occurring within skeletal muscle fiber cells.

Various aspects of the present invention are directed to the induction of mitophagy by the administration of tomatidine, especially via the microbiome cells of an individual as otherwise described herein, so as to enhance the quality of the cellular mitochondrial pool and/or mitochondrial biogenesis. Support for this theory of action can be found, for example, in studies of premature aging disease, such as Hutchinson-Gilford progeria syndrome, caused by a mutation of the nuclear architectural proteins lamin A and C. Such patients showed profound growth delay and premature aging phenotypes, including cardiac muscle and skeletal muscle pathologies. It is known that Nrf2 activity contributes to premature aging and that activation of the Nrf2 pathway ameliorates such disease. One aspect of the present invention is therefore directed to the administration of tomatidine, in particular as described herein via expression by or in conjunction with various bacteria in an individual's microbiome, so that it triggers mitophagy and induces Nrf2 activation. A signaling role for ROS in the stimulation of mitophagy in cells under mild stress supports the use of tomatidine as described herein, as moderately elevated ROS levels have been seen as inducing mitophagy, which has the effect of clearing aged or dysfunctional mitochondria. If ROS levels are too high, however, or if mitophagy is compromised, mitochondrial dysfunction becomes exacerbated, demonstrating that ROS levels have a dynamic role in health and aging disease. Employment of tomatidine to achieve a moderate elevation of ROS levels is therefore one objective of various embodiments of the present invention, but with care not to achieve excessive ROS levels, thus accomplishing the desired goal of enhancing cellular stress resistance in a manner that is disease protective. Tomatidine is therefore preferably administered in effective amounts that induce a moderate increase in ROS levels that is necessary to trigger mitophagy without demonstrating mitochondrial dysfunction.

Tomatidine is not believed to have significant anti-microbial effects, at least when used alone. When co-administered with other compounds, however, it is believed that there is a synergistic effect and therefore, tomatidine is viewed as an antibiotic potentiator when used with ampicillin, etc. Preferably, tomatidine, in certain embodiments is used at a concentration of about 200 micro grams per mL. Thus, in several embodiments, the use of tomatidine administration in an individual is employed to synergistically enhance the action of various antibiotics against certain bacteria. Such synergistic effects are believed to be also accomplished when tomatidine expression/administration in an individual is coupled of the co-administration with at least one of the following: p53 protein, rapamycin, resveratrol, metformin, spermidine, xylitol, glucosamine and methylene blue.

Resveratrol (3,4',5-trihydroxystilbene; $C_{14}H_{12}O_3$) is a polyphenolic phytoalexin found in grapes, berries, peanuts, and wines. Resveratrol has been viewed as an antioxidant, anti-inflammatory, anti-apoptotic, and anticancer agent. Moreover, it has been reported that resveratrol modulates mitochondrial function, redox biology, and dynamics in both in vitro and in vivo experimental models. Resveratrol also attenuates mitochondrial impairment induced by certain stressors. Resveratrol upregulates, for example, mitochondria-located antioxidant enzymes, decreasing the production of reactive species by these organelles. Resveratrol also triggers mitochondrial biogenesis, ameliorating the mitochondria-related bioenergetics status in mammalian cells. Brain cells (both neuronal and glial) are susceptible to mitochondrial dysfunction due to their high demand for adenosine triphosphate (ATP). Additionally, brain cells consume oxygen ($O_2$) at very high rates, leading to a proportionally high mitochondrial production of reactive species. One aspect of various embodiments of the present invention is the maintenance of mitochondrial function in various cell types to address degenerative diseases, which involve mitochondrial impairment and increased generation of reactive species, leading, for example, to neuroinflammation and cell death. The mechanism by which resveratrol protects mitochondrial function and dynamics is not completely understood, but it is known that resveratrol is able to induce cytotoxicity depending on its dosage. Resveratrol produced by the microbiome of an individual (or precursors thereof) can be employed to improve the dysregulation of the gut microbiota induced by a high-fat diet, as it results in increasing the ratio of *Bacteroides*-to-*Firmicutes* and also increases the growth of *Lactobacillus acidophilus* and *bifidobacterium* in humans. It is believed that resveratrol modifies the intracellular environment by changing the oxidizing milieu into a reducing milieu and upregulates intracellular glutathione, potentiating a signal transduction cascade that results in mitophagy, and thus paves the way to an anti-aging environment.

Mammalian/mechanistic target of rapamycin (mTOR) is an intracellular protein complex that is responsive to both growth factors and nutrient availability, and which also impacts mitochondrial function. It is comprised of the TOR kinase—known as mTOR in mammals. The TOR signaling pathway is highly conserved in eukaryotes and is functionally defined as the target of the highly-specific antifungal, rapamycin. mTOR and aging appear to have co-evolved, suggesting that cancer is inexorably linked to fundamental aspects of life. Rapamycin can be employed, via production by or used in conjunction with an individual's microbiome, to achieve the objective of delaying the effects of aging and thus, reduce diseases associated with aging. Age-associated diseases interface with TOR and its signaling systems, and thus, employment of rapamycin (alone or in concert with the various other agents described herein) provides the ability to target both aging and its associated diseases.

In certain embodiments, precursors of one of xylitol, rapamycin and tomatidine are administered via an individual's own microbiome as a way to deliver a therapeutic treatment that works on everyone despite the distinct and acknowledged differences between an individual's microbiome. The differences of each individual's microbiome works in favor of this approach as delivery of rapamycin via one's own microbiome is naturally customed tailored as focusing on modification of an individual's microbiome provides desired anti-aging agents while maintaining the distinct character of an individual's microbiome. Aging is therefore possible to treat in a personalized way by taking into account the individual's unique microbiome. The present invention provides a way to tailor preventive measures and treatments to different individuals. Mechanical loading plays a major role in the regulation of skeletal muscle mass, and the maintenance of muscle mass profoundly influences health and quality of life. Signaling by the mammalian/mechanistic target of rapamycin (mTOR) is a key component of the mechanotransduction pathway. Employment of an individual's microbiome to administer effective amounts of rapamycin to the individual is one way in which to modulate mTOR signaling, thus affecting muscle mass and associated bone density.

To comply with written description and enablement requirements, all references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material. Incorporated herein by this reference are the following US patent publications: 20170079947 to Richards; 20140296139 to Cohen et al.; 20160175327 to Adams et. al.; 20100081681 to Blagosklonny and 20120283269 to Blagosklonny; U.S. Patent Publication Nos. 20140030332 to Baron, et al., 20070123448 to Kaplan et al.; 20160000841 to Yamamoto, et al.; 20160095316 to Goodman et al.; 20160158294 to Von Maltzahn; 20140294915 to Kovarik; U.S. Pat. No. 8,034,601 to Boileau et al.; 20130225440 to Freidman, et al., 20150071957 to Kelly et al., 20160151428 to Bryann et al.; 20160199424 to Berry et al.; 20160069921 to Holmes, et al.; 20160000754 to Stamets; U.S. Pat. No. 9,044,420 to Dubensky, Jr, et al.; 20160120915 to Blaser et. al.; 2014/0349405 to Sontheimer; 2014/0377278 to Elinav; 2014/0045744 to Gordon; 2013/0259834 to Klaenhammer; 2013/0157876 to Lynch; 2012/0276143 to O'Mahony; 2015/0064138 to Lu; 2009/0205083 to Gupta et al.; 201/50132263 to Liu; and 2014/0068797 to Doudna; 2014/0255351 to Berstad et al.; 2015/0086581 to Li; PCT/US2014/036849 and WO 2013026000 to Bryann; U.S. Pat. Publication No. 2015/0190435 to Henn; 2012/0142548 to Corsi et al.; U.S. Pat. Nos. 6,287,610, 6,569,474, U.S.2002/0009520, U.S.2003/0206995, U.S.2007/0054008; and U.S. Pat. No. 8,349,313 to Smith; U.S. Pat. No. 9,011,834 to Mckenzie; 20150004130 to Faber et. al, 20160206666 to Falb; 20160206668 to Kort et. al; and WO2015069682A2 to Asesvelt, et. al.; 20160199424 to Berry et al.; 20130326645 to Cost et al.; 2012/0276149 to Littman; and U.S. Pat. No. 9,314,489 to Kelly et. al.; 20160243132 to Adams, et. al.; U.S. Pat. No. 9,549,842 to Kovarik; 20200032224 to SCHAEFER et. al.; 20170014341 To Armer, et. al. and U.S. Pat. No. 10,683,323 to Prakash, et.

al., US 20230106721 to Catania, et. al., US 20070072797 to Robinson, et. al.; U.S. Pat. No. 11,504,387 to Horcajada et. al.; US 20230106721 to Catania, et. al. US 20230041103 and US20210322505 to Rodriguez Vilaboa and WO2022208458 to Biffi.

Also incorporated by reference are the following: 20230129072 to Strgar; 20220047651 to Robb, et. al. U.S. Pat. No. 11,571,458 to Parks, et. al.; U.S. Pat. No. 11,564,667 to Dominguez-Bello; 20210177744 to Klingman; 20220273736 to Widschwendier, et al.; US20190307817 to Fichorova; US 2022-0370516 to Kreuger, et. al.; US20200206279 to Ambrogio.

Certain embodiments of the present invention are directed to bacterial production by genetically modified bacteria to produce or to be used in conjunction with one of xylitol, tomatidine and/or rapamycin, especially the precursors thereof such that biosynthesis of these agents can be provided to those in need. Bacteria that may produce xylitol include *Corynebacterium* sp., *Enterobacterium liquefaciens, Serratia marcescens, Bacillus coagulans* and *Mycobacterium smegmatis*. Certain embodiments of the present invention involve the production of xylitol by genetically modified bacteria, including those listed above, preferably using CRISPR systems to include genes responsible for xylitol production in yeasts, such as *Pichia stipitis*. The genes of yeasts that encode for xylitol production are well known by those of skill in the art. Incorporation of these genes into suitable bacterial vectors is within the skill of those in the art. For example, deletion of the *Escherichia coli* xylulokinase gene (xylB) is essential for achieving high xylitol titers from xylitol-producing *E. coli* strains growing on glucose in the presence of xylose. The yeast *Pichia stipitis* naturally produces xylitol. Replacement of xylB with XYL3 results in drastically enhanced xylitol titers from *E. coli* strains co-expressing xylose reductase during growth on xylose. Biological conversion of xylitol using microorganisms is achieved in some embodiments via using genetically modified microorganisms capable of converting readily available carbon sources, such as D-glucose, into xylitol.

In certain embodiments, a level of butyrate in an individual's gut microbiome is increased and such individual is provided with tributyrin. In others, the individual is separately administered a helminthes extract as the exposure of one's microbiome to such extract is believed to trigger effective immunity against certain conditions and diseases. In some preferred embodiments the at least two bacteria selected from the group consisting of Peptococcus, Dialister, *Gardnerella vaginalis, Bacteroides* and *Clostridiu* are reduced in the vagina of the individual being treated.

Other embodiments involve steps of reducing the amount of short chain fatty acid (SCFA) production in the individual's vagina by reducing a population of at least two of the following: *Streptococcus, Bacteroides, Prevotella, Mycoplasma, Ureaplasma, Finegoldia*, Mobiluncus, Leptotrichia, Eggerthella, *Veillonella*, Dialister, Atopobium, Megasphaera, Sneathia. *C. albicans* and *Gardnerella vaginalis*. Preferably at the same time that these bacteria are reduced in the vagina, there is an increase in SCFAs in the individual's gut microbiome. In various preferred embodiments, ammonia oxidizing microorganisms are introduced to an individual's vagina, e.g. *N. eutropha*, to achieve the health benefits otherwise disclosed herein. In other embodiments, using probiotics, the hypoxic conditions of an individual's vagina are reduced so as to combat and reduce any existing population of anaerobic bacteria in the individual's vagina. In many embodiments, one objective is to maintain a pH of the individual's vagina at below 4.5.

Certain embodiments of the present invention are directed to a method to reduce the likelihood of a dysbiosis of the vaginal microbiome in an individual, such method involving the provision a bacterial formulation that includes at least two species of live bacteria selected from the group consisting of *L. reuteri, L johnsonii* and *L. crispatus*. Preferably such bacterial formulation includes at least one prebiotic having glycogen as a component thereto. The bacterial formulation is administered to an individual's vagina in an amount sufficient for the bacterial formulation to generate an amount of tryptophan metabolites sufficient to act as aryl hydrocarbon receptor (AHR) agonists, thereby reducing inflammation in the individual's vagina. A preferred embodiment includes a bacterial formulation that includes *L. crispatus* and at least one of a probiotic, prebiotic, and a moisturizer. Such a bacterial formulation is preferably applied to an individual's vagina at night so that it remains thereon during a sleeping pattern of the individual. In other embodiments, the individual is further administered either or both tomatidine and rapamycin in therapeutically effective amounts due to the beneficial health aspects of such compounds as disclosed herein, and in a most preferred embodiment, is administered vaginally to be absorbed via the vaginal mucosal tissues of the individual. In certain embodiments, the administration of at least one of tomatidine and rapamycin is achieved using a bioadhesive strip that has a first and second side, with the second side having a bioadhesive that is adapted to bind to a mucosal membrane for at least 1 hour. Such strip may include a polymer selected from the group consisting of pullulan, hydroxypropylmethyl cellulose, hydroxyethyl cellulose, sodium alginate, polyethylene glycol, tragacanth gum, guar gum, acacia gum, arabic gum, carboxyvinyl polymer, amylose, high amylose starch, hydroxypropylated high amylose starch, dextrin, chitin, chitosan, levan, elsinan, collagen, zein, gluten, soy protein isolate, whey protein isolate, casein and mixtures thereof.

In several embodiments, the method is intended to treat a postmenopausal woman. In preferred embodiments, prior to the step of providing the bacterial formulation, a number of resident bacteria in the individual, namely in a woman's vagina, are reduced using one of an antibiotic, or a clustered regularly interspaced short palindromic repeats (CRISPR) CRISPR associated protein (Cas) system or a CRISPR from *Prevotella* and *Francisella* 1 (Cpf1) system. The later can be employed to selectively kill undesired and/or pathogenic bacteria without killing commensal bacteria that are desired. In certain embodiments, the population inside an individual's vagina is increased by providing a population of bacteria from one or more of the genera *Lactobacillus, Brevundimonas*, and *Odoribacter*. In other embodiments, the method further involves decreasing a population of bacteria of the genus *Streptococcus* in the individual's vagina. In still other embodiments, the method includes reducing in the individual's vagina a population level of the bacterium *Gardnerella vaginalis*.

Certain aspects of the present invention are directed to preserving mucus in the individual's vagina by reducing a population of bacteria in the individual's vagina selected from the group consisting of *Prevotella, Gardnerella*, and *Bacteroides*. In other embodiments, with the objective being to reduce a risk of a newborn infant developing one of infantile asthma, wheezing and allergies, the population of *Veillonella* and *Lachnospira* bacteria in a woman's vagina is reduced, preferably starting at the late stages of pregnancy, such as during the sixth or seventh month.

The maternal microbiome is essential for the healthy growth and development of offspring and has long-term effects later in life. Beginning its regulation of fetal health and development during pregnancy, the maternal microbiome continues to affect early microbial colonization via birth and breastfeeding and further regulates an infant's immune and brain development. and affects the risk of related diseases. Certain aspects of the present invention are directed to modulating offspring development by the probiotic intervention during pregnancy and breastfeeding.

While not bound by theory, it is believed that the abundance of *Prevotella* during a mother's pregnancy is closely related to the risk of food allergy in the infant, with a higher abundance of *Prevotella* in the maternal gut being indicative of a lower risk of food allergy in infants at 12 months. Thus, certain embodiments are directed to increasing the populations of *Prevotella* in the material gut during pregnancy. Moreover, certain maternal microbial metabolites (i.e. AhR ligands and SCFAs) and the cytokine-mediated response (IL-6) synergistically regulate the early establishment of immunity before birth. In certain embodiments, probiotic supplementation (especially in postmenopausal women) is employed as a way to manage menopause-related diseases. In particular embodiments, oral probiotic formulations including *Lactobacillus* ssp. *casei, helveticus, rhamnosus*, and *reuteri*—are administered due to their pleiotropic beneficial effects on health. Such bacterial formulations promote intestinal calcium absorption and delay potential bone damage for women at risk of osteoporosis or osteopenia.

In other preferred embodiments, exclusively *L. crispatus* bacteria are present in formulations and thus, certain claims are directed to formulations either consisting of or consisting essentially of select *L. crispatus* strains as described herein. Moreover, in preferred embodiments, there is added to the formulation a prebiotic that contains maltose, and more preferably consisting essentially of just maltose as a sugar and preferably not glycogen, as it is believed that maltose is a semi-selective fuel source for *L. crispatus*. In preferred embodiments, the bacterial formulation is administered as vaginal suppositories, even more preferably in the form of a slow-release tablet, which is preferably inserted with a device. Certain embodiments of the present invention include in a formulation the following: Maltose, Calcium L-lactate; L-glutamine Magnesium citrate dibasic and L-Cystine, with preferred embodiments consisting essentially of such ingredients, in addition to the *L. crispatus* strains as mentioned herein. L-glutamine is believed to serve as a building block for the *L. crispatus* cell wall. Glutamine is believed to be an amine donor in peptidoglycan biosynthesis and in the amidation of the aspartate residues in peptide cross-links. Magnesium citrate dibasic is believed to serve as a buffer to balance the acidifying activity of calcium lactate and *Lactobacillus* growth. L-Cystine (the oxidized dimeric form of cysteine) is believed to afford the creation and maintenance of a high positive redox potential in the vagina, favoring the growth of the select *L. crispatus* strains. Such formulation therefore confers host protection from numerous vaginal health conditions, reduces discharge and odors and confers other benefits like comfort and hydration. In other embodiments, oral administration of oral D-mannose is employed to help prevent undesired *E. coli* growth and is also believed to delay recurrent UTIs. It is believed that acid-tolerant *L. crispatus* in the consortium formulations set forth possess a growth advantage by accessing nutrients with enzymes that are optimally set to operate at a low pH. Preferred strain combinations are selected to include specific characteristics, including the asparagine synthase B gene, temporal stability, max unique genes, and the ability to inhibit vaginal pathogens UPEC, *G. vaginalis*, *P. bivia, S. aureus*, and *S. Agalactiae*. Together with the strains of *L. crispatus*, such formulation provides a superior vaginal product that facilitates a modification to the vaginal microbiome into a CST1 (*L. crispatus* dominant) ecology.

While not bound by theory, it is believed that five major kinds of vaginal communities with markedly different species composition ("community state types," or CSTs) occur in reproductive-age women. CST's are defined by the dominant microbial species present: *Lactobacillus crispatus* (CST I), *L. gasseri* (CST II), *L. iners* (CST III), and *L. jensenii* (CST V). CST IV is typified by a lower proportion of lactic acid producing bacteria and a relatively higher proportion of anaerobic organisms including the species *Gardnerella vaginalis*. Vaginal microbiomes classified as CST1 are associated with vaginal health: *L. crispatus* does not elicit mucosal inflammation, is linked with prevention or reduction of the incidences of urogenital diseases such as bacterial vaginosis (BV), yeast infections, sexually transmitted infections (STIs), and urinary tract infections (UTI), as well as to positive impacts on fertility and reduction of adverse pregnancy outcomes, such as pre-term birth. Even within a protective CST1, the presence of specific *L. crispatus* strains may be associated with greater stability and resilience of the vaginal microbiome. Vaginal microbiomes containing such strains (including VM-02) returned to baseline more quickly after disruptions, such as menses.

In preferred embodiments, and using VM-02 as a representative example that one of ordinary skill in the art will appreciate as representative of a wider range of bacterial formulations, preferred embodiments are in a form of an extended-release mucoadhesive suppository vaginal tablet, such as a 850 mg oblong (17×7.8 mm) tablet. The following formulation (Table 1) represents the results of a batch production for the VM-02 consumer clinical trial to assess safety and tolerability.

VM-02 is comprised of 3 proprietary strains of live *Lactobacillus crispatus* bacteria (1×109 CFU each): *L. crispatus* LUCA011, *L. crispatus* LUCA103, and *L. crispatus* LUCA009. These VM-02 LUCA strains were rationally designed through a platform (e.g. the LUCA Biologics Platform); the strains are genetically synergistic and selected based on a) presence of a unique biomarker associated with resilience, b) maximizing unique gene content between strains and c) exceptional inhibition of uro-pathogenic *E. coli* (UPEC) and other pathogens that cause vaginal infections.

TABLE 1

Formulation of the extended-release mucoadhesive suppository vaginal tablet produced for the VM-02 clinical trial.

| Ingredient | Formulation per Tablet | Quantity Used in Log DP122010 per Tablet (mg) |
| --- | --- | --- |
| VM-02 *L. crispatus* strains: | | |
| LUCA 009 | $1.0 \times 10^9$ CFU | 27.80$^a$ |
| LUCA 011 | $1.0 \times 10^9$ CFU | 52.62$^a$ |
| LUCA 103 | $1.0 \times 10^9$ CFU | 58.82$^a$ |
| Hydroxypropyl-methylcellulose | 7.50% | 63.75 |
| Magnesium Stearate | 1.00% | 8.50 |
| Maltose | 11.76% | 99.96 |
| Calcium Lactate | 7.06% | 60.01 |
| DiBasic Magnesium Citrate | 3.53% | 30.01 |

TABLE 1-continued

Formulation of the extended-release mucoadhesive suppository vaginal tablet produced for the VM-02 clinical trial.

| Ingredient | Formulation per Tablet | Quantity Used in Log DP122010 per Tablet (mg) |
|---|---|---|
| L-glutamine | 5.88% | 49.98 |
| L-cystine | 1.18% | 10.03 |
| Microcrystalline Cellulose | Filler-fill up to 100% | 388.54 (45.71%)[b] |
| Total | | 850 mg |

[a]Will differ per lot based on CFU/g obtained during production of individual *L. crispatus* strains.
[b]Filler-will differ per lot based on weight of *L. crispatus* strain used.

Additional ingredients may play a role in conditioning the local vaginal environment to support the growth and persistence of the probiotic strains. These ingredients can be found in the USP/NF compendium (with the exception of ammonium citrate which serves as a buffer and is ACS reagent grade), many of them commonly used as excipients, and each have been studied independently. They are commonly found in the human body, or are salts thereof, and most are commercially available dietary supplements.

The supporting ingredients include:

Maltose: Serves as a carbon and energy source for the active *L. crispatus* strains. Maltose is a common breakdown product of host-produced glycogen in the vaginal epithelium.

Calcium L-Lactate: a stable salt of lactic acid, which is commonly used in tableting and for vaginal acidification. Acid-tolerant *L. crispatus* in the consortium has a growth advantage by accessing nutrients with enzymes that are optimally set to operate at low pH.

L-glutamine: serves as a building block for the *L. crispatus* cell wall. Glutamine is used as an amine donor in peptidoglycan biosynthesis and in the amidation of the aspartate residues in peptide cross-links.

Magnesium citrate dibasic: serves as a buffer to balance the acidifying activity of calcium lactate and *Lactobacillus* growth.

L-Cystine: the oxidized dimeric form of cysteine and is commonly found in the vaginal environment. The addition of cystine affords the creation and maintenance of a high positive redox potential in the vagina, favoring the growth of *L. crispatus*.

Chemically inactive excipients may be used as either filling or binding agents in order to form a tablet or powder. The excipients that may be used in the formulations are commonly used pharmaceutical excipients and are below the amounts listed in FDA's Inactive Ingredient Database (IID). The inactive excipients that facilitate the VM-02 tablet and capsules and their intended functions within the formulation are as follows:

Cellulose Microcrystalline (Vivapur 200×LM): large size MCC grade with excellent flow properties for a variety of direct compression formulations.

Magnesium stearate (Ligamed MF2V): can result in a good speed of release during tablet pressing and constant performance of the tablets such as hardness and dissolution profiles.

HPMC [Metolose 905H15000] is used as a binder for solid dosage forms such as tablets and granules.

A preferred vaginal suppository of one embodiment of the present invention is comprised of three strains of live *L. crispatus* bacteria (1×10 9 CFU): *L. crispatus* LUCA009, *L. crispatus* LUCA011, and *L. crispatus* LUCA103, in addition to excipients to aid the activity of such *L. crispatus* stains, and the excipients used to manufacture the tablet. Preferably, these strains are isolated from clinical vaginal samples of healthy women with a stable, *L. crispatus*-dominant vaginal microbiome, and selected for consortium assembly based on their genetic synergy, following ecological principles that enable the consortium's persistence and co-functionality, for the prevention of recurrent urinary tract infection (rUTI) in premenopausal women. The tablet is intended to modulate the vaginal microbiome to a state non-permissive to reinfection in combination with an enteral monosaccharide that acts locally within the urinary tract to prevent binding of a causative pathogen to epithelial cells. By addressing both the intravaginal and urinary tract sources of urinary pathogens, the combinatorial treatment aims to eliminate the dual reservoirs of pathogens that lead to recurrence of UTIs while supporting the establishment of a resilient *Lactobacillus* population.

In a preferred embodiment, these *L. crispatus* strains predominate in a healthy vaginal microbiota and protect against colonization with uropathogens. The vaginal suppository is preferably administered concurrently with orally ingested D-mannose, which complements the bacterial formulation's intravaginal activity. It is believed that oral D-mannose helps to minimize bladder colonization with gram negative bacteria, especially *E. coli*, by blocking a receptor that allows bacteria to bind to the bladder epithelium, which is believed to delay the time to recurrent rUTIs. Oral D-mannose is a commonly used over-the-counter dietary supplement, which at higher doses can cause some diarrhea, but is generally well tolerated. One aspect of various embodiments is to employ both the bacterial formulation together with an orally ingested D-mannose in the management of urinary tract infections, due to their complementary mechanisms of action. Together this regimen provides a multi-pronged approach to address both urinary and vaginal reservoirs of pathogens and reduces UTI recurrence. In contrast to prior technologies utilizing a single strain of *Lactobacillus*, embodiments of the present invention employ at least three strains with minimal non-redundant genes to establish a genomic and metabolomic driven reconstitution of a vaginal microbial ecosystem.

In certain embodiments, methods involve an interventional treatment that comprises of administering a bacterial formulation comprising at least three strains (e.g. as identified above) in the form of a mucoadhesive tablet suppository (vaginal) in combination with oral monosaccharide D-Mannose, supplied in 2-gram sachets. Preferred intravaginal suppositories are 500 mg and oblong (17×7.8 mm) tablets. Table 1 above contains the components of interventional treatment: strains (active live biotherapeutic product) and supporting ingredients. In preferred embodiments, an oral monosaccharide is packaged in 2-gram sachets and stored at room temperature (25° C.), consisting of D-mannose, an OTC monosaccharide shown to block FimH adhesion protein of dominant causative pathogens in UTI.

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other methods and systems for carrying out the several purposes of the present invention. It is important, therefore, that the claims be regarded as including any such equivalent construction insofar as they do not depart from the spirit and scope of the present invention.

What is claimed is:

1. A method to reduce the likelihood of a dysbiosis of the vaginal microbiome in an individual, comprising: providing a bacterial formulation that includes at least three different, distinct strains of *Lactobacillus crispatus*, administering the bacterial formulation to an individual's vagina in an amount sufficient for the bacterial formulation to generate an amount of tryptophan metabolites sufficient to act as aryl hydrocarbon receptor (AHR) agonists to thereby reduce inflammation in the individual's vagina, wherein the strains of *Lactobacillus crispatus* are genetically synergistic and inhibit uro-pathogenic *E. coli*.

2. The method of claim 1, wherein the bacterial formulation is applied to an individual's vagina at night so that it remains thereon during a sleeping pattern of the individual.

3. The method as set forth in claim 1, further comprising administering at least one of tomatidine and rapamycin to the individual.

4. The method of claim 1, wherein at least one of the three *L. crispatus* strains is alive.

5. The method as set forth in claim 1, wherein the individual is a postmenopausal woman.

6. The method of claim 1, wherein said bacterial formulation includes at least one prebiotic having glycogen as a component thereof.

7. The method of claim 1, wherein the bacterial formulation is applied topically and optionally further includes a moisturizer.

8. The method of claim 1, further comprising introducing ammonia oxidizing microorganisms to the individual's vagina.

9. The method of claim 1, wherein the bacterial formulation is isolated from the human vaginal tract of a woman.

10. The method of claim 1, wherein the bacterial formulation is in the form of a mucoadhesive tablet suppository.

11. The method of claim 10, wherein the mucoadhesive tablet suppository is adapted to bind to a mucosal membrane for at least 1 hour, said bioadhesive including at least one polymer selected from the group consisting of pullulan, hydroxypropylmethyl cellulose, hydroxyethyl cellulose, sodium alginate, polyethylene glycol, tragacanth gum, guar gum, acacia gum, arabic gum, carboxyvinyl polymer, amylose, high amylose starch, hydroxypropylated high amylose starch, dextrin, chitin, chitosan, levan, elsinan, collagen, zein, gluten, soy protein isolate, whey protein isolate, casein and mixtures thereof.

12. The method as set forth in claim 1, further comprising, prior to the step of providing said bacterial formulation, reducing the number of bacteria in the individual using one of an antibiotic, a clustered regularly interspaced short palindromic repeats (CRISPR) CRISPR associated protein (Cas) system or a CRISPR from *Prevotella* and *Francisella* 1 (Cpf1) system.

13. The method as set forth in claim 1, further comprising increasing in the individual's vagina a population of bacteria selected from the group consisting of bacteria of the genera *Brevundimonas* and *Odoribacter*.

14. The method as set forth in claim 1, further comprising increasing the production of short chain fatty acids (SCFAs) in the individual's gut microbiome, while reducing the production of SCFAs in the individual's vagina.

15. The method as set forth in claim 1, further comprising preserving mucus in the individual's vagina by reducing a population of bacteria in the individual's vagina selected from the group consisting of *Prevotella, Veillonella, Lachnospira, Bacteroides*, Peptococcus, Dialister, *Gardnerella vaginalis*, Atopobium, Megasphaera, Sneathia, *Mycoplasma, Ureaplasma, Finegoldia*, Mobiluncus, Leptotrichia, Eggerthella, *Streptococcus* and *Clostridium*.

16. The method as set forth in claim 1, further comprising administering to the individual an extract derived from a helminth selected from the group consisting of *Trichuris trichiura* and *Necator americanus*.

17. The method as set forth in claim 1, further comprising, reducing hypoxic conditions of the individual's vagina to reduce an existing population of anaerobic bacteria in their vagina.

18. A method to reduce the likelihood of a dysbiosis of the vaginal microbiome in an individual, comprising: administering to the individual a therapeutically effective amount of a bacterial formulation comprising at least three different strains of *Lactobacillus crispatus*, wherein the at least three strains of *Lactobacillus crispatus* are genetically synergistic and inhibit uro-pathogenic *E. coli*; and maintaining the pH of the individual's vagina at below 4.5.

19. A method to reduce the likelihood of a dysbiosis of the vaginal microbiome in an individual, comprising: providing a bacterial formulation that includes at least three different strains of *Lactobacillus crispatus*; administering the bacterial formulation to an individual's vagina in the form of a suppository and in an amount sufficient for the bacterial formulation to generate an amount of tryptophan metabolites sufficient to act as aryl hydrocarbon receptor (AHR) agonists to thereby reduce inflammation in the individual's vagina and wherein the bacterial formulation comprises live cells of *Lactobacillus crispatus*.

* * * * *